(12) United States Patent
Kogasaka et al.

(10) Patent No.: US 6,371,968 B1
(45) Date of Patent: Apr. 16, 2002

(54) CAVITY RETAINING TOOL FOR BONE SURGERY, A CAVITY RETAINING TOOL FOR GENERAL SURGERY, AN ENDOSCOPIC SURGERY SYSTEM INVOLVING THE USE OF A CAVITY RETAINING TOOL, AND A PROCEDURE FOR SURGERY

(75) Inventors: Takahiro Kogasaka; Akihisa Ogawa; Akio Nakada, all of Hachioji; Shuichi Kimura, Hino; Norio Kobayashi, Kokubunji; Makoto Kuramochi, Tokyo, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 08/855,702

(22) Filed: May 8, 1997

(30) Foreign Application Priority Data

| May 9, 1996 | (JP) | 8-114940 |
| Aug. 2, 1996 | (JP) | 8-204495 |
| Nov. 15, 1996 | (JP) | 8-304323 |
| Dec. 17, 1996 | (JP) | 8-336810 |
| Apr. 11, 1997 | (JP) | 9-092649 |
| May 1, 1997 | (JP) | 9-113978 |

(51) Int. Cl.⁷ ............................................. A61B 17/00
(52) U.S. Cl. .................. 606/190; 606/86; 604/264; 600/201; 600/206
(58) Field of Search .................. 606/99, 86, 104, 606/108, 190, 191, 193, 198; 604/104, 164.01, 164.08, 164.1, 171, 264; 600/114, 206, 207, 208

(56) References Cited

U.S. PATENT DOCUMENTS

| 3,866,601 A | * | 2/1975 | Russell |
| 3,935,863 A | | 2/1976 | Kliger |
| 4,545,374 A | | 10/1985 | Jacobson |
| 4,984,564 A | | 1/1991 | Yuen ............................. 128/20 |
| 5,139,511 A | * | 8/1992 | Gill et al. ..................... 606/198 |
| 5,176,649 A | * | 1/1993 | Wakabayashi ............... 604/164 |
| 5,295,994 A | | 3/1994 | Bonutti ........................ 606/192 |
| 5,310,406 A | | 5/1994 | Sharpe et al. |
| 5,313,962 A | | 5/1994 | Obenchain |
| 5,439,464 A | | 8/1995 | Shapiro |
| 5,454,365 A | | 10/1995 | Bonutti ........................ 600/204 |
| 5,472,426 A | * | 12/1995 | Bonati et al. ................ 604/164 |
| 5,569,290 A | | 10/1996 | McAfee ........................ 606/185 |

FOREIGN PATENT DOCUMENTS

| DE | 42 34 990 A1 | 10/1992 |
| DE | 41 33 298 A1 | 4/1993 |
| DE | 43 18 950 C1 | 9/1994 |
| EP | 0 610 099 A2 | 8/1994 |
| EP | 0 614 647 A2 | 9/1994 |
| FR | 2 701 379 | 8/1994 |
| WO | WO 92/21292 | 12/1992 |
| WO | WO 94/03114 | 2/1994 |
| WO | WO 95/22285 | 8/1995 |
| WO | WO 95/32663 | 12/1995 |

* cited by examiner

Primary Examiner—David O. Reip
(74) Attorney, Agent, or Firm—Armstrong, Westerman & Hattori, LLP.

(57) ABSTRACT

A cavity-retaining tool for bone surgery includes a cavity-retaining sheath which is inserted into the body and forms a cavity to act as a work space for bone surgery, a treatment channel which is placed in the cavity-retaining sheath and guides treatment tools necessary for the treatment of a bone into the space for bone surgery, an observation tool which is attached to the cavity-retaining sheath and by which to observe the operation field within the space for bone surgery, and a fitting portion which is placed at a tip of the cavity-retaining sheath and fits the tip of the cavity-retaining sheath to a bone.

101 Claims, 52 Drawing Sheets

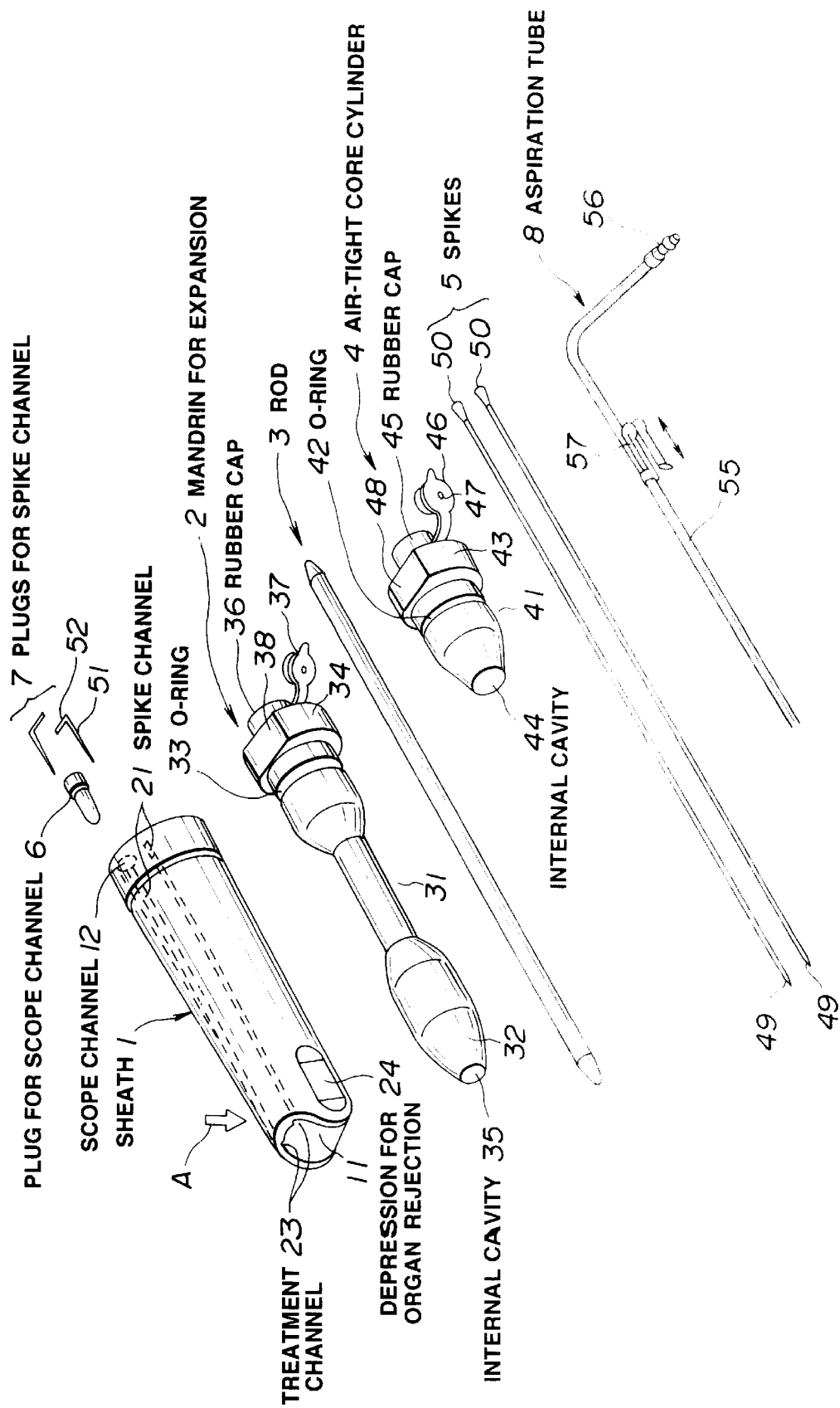

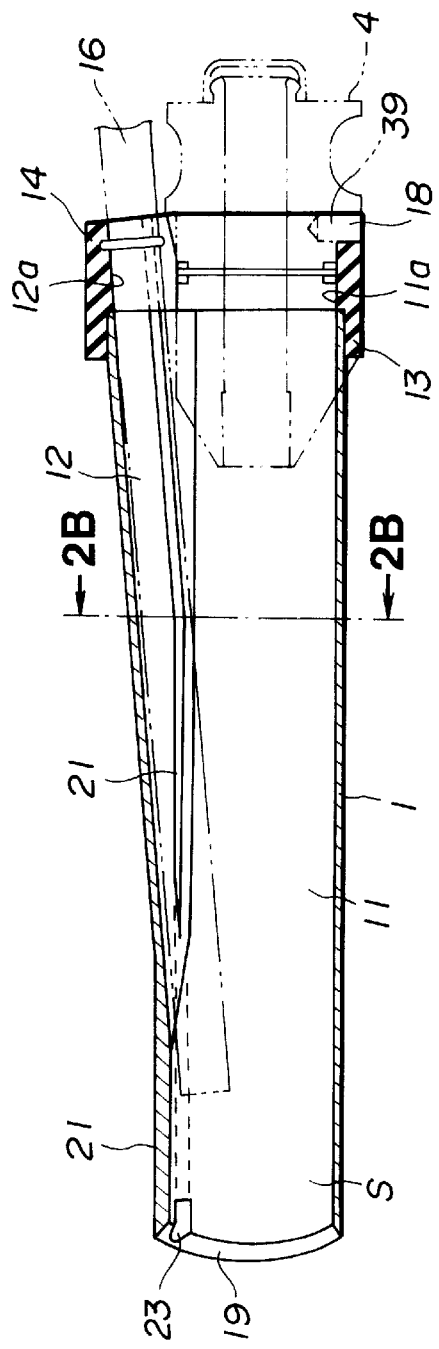
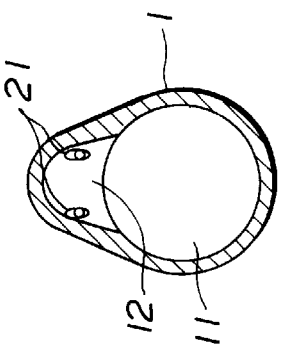
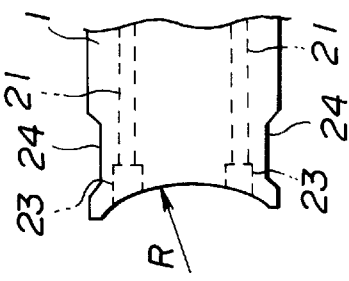

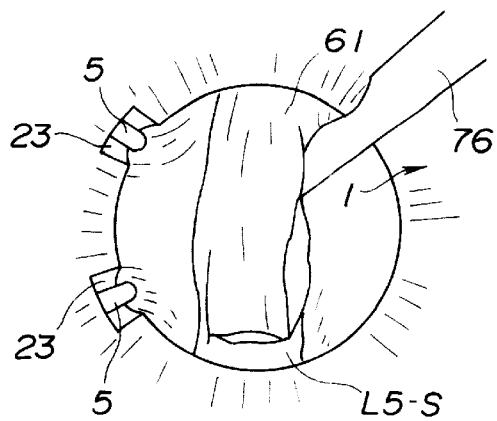
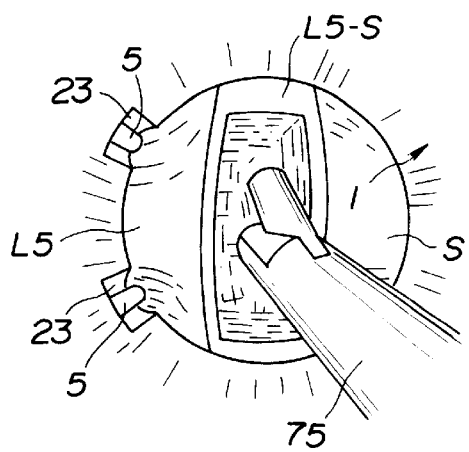
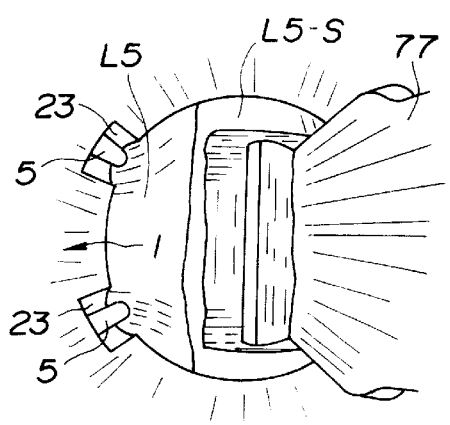
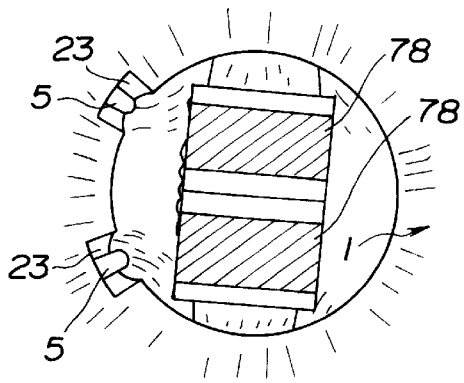
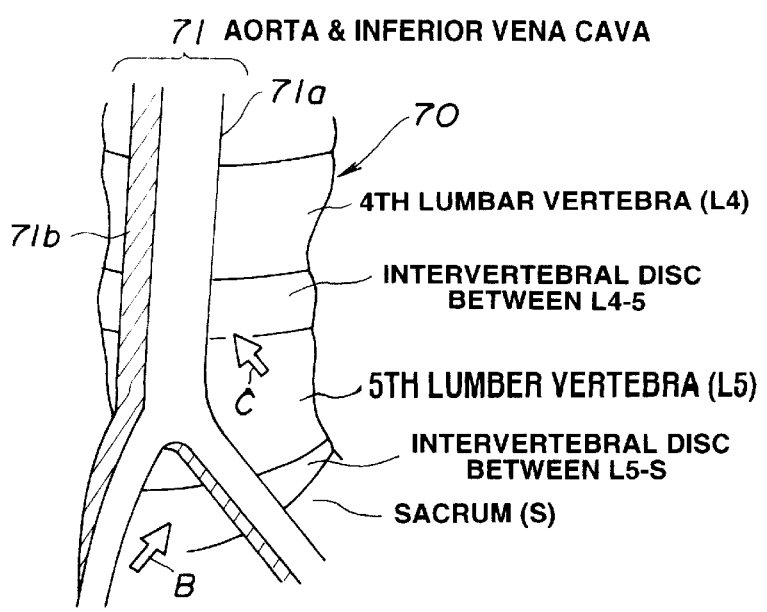

FIG.30
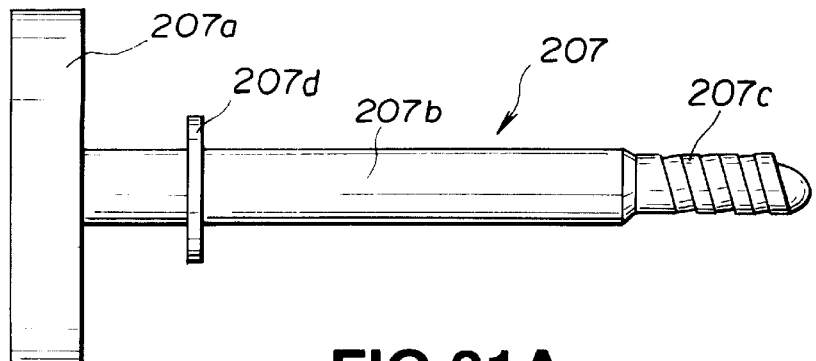
FIG.31A
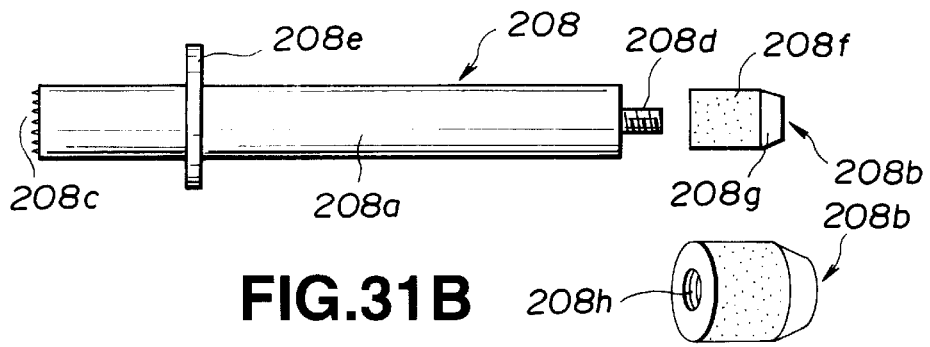
FIG.31B
FIG.32
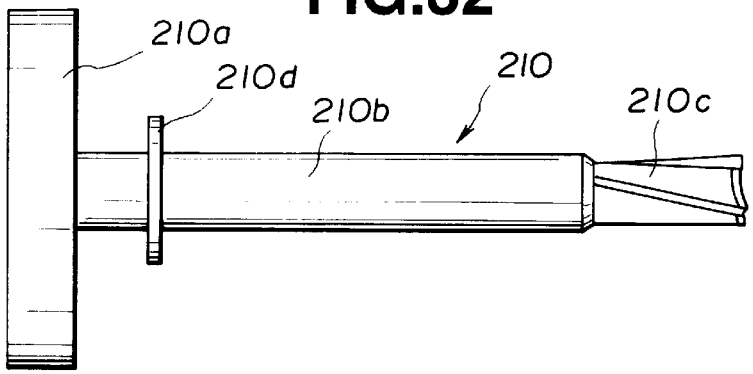
FIG.33
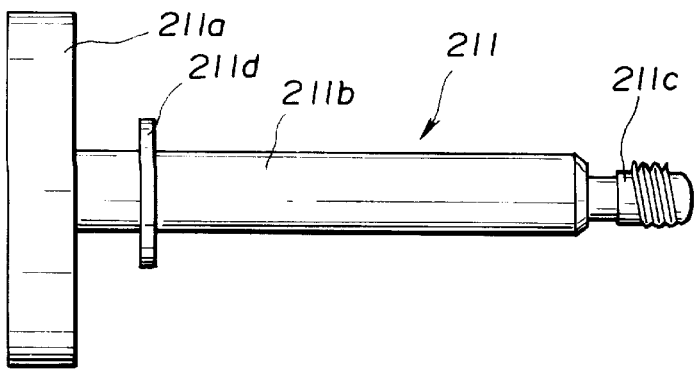

FIG.48
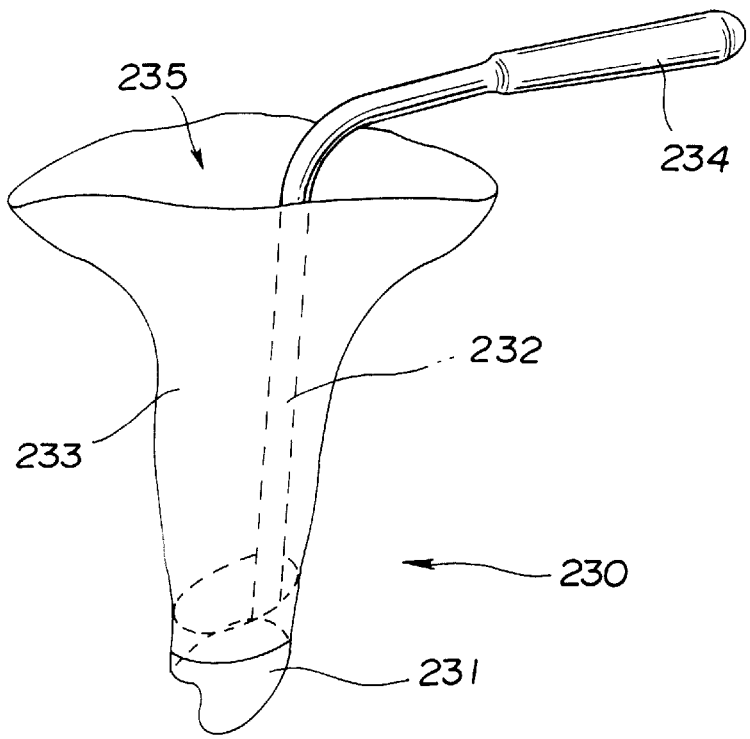
FIG.49A FIG.49B
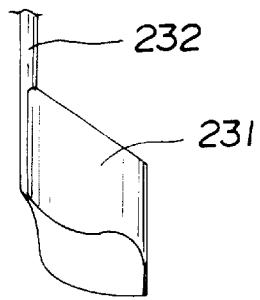 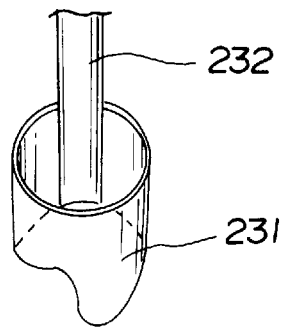
FIG.49C FIG.49D
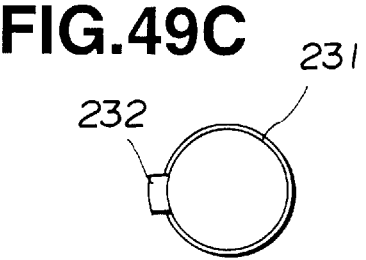 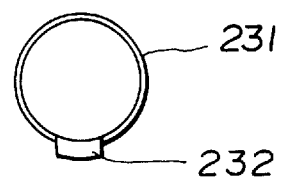

FIG.68 FIG.69
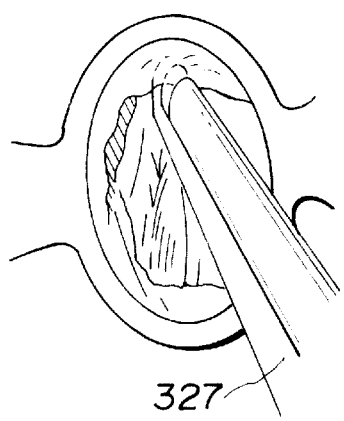
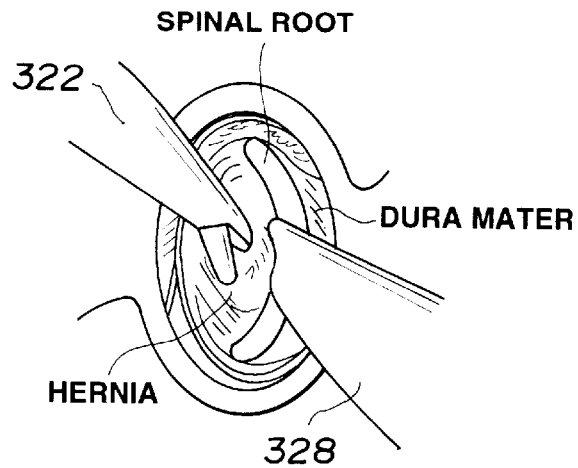
FIG.70
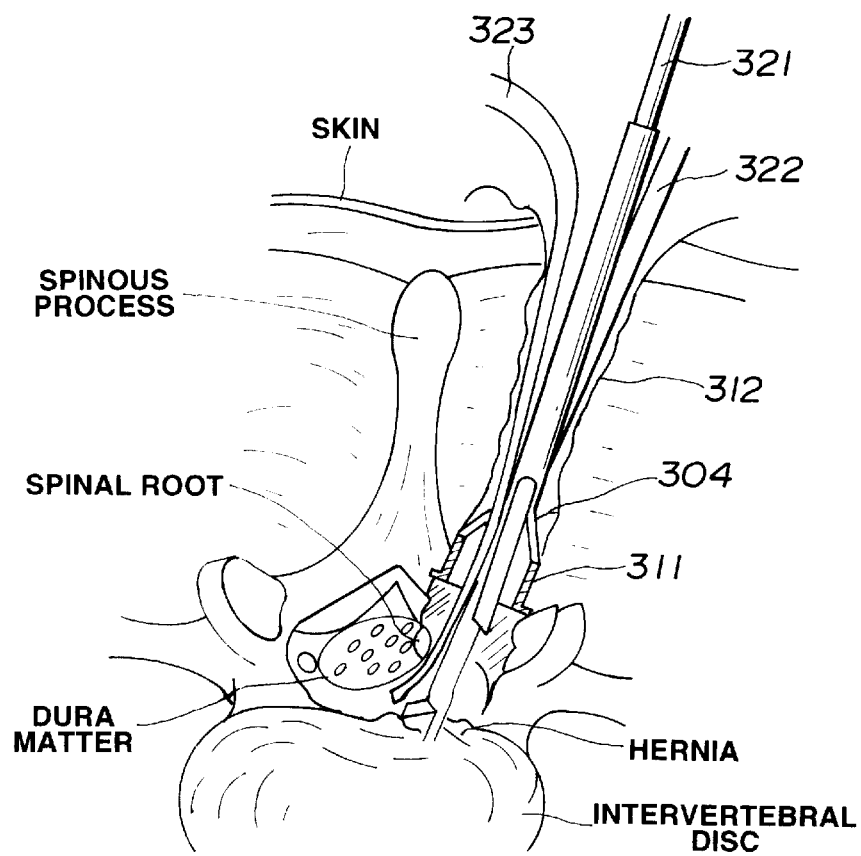

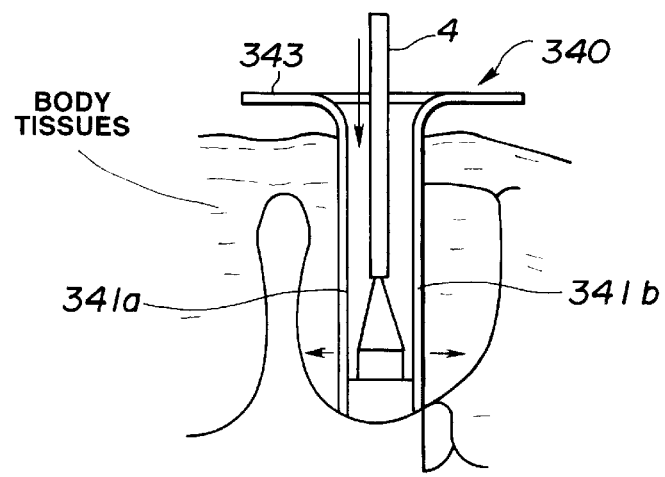
FIG.80
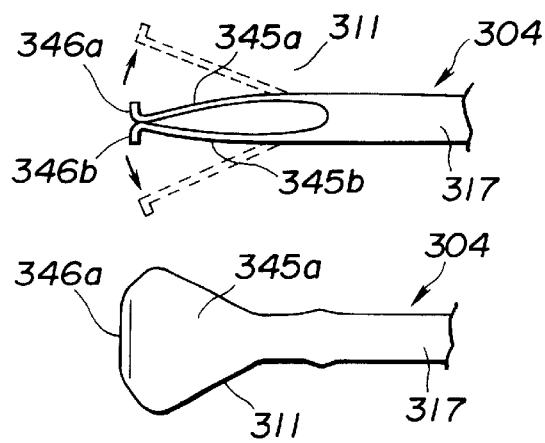
FIG.81A
FIG.81B
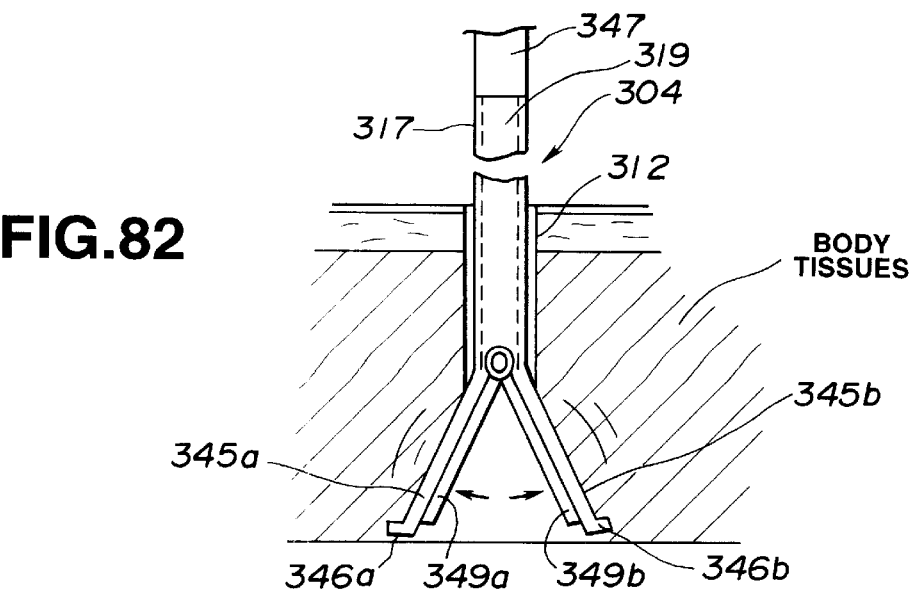
FIG.82

FIG.83A
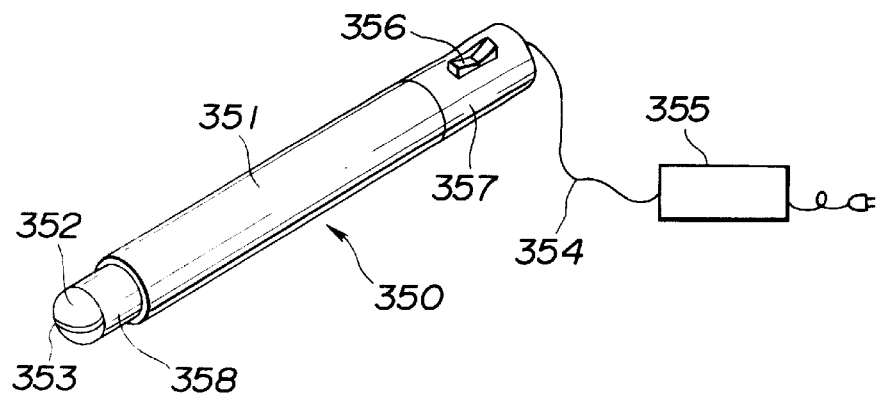
FIG.83B
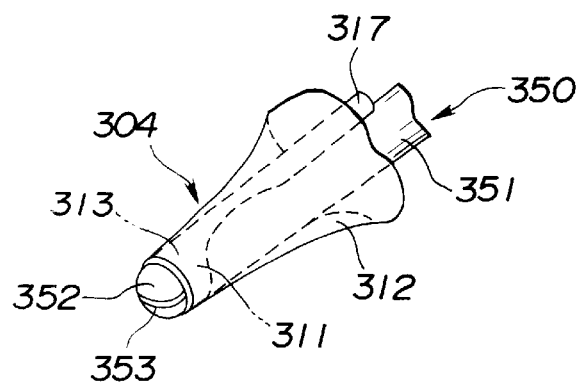
FIG.84A
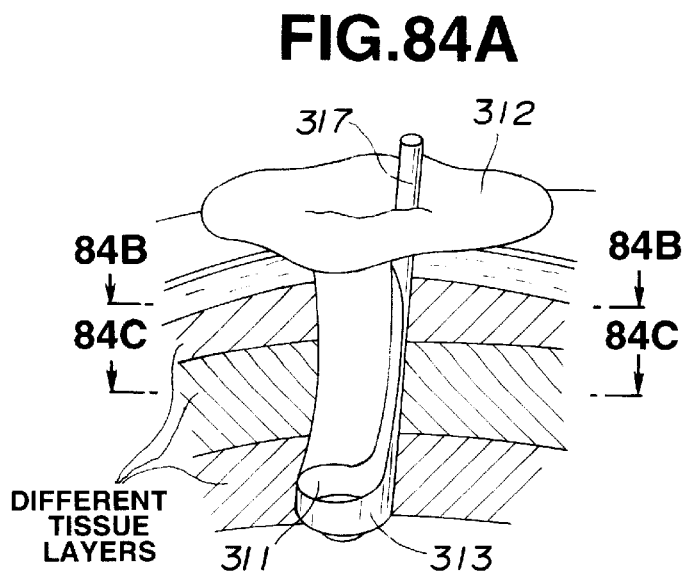
FIG.84B
FIG.84C
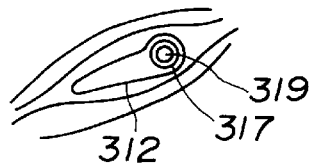

CAVITY RETAINING TOOL FOR BONE SURGERY, A CAVITY RETAINING TOOL FOR GENERAL SURGERY, AN ENDOSCOPIC SURGERY SYSTEM INVOLVING THE USE OF A CAVITY RETAINING TOOL, AND A PROCEDURE FOR SURGERY

BACKGROUND OF THE INVENTION

1. Field of the Invention

This invention relates to a cavity retaining tool for bone surgery and a cavity retaining tool for general surgery, to be used for retaining a cavity which acts as a working space during surgery.

2. Related Art Statement

Recently, endoscopic surgery has been widely applied for the operation of tissues in a cavity of the body. Such surgery, in contrast with the open surgery whereby a wide incision is made on the body system to reach a desired site and treat it, is advantageous in that it allows the operator to insert operation tools through a smaller incision to reach a desired site in a body cavity and treat it, or that it allows a low invasive operation. It has been mentioned, however, that one of the problems inherent to endoscopic surgery is that it scarcely allows the operator to have a sufficiently wide field for operation.

Take as an example a routine operation for the removal of a herniated intervertebral disc of the vertebral column. A median incision is made dorsally to expose dorsal muscles. The dorsal muscles are cut, and are then separated with grasping forceps to expose lumbar vertebrae. Then, part of vertebral arches is removed to expose the ligamentum flavum which covers spinal roots. The ligamentum flavum is cut, the underlying dura mater is put aside to one side, and the bulged portion of the disc or the herniated disc beneath the dura mater is removed. This commonly undertaken dorsal approach consisting of making a median incision and separating dorsal muscles forcibly with forceps requires wide incision of lumbosacral muscles, separation of those muscles from bones, and long and forcible displacement of the muscles from their natural insertions during surgery. Accordingly, it has been said that the patient often develops low-back pain after surgery or suffer irreversible injuries in dorsal muscles due to forced separation of them during surgery.

To meet such situations, the specification described in U.S. Pat. No. 5,313,962 proposed a procedure for the operation of vertebrae under laparoscopic monitoring. The method consists of pulling apart the peritoneum under laparoscopic monitoring, making a cavity by inflation of a gas to push aside adjacent organs, and inserting tools into the cavity for the surgical treatment of a desired vertebral body. The specification of U.S. Pat. No. 5,439,464 proposed an alternative procedure involving a dorsal approach. The method consists of introducing a plurality of cannulae from the back of the patient into the tissues around a desired vertebra, injecting saline through one of the cannulae into the tissues, applying a pressure through the saline to produce a cavity which serves as a working space, and inserting a rigid-tube mirror and treatment tools through other cannulae into the cavity to make a surgical operation under endoscopic monitoring.

The routine operation for a herniated intervertebral disc or the so-called open surgery which consists of incising the dorsal skin, exposing dorsal muscles, and separating the muscles with grasping forceps, thereby to expose desired vertebrae, is problematic in that it gives a great damage to dorsal muscles through forced separation, and causes irreversible injuries in those dorsal muscles. In addition, the injuries inflicted on the muscles through incision itself have been said to be also serious.

The operative procedure disclosed in the specification of U.S. Pat. No. 5,313,962 involving endoscopic surgery requires a large number of treatment tools including grasping forceps for rejection of nearby organs because, with this procedure, operation proceeds while adjacent organs are being rejected by force. Thus, the work involved in the rejection becomes very complicated. In addition, because organs such as intestines and blood vessels are ready to move, and hence, if rejection force is not sufficient, they will move into the work space to disturb the visibility of the space, or suffer damages themselves in the presence of treatment tools left in the space. This is particularly true when operation proceeds ventrally towards lumbar vertebrae, because there aorta and inferior vena cava run on the frontal aspect of the lumbar vertebrae, which requires utmost care and high degree skill from the operator.

The technique described in the specification of U.S. Pat. No. 5,439,464 and involving the use of a plurality of cannulae inflict relatively less damages to dorsal muscles which may occur as a result of incision or forcible rejection, but it is far from satisfactory because it will not allow a sufficient space for vision and work.

Conventionally surgical tools having a blunt end like a swab are used to bluntly strip organs of their attachment. Such surgery tools with a blunt end have a tip wrapped with cotton, absorbs therewith liquids like blood in a body cavity, and harden over time. Hence, they must be replaced during surgery because the tip surface becomes impracticably hard.

As a remedy for such inconvenience, the specification of U.S. Pat. No. 3,935,863 introduces a technique which consists of providing detachment tools with a suction property, thereby to prevent the tip from hardening. Alternatively, the specification of U.S. Pat. No. 5,310,406 proposes a technique in which the detachment tool itself, in place of a suction tube, is allowed to absorb blood and saline accumulated in a body cavity.

True, by the techniques disclosed in the specifications of U.S. Pat. Nos. 3,935,863 and 5,310,406, it is possible to absorb blood and saline in a body cavity. These techniques, however, being dependent on the use of sponge for absorption of liquids and blood, do not allow a sufficient supply of liquids into the body cavity as desired. Thus, when the body cavity must be washed with a liquid, it is necessary to insert a forceps for liquid supply into the body cavity, which requires replacement of another forceps in use with the forceps for liquid supply.

Further, if the work for detachment leads to damages of a vessel and causes it to bleed, an electrode for hemostasis must be inserted into the body cavity.

OBJECTS AND SUMMARY OF THE INVENTION

The first object of this invention is to provide a cavity-retaining tool for bone surgery which allows the operator to make an operation on bones such as vertebrae in a less invasive manner under a sufficiently wide visual field with a visibility-aiding instrument without resorting to rejection and detachment of adjacent organs and therefore without being concerned about damages inadvertently inflicted upon those organs.

The second object of this invention is to provide a cavity-retaining tool for bone surgery which will not require a high degree skill from the operator or rather allow him to make an operation in a simplified manner.

The third object of this invention is to provide a cavity-retaining tool for general surgery which allows the operator to make an operation in a less invasive manner under a sufficiently wide field for vision and work, in spite of its requiring only minimal rejection and detachment of adjacent organs.

The fourth object of this invention is to provide a multi-functional forceps which is produced after a detachment tool for surgery has been provided with a property to expel/absorb liquid, and hence which alone is capable of bluntly detaching adjacent organs, and of expelling or absorbing liquid.

Briefly, the cavity-retaining tool for bone surgery of this invention comprises: a sheath for retaining a cavity which is inserted into the body system to form a cavity there to serve as a space for bone surgery; a channel for treatment which is attached to the cavity-retaining sheath, and serves for guiding treatment tools necessary for the treatment of bones in that work space; an observation means which is attached to the cavity-retaining sheath, and serves as a means by which to observe the treatment being undertaken in the work space for bone surgery; and a joining means which is attached to the tip of the cavity-retaining sheath, and serves for joining the tip of the cavity-retaining sheath to the surface of a bone. Further, the cavity-retaining tool for general surgery comprises a cavity-retaining means which serves for retaining a cavity in the body for operation works, and a soft cylinder member which communicates with the cavity retained by the cavity-retaining means, thereby interconnecting the cavity with the space outside the body. Still further, the endoscopic surgery system involving the use of a cavity-retaining tool comprises a cavity-retaining means to retain a cavity in the body system, and at least one port which communicates with the cavity, so that interconnection between the port and the cavity is established within the body.

BRIEF DESCRIPTION OF THE DRAWINGS

FIGS. 1–9 refer to the first embodiment of this invention:

FIG. 1 gives a perspective view of disintegrated parts constituting a cavity-retaining tool for bone surgery;

FIG. 2A gives a longitudinal cross-section of a cavity-retaining sheath,

FIG. 2B gives a sectional view along the line 2B—2B in FIG. 2A;

FIG. 2C gives a flat view of the tip of the cavity-retaining sheath;

FIG. 3 gives one step necessary for the use of the cavity-retaining sheath for bone surgery;

FIG. 4 gives a second step necessary for the proper use of the cavity-retaining tool for bone surgery;

FIG. 5 gives a third step necessary for the proper use of the cavity-retaining tool for bone surgery;

FIG. 6 gives a fourth step necessary for the proper use of the cavity-retaining tool for bone surgery;

FIG. 6A shows how a scalpel is inserted into the intervetebral disc between the L5 and S1 vertebrae, to remove the fibrous ring.

FIG. 6B shows how the medullar core and intervertebral disc are removed with a curette;

FIG. 6C shows how the bones forming the bodies of L5 and S1 vertebrae are removed with a chisel;

FIG. 6D gives a view after a bone graft has been implanted into the cavity prepared in the vertebral body, and fixed in place, thereby completing ventral implanting;

FIG. 7 gives an outline of the anatomy of the vertebral column and aorta and inferior vena cava;

FIG. 8 illustrates how the cavity-retaining tool for bone surgery can be used in another way; and FIG. 9 illustrates how, in still another way, the sheath is fitted in place to a bone and fixed there.

FIGS. 11 and 12 refer to the second embodiment of this invention:

FIG. 12 illustrates how the two sheaths are put into use.

FIG. 14 shows a sheath used in the third embodiment:

FIG. 15 gives a perspective view of the tip of a sheath; and

FIG. 16 illustrates how the sheath is put into use.

FIG. 17 gives a perspective view of the tip of a sheath; and

FIG. 18 illustrates how the sheath is put into use.

FIG. 19 refers to the sixth embodiment of this invention:

FIG. 20 refers to the seventh embodiment of this invention:

FIG. 21 gives a sectional view of a sheath; and

FIG. 22 gives a sectional view of another sheath.

FIG. 23 gives a perspective view illustrating a sheath and a core needle;

FIG. 24 shows how the sheath is put into use; and

FIG. 25 shows how the sheath is immobilized.

FIG. 26 illustrates a sheath and an endoscope; and

FIG. 27 gives a perspective view of the tip of the sheath.

FIGS. 28–45 refer to the eleventh embodiment of this invention:

FIG. 28 illustrates how a system comprising an implant guide sheath is used;

FIG. 29 illustrates how the cap of an outer sheath is attached to the outer sheath;

FIG. 30 gives a lateral view of a drill;

FIG. 31A illustrates an intervetebral space opener;

FIG. 31B gives an enlarged view of an opening plug;

FIG. 32 gives a lateral view of a reamer;

FIG. 33 gives a lateral view of a bone tap;

FIG. 34 gives a lateral view of an implant driver; and

FIG. 35 illustrates an implant;

FIGS. 36–45 give a sequence of steps necessary for the proper use of the cavity-retaining tool for bone surgery;

FIG. 36 illustrates how a vertebral body to be treated and its surrounds are exposed for treatment;

FIG. 37 illustrates how an outer sheath is closely attached to vertebral bodies to be fixed there;

FIG. 38 illustrates how an intervetebral disc is drilled to produce a hole into which an implant is to be embedded;

FIG. 39 illustrates how the medullar nucleus and fibrous ring are removed from the hole prepared in the body of the intervetebral disc;

FIG. 41 illustrates how the treatment practiced in the work space within the sheath is monitored;

FIG. 42 illustrates how the hole is finished with a reamer;

FIG. 45 illustrates how implants have been embedded into a vertebral body.

FIG. 46 gives a perspective view of the tip of an outer sheath; and

FIG. 47 illustrates how a cavity-retaining tool for bone surgery is used.

FIGS. 48–53 refer to the thirteenth embodiment of this invention:

FIG. 48 gives an overview of a sheath for surgery;

FIG. 49 illustrates how the tip of a cavity-retaining segment of the sheath for surgery is shaped:

FIG. 49A illustrates how the tip of a cavity-retaining segment to come into contact with a spinous process is shaped; and FIG. 49B illustrates how the tip of a cavity-retaining segment to come into contact with a vertebral arch is shaped;

FIGS. 49C and 49D give end views of the tip of the cavity-retaining segment.

FIG. 50 gives a fifth step necessary for the proper use of a sheath for surgery:

FIG. 51 illustrates how a cavity for surgery is retained and treatment is performed in it;

FIG. 52 illustrates how a dilator is slid over a guide needle which has penetrated through a soft cylinder member of the sheath for surgery; and FIG. 53 illustrates how a trocar is inserted into the soft cylinder sheet member of the sheath for surgery.

FIGS. 55 and 56 refer to the fifteenth embodiment of this invention:

FIG. 55 illustrates how the tip of the cavity-retaining segment of a sheath for surgery is constructed;

FIG. 56 illustrates how the cavity-retaining segment is expanded which is made of a strip member.

FIGS. 57–70 refer to the sixteenth embodiment of this invention:

FIG. 58 is an anatomical illustration showing a dorsal view of human spinal column;

FIG. 59 is an anatomical illustration showing a cross-section along the line 59—59 in FIG. 58;

FIG. 60 is an anatomical illustration showing how a dilator of the cavity-retaining system for surgery is inserted into the site to be treated;

FIG. 61 is an anatomical illustration showing how a soft cylinder of the cavity-retaining system for surgery is inserted into the site to be treated;

FIG. 62 is an anatomical illustration showing how a sheath for surgery is inserted through the soft cylinder of the cavity-retaining system for surgery down to the site to be treated;

FIG. 65 gives an endoscopic view of the cavity prepared around the site to be treated, which is retained by the cavity-retaining means of a sheath for surgery;

FIG. 66 illustrates a step wherein a cutting means of the cavity-retaining system for surgery is used;

FIG. 67 illustrates a second step wherein a cutting means of the cavity-retaining system for surgery is used;

FIG. 68 illustrates a third step wherein a cutting means of the cavity-retaining system for surgery is used;

FIG. 69 illustrates a fourth step wherein a cutting means of the cavity-retaining system for surgery is used; and FIG. 70 illustrates a fifth step wherein a cutting means of the cavity-retaining system for surgery is used.

FIG. 71 gives a perspective view of a version of the sheath for surgery;

FIG. 72 gives a perspective view of a second version of the sheath for surgery; and FIG. 73 gives a perspective view of a third version of the sheath for surgery FIGS. 74–76 refer to the eighteenth embodiment of this invention:

Figure 75A:
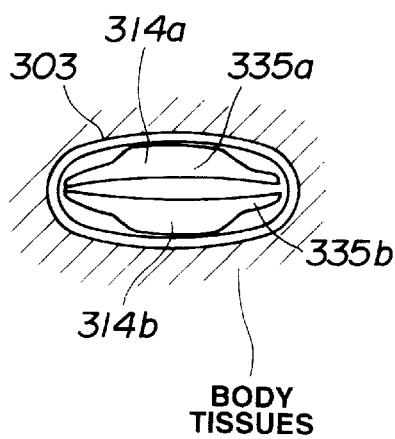
Figure 75B:
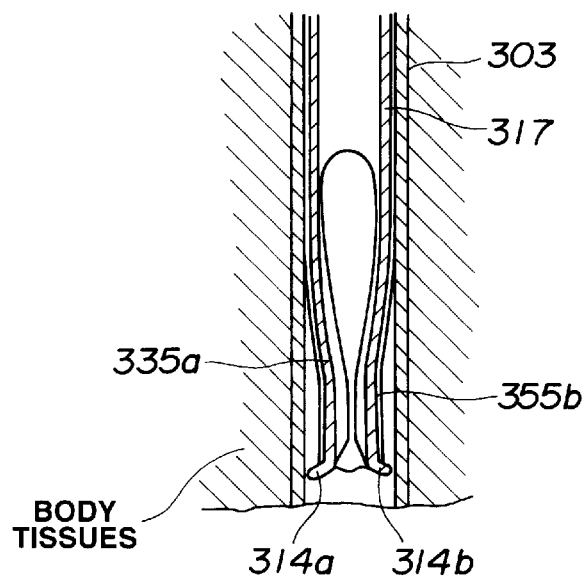
Figure 76:
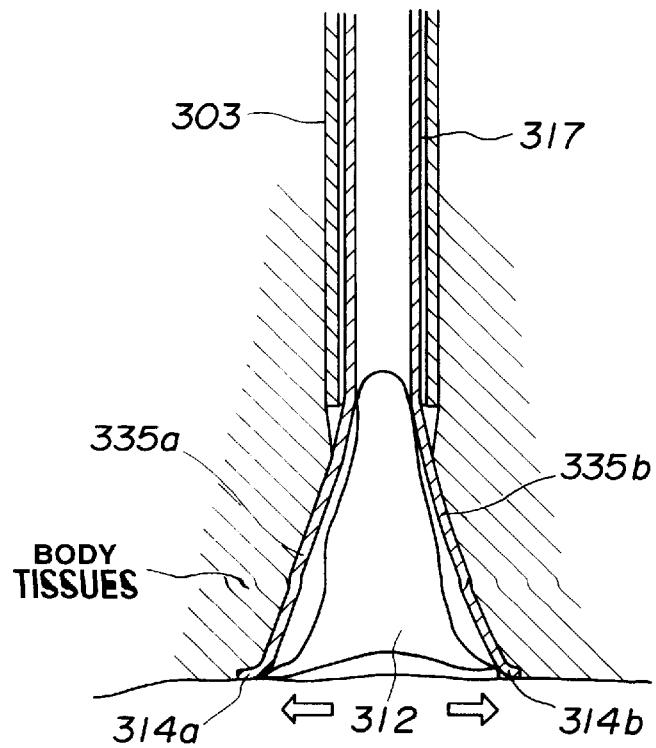

FIG. 75A gives a crosswise sectional view showing how the sheath for surgery is being introduced into bodily tissues;

FIG. 75B gives a lengthwise sectional view of the same sheath as depicted in FIG. 75A; and FIG. 76 gives a crosswise sectional view showing the sheath for surgery while it is introduced into body tissues.

Figure 77:
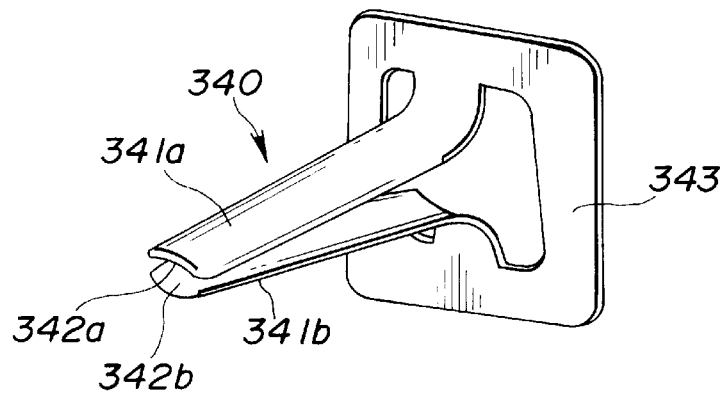
Figure 78:
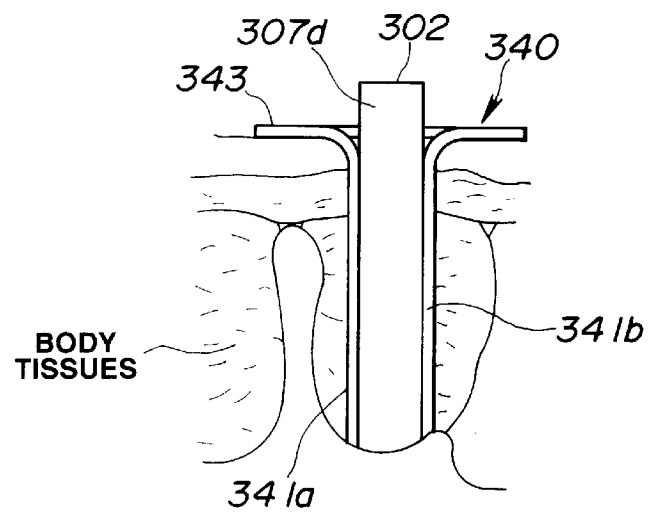
Figure 79:
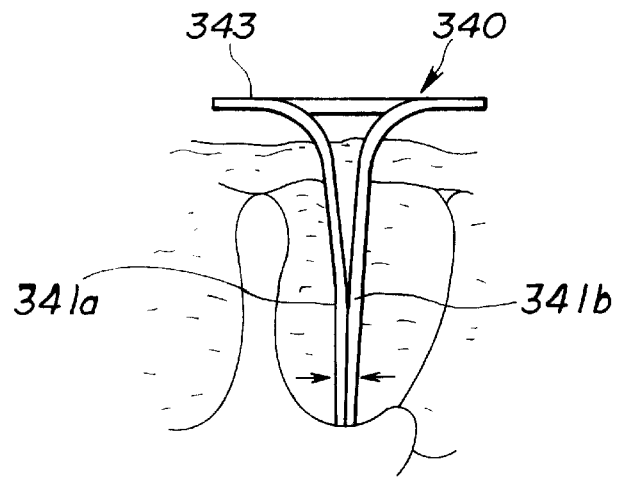

FIGS. 77–80 refer to the nineteenth embodiment of this invention:

FIG. 77 gives a perspective view of a guide means of a sheath for surgery;

FIG. 78 gives a sectional view showing how the guide means is used;

FIG. 79 gives a sectional view showing how the guide means is used; and

FIG. 80 gives a sectional view showing how the guide means is used.

FIGS. 81 and 82 refer to the twentieth embodiment of this invention:

FIG. 81A gives a lateral view of the tip of a sheath for surgery;

FIG. 81B gives a flat view of the tip of the same sheath for surgery; and

FIG. 82 illustrates how the sheath for surgery is introduced into body tissues.

FIGS. 83 and 84 refer to the twenty-first embodiment of this invention:

FIG. 83A gives a perspective view of a piercing tool;

FIG. 83B gives a perspective view showing how a sheath for surgery is attached to the piercing tool;

FIG. 84A gives a lateral view showing how the sheath for surgery is inserted into body tissues;

FIG. 84B gives a sectional view along the line 84B—84B in FIG. 84A; and

FIG. 84C gives a sectional view along the line 84C—84C in FIG. 84A.

Figure 85A:
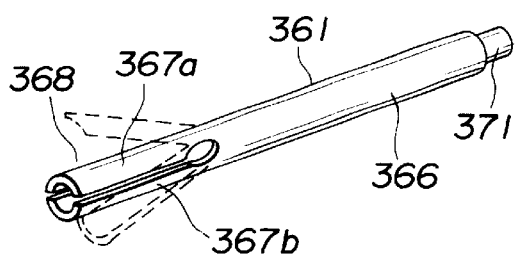
Figure 85B:
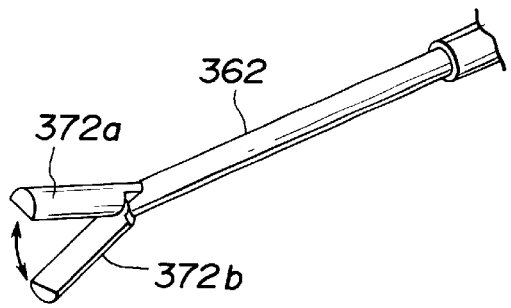
Figure 85C:
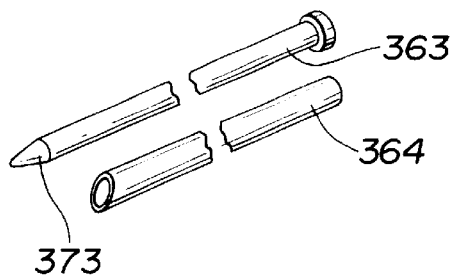
Figure 85D:
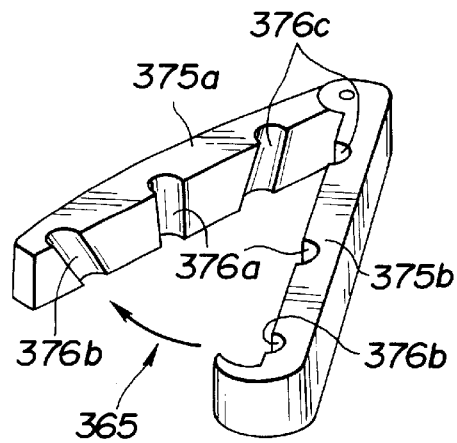
Figure 86:
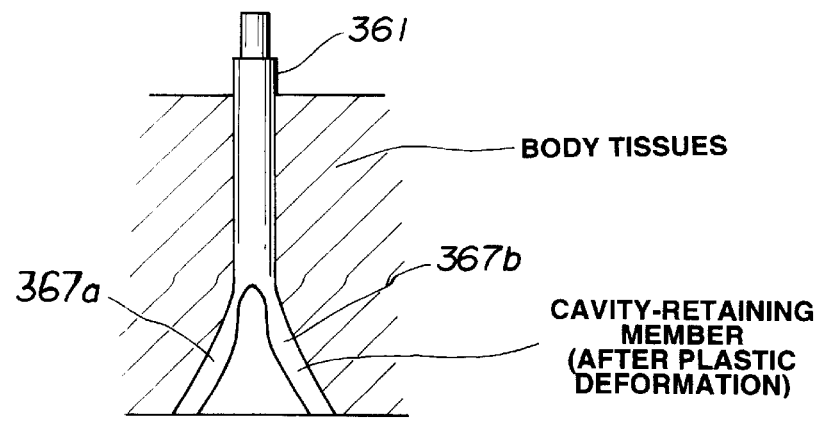
Figure 87:
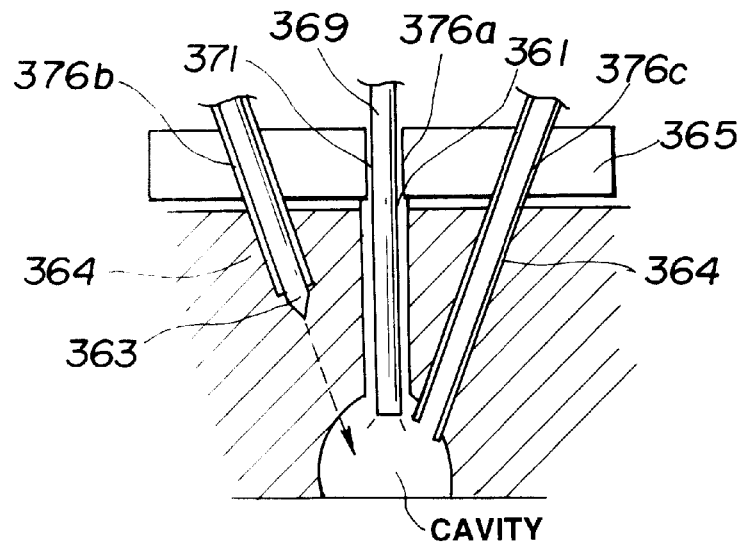

FIGS. 85–88 refer to the twenty-second embodiment of this invention:

FIG. 85 illustrates tools constituting a cavity-retaining system for surgery;

FIG. 85A illustrates a sheath for surgery;

FIG. 85B illustrates a cavity-expander;

FIG. 85C illustrates a core needle and a port;

FIG. 85D illustrates a port guide;

FIG. 86 illustrates how the sheath for surgery is left in body tissues;

FIG. 87 illustrates how surgery is practiced using the port guide; and

Figure 88:
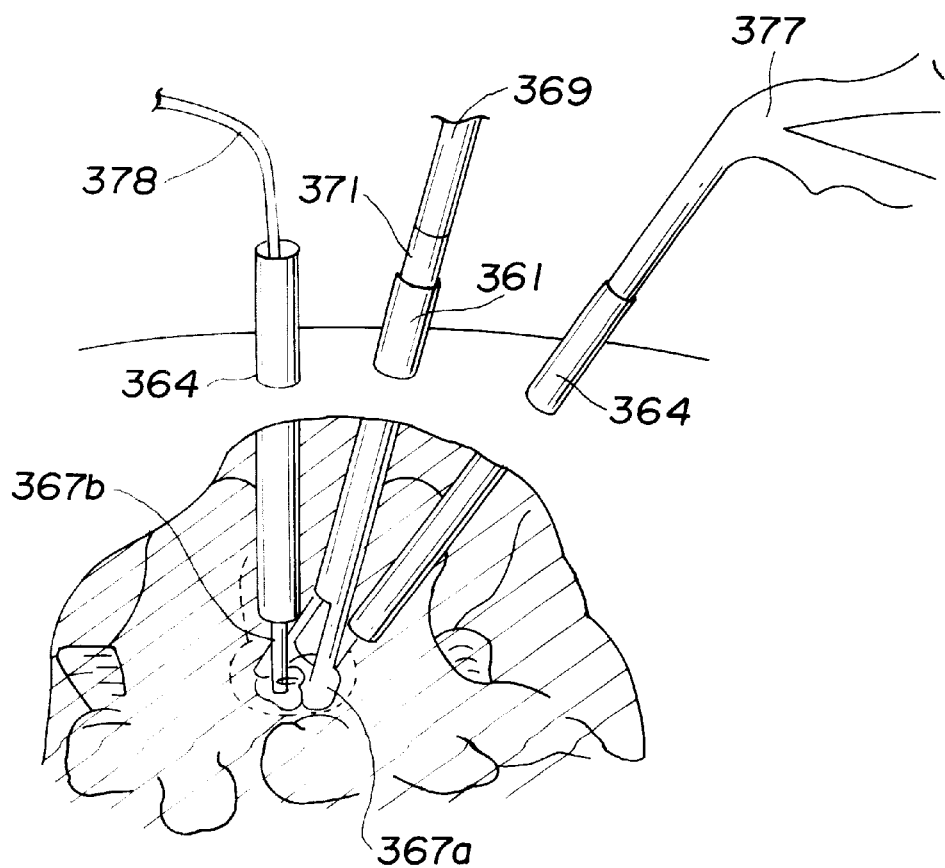

FIG. 88 gives an overview showing how surgery proceeds with the present system.

Figures 89A, 89B:
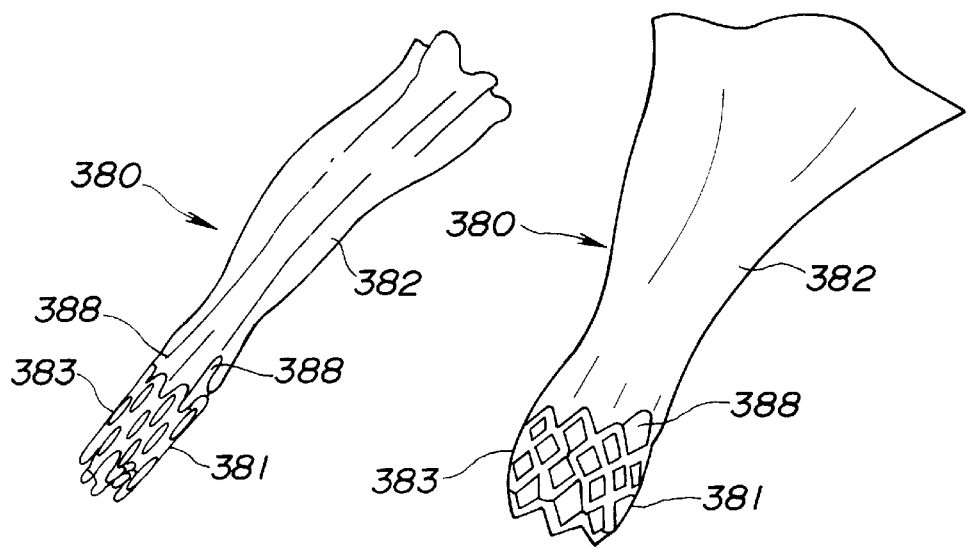
Figures 90A, 90B:
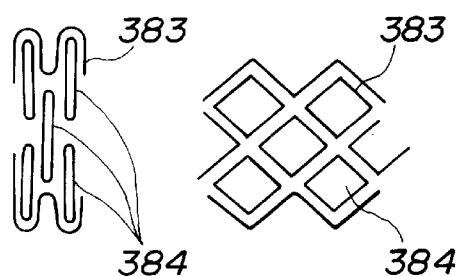
Figures 91A, 91B:
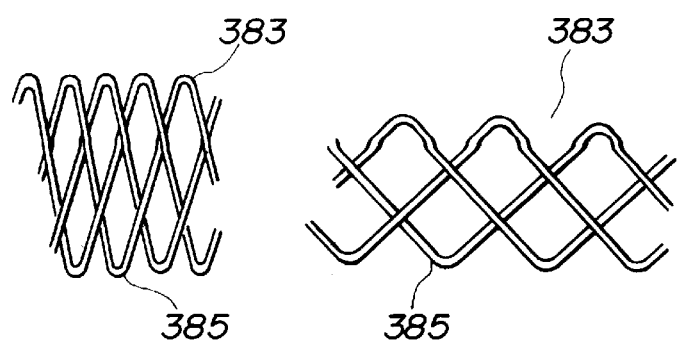
Figure 92A:
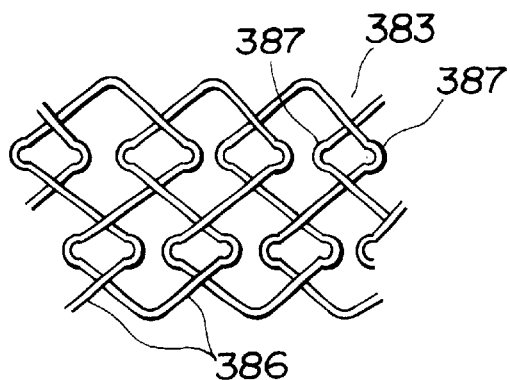
Figure 92B:
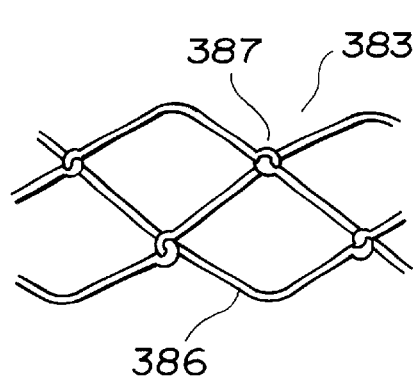
Figure 93A:
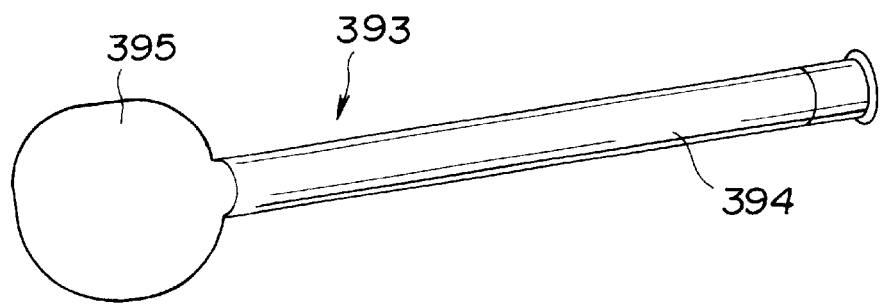
Figure 93B:
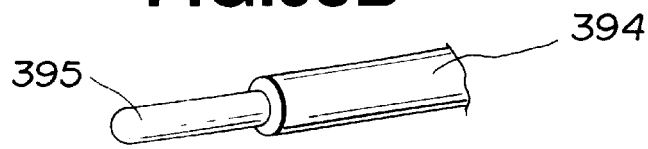
Figure 93C:
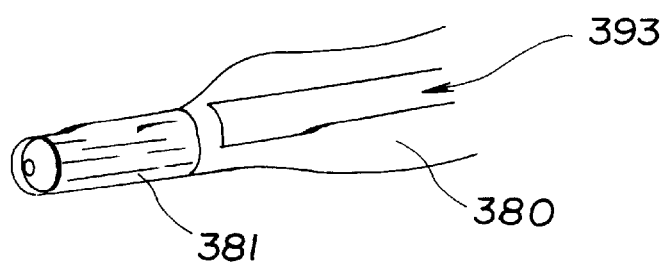
Figure 94A:
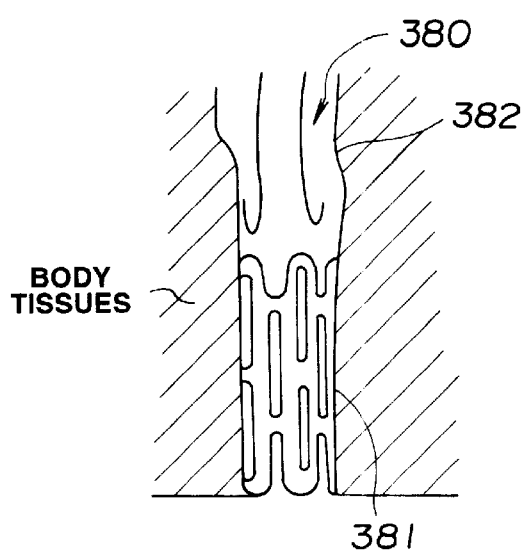
Figure 94B:
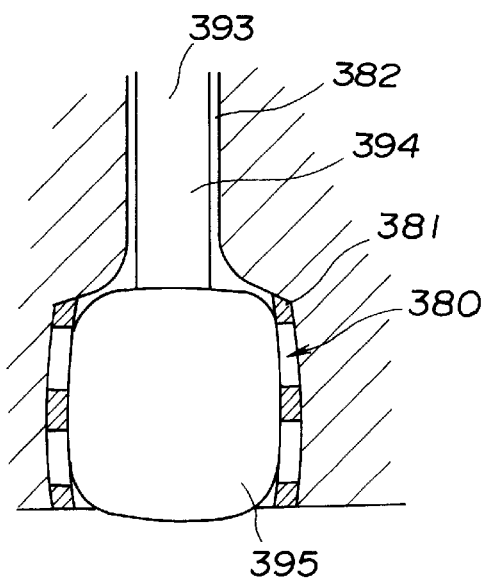
Figure 95:
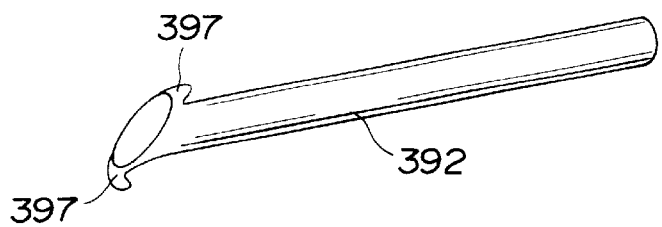
Figure 96:
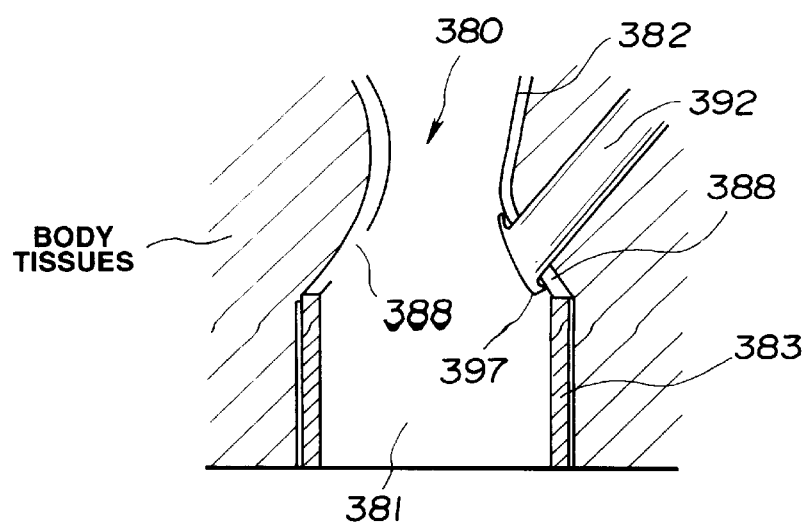
Figure 97:
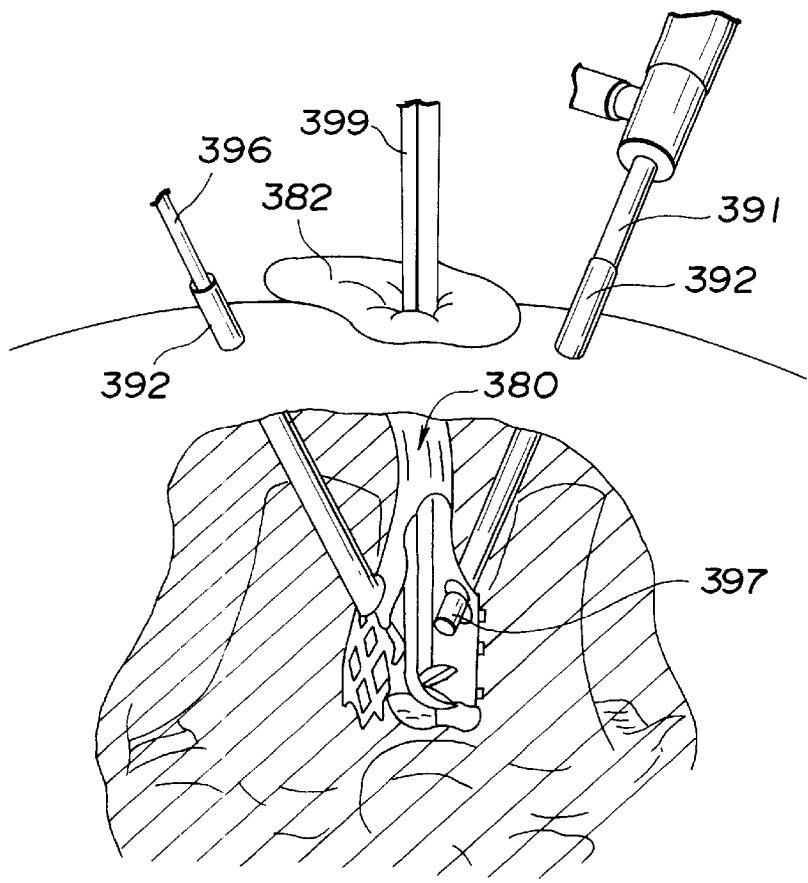
Figure 98:
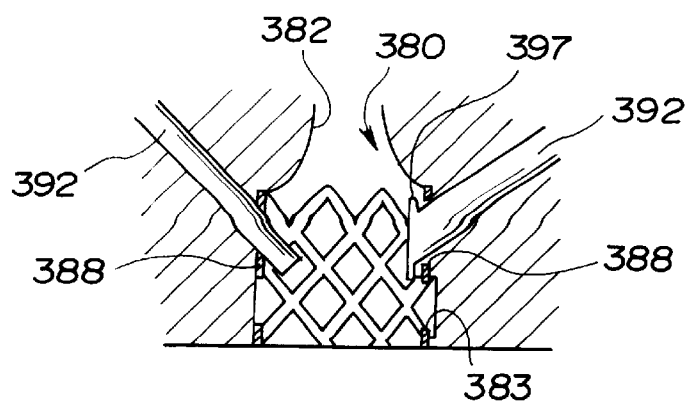
Figure 99:
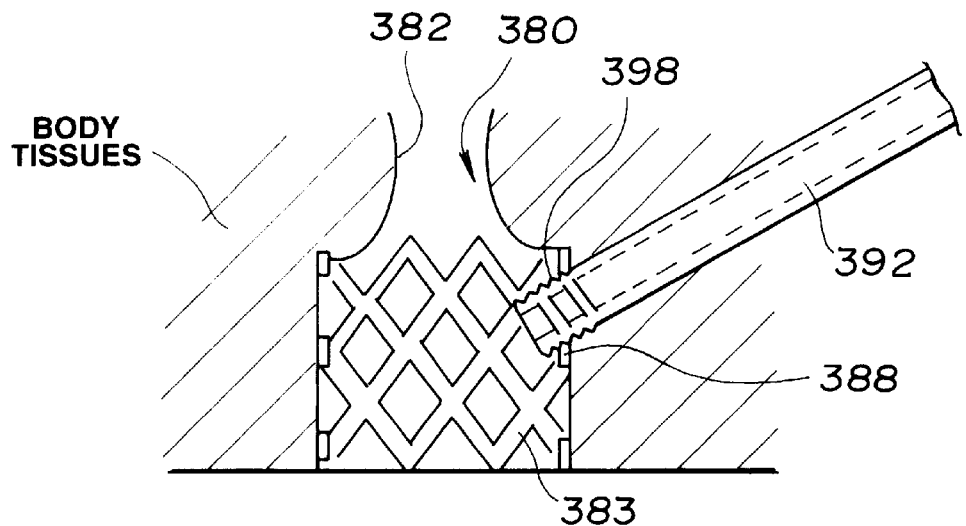
Figure 100:
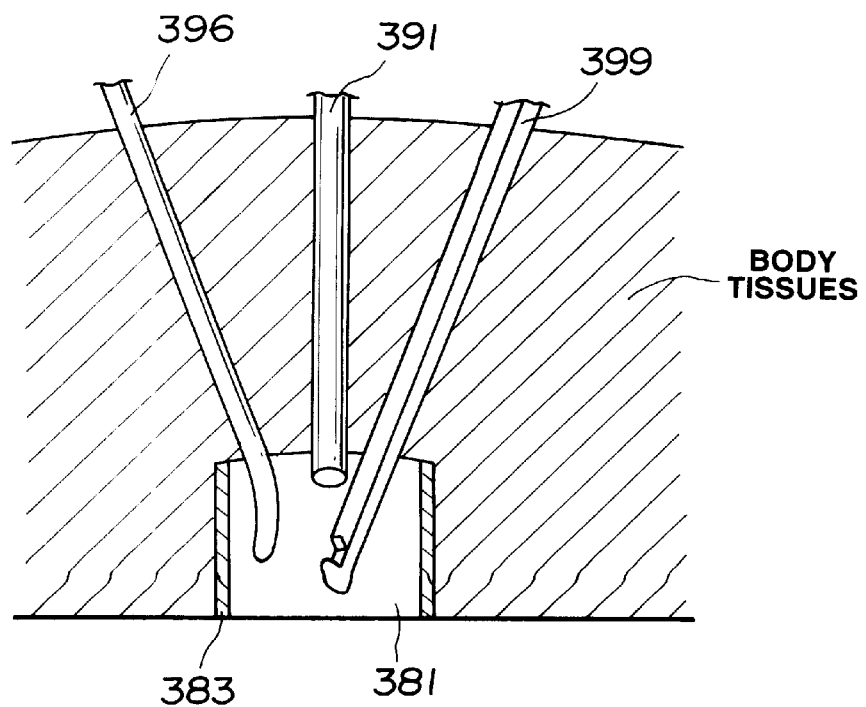

FIGS. 89–100 refer to the twenty-third embodiment of this invention:

FIG. 89 illustrates a sheath for surgery;

FIG. 89A gives a perspective view of the sheath for surgery for common use;

FIG. 89B gives a perspective view of the sheath for surgery expanded to produce a cavity;

FIG. 90 illustrates a version of ring segment constituting the sheath for surgery;

FIG. 90A illustrates how slit-like perforations are contracted;

FIG. 90B illustrates how slit-like perforations are extended;

FIG. 91 illustrates a second version of ring segment of the sheath for surgery;

FIG. 91A illustrates how knit cords are contracted;

FIG. 91B illustrates how knit cords are extended;

FIG. 92 illustrates a third version of ring segment of the sheath for surgery;

FIG. 92A illustrates how cords are contracted by disengaging joints at intersections;

FIG. 92B illustrates how cords are extended by forming joints with each other at intersections;

FIG. 93A gives a perspective view of a cavity-expander being expanded;

FIG. 93B gives a perspective view of a cavity-expander being contracted;

FIG. 93C gives a perspective view showing how the sheath for surgery is attached to the cavity expander;

FIG. 94A illustrates how the sheath for surgery is introduced into body tissues;

FIG. 94B illustrates how a balloon is inflated;

FIG. 95 gives a perspective view of the port;

FIG. 96 gives a sectional view showing how the sheath for surgery and the port are introduced into body tissues;

FIG. 97 illustrates how the sheath for surgery and port are introduced in body tissues to be of service for surgery;

FIG. 98 illustrates how the sheath for surgery and port are introduced in body tissues to be of service for surgery;

FIG. 99 illustrates how the sheath for surgery and port are introduced in body tissues to be of service for surgery and;

FIG. 100 illustrates how the sheath for surgery and port are introduced in body tissues to be of service for surgery.

Figure 101:
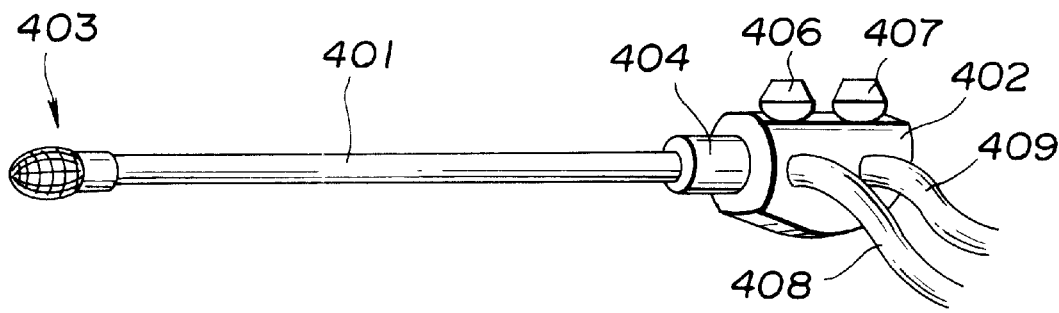
Figure 102A:
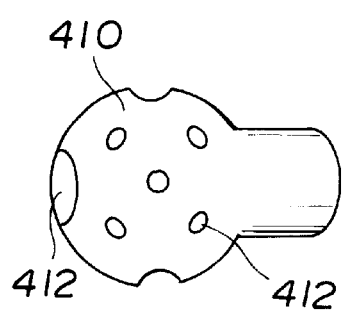
Figure 102B:
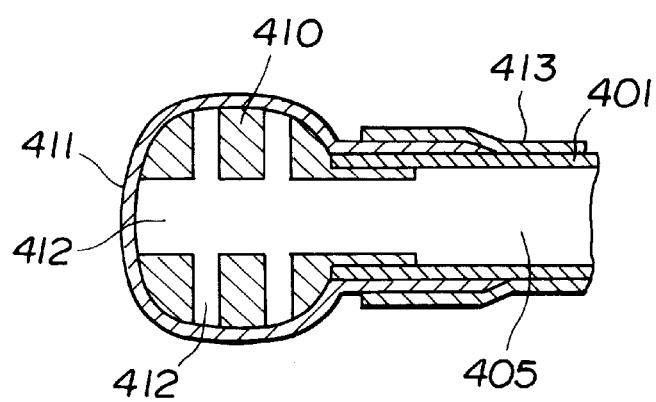

FIGS. 101–103 refer to the twenty-fourth embodiment of this invention:

FIG. 101 gives an overview of a detachment tool for surgery;

FIG. 102A gives an external view the elastic segment of a treatment tip;

FIG. 102B gives an sectional view of the tip of an insert and the treatment tip.

Figure 103A:
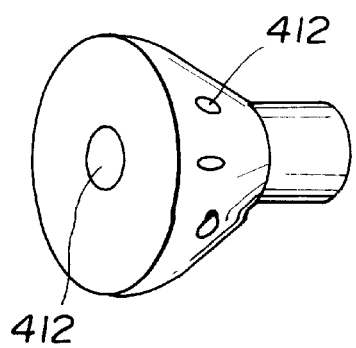

FIG. 103 illustrates modified forms of the elastic segment;

FIG. 103A illustrates a nearly conical form of elastic segment; and

Figure 103B:
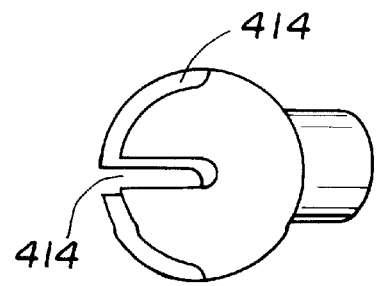

FIG. 103B illustrates a nearly spherical form of the elastic segment with grooves on its surface.

Figure 104:
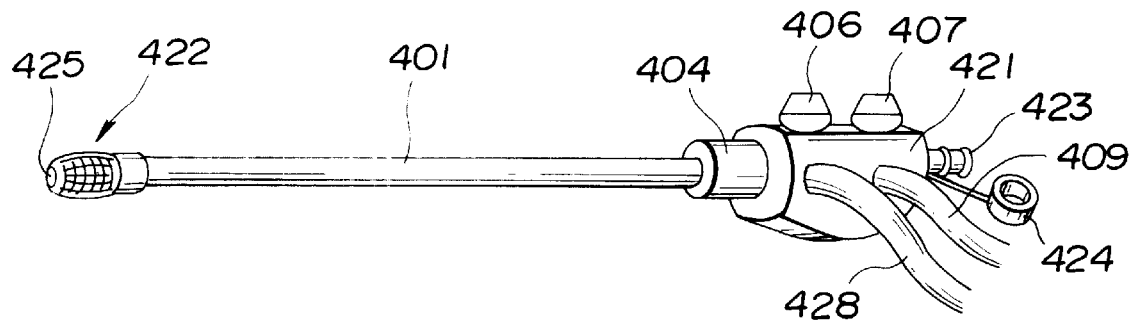
Figure 105:
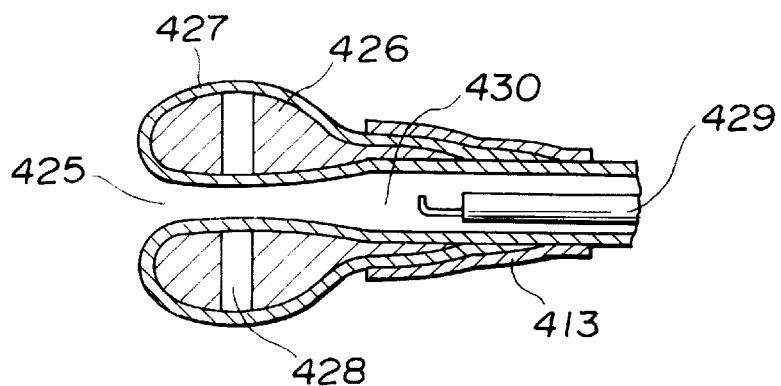

FIGS. 104–105 refer to the twenty-fifth embodiment of this invention:

FIG. 104 gives an overview of the detachment tool for surgery; and

FIG. 105 gives a sectional view of the tip of an insert and a treatment segment.

Figure 106:
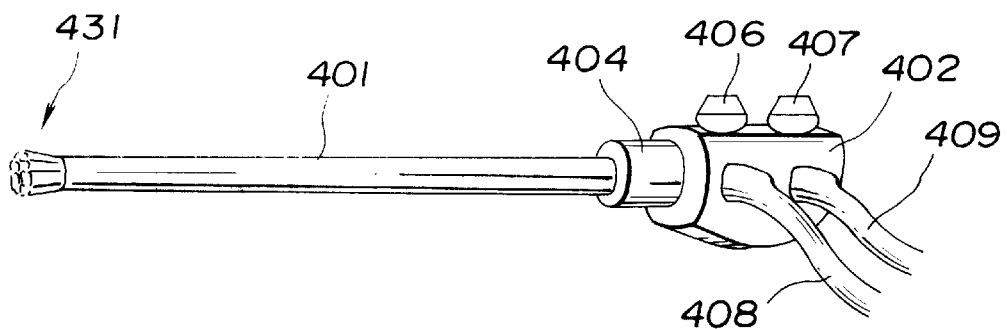
Figure 107A:
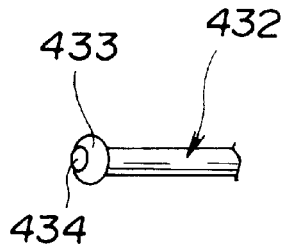
Figure 107B:
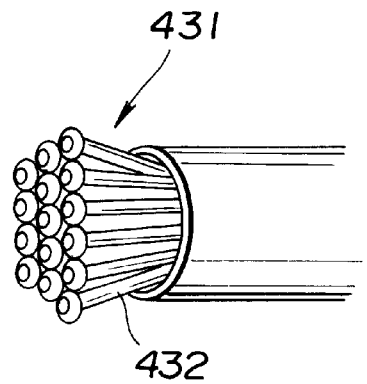
Figure 108:
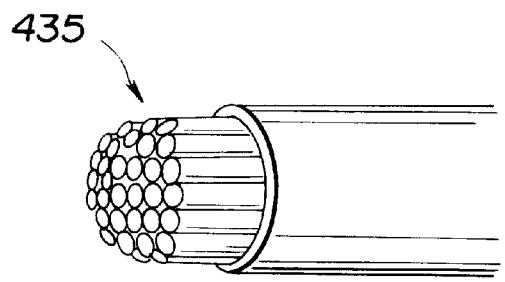

FIGS. 106–108 illustrate modified versions of the twenty-fourth embodiment of this invention:

FIG. 106 gives an overview of a detachment tool for surgery;

FIG. 107 illustrates the working tips of the detachment tool;

FIG. 107A gives a detailed view of the tip of a tube;

FIG. 107B illustrates how tubes are introduced into an insert; and

FIG. 108 illustrates a modified version of working tips.

Figure 109:
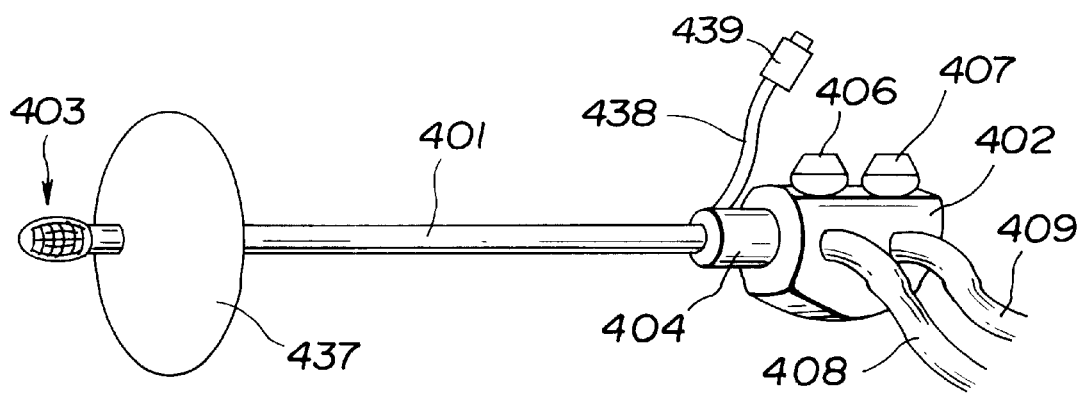

FIG. 109 gives an overview of a detachment tool for surgery of the twenty-sixth embodiment of this invention.

Figure 110:
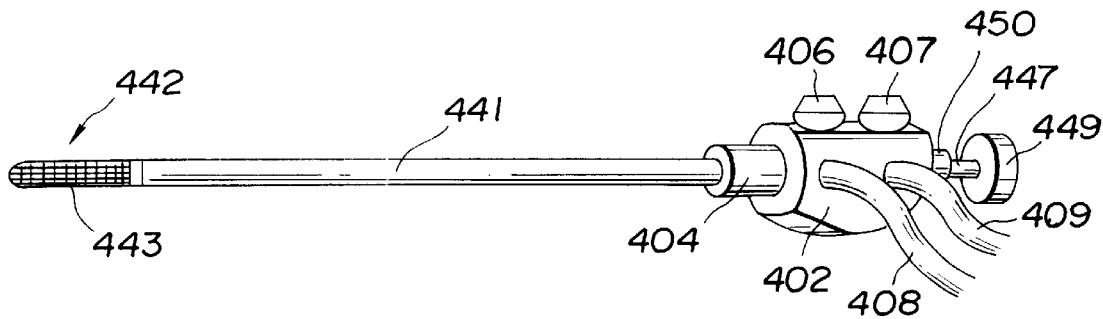
Figure 111A:
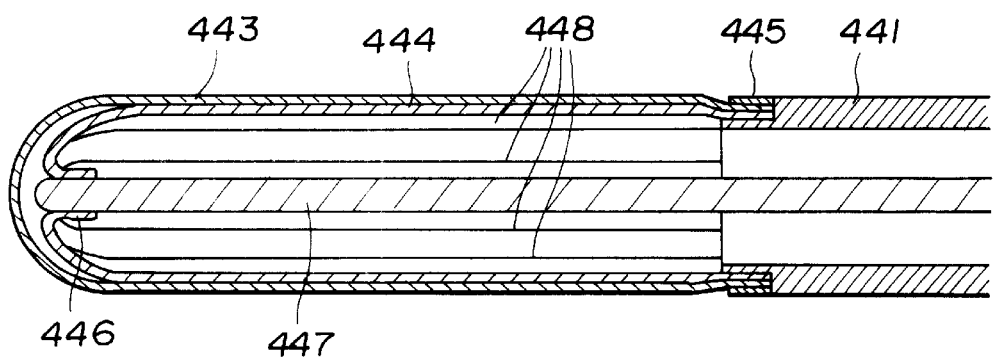
Figure 111B:
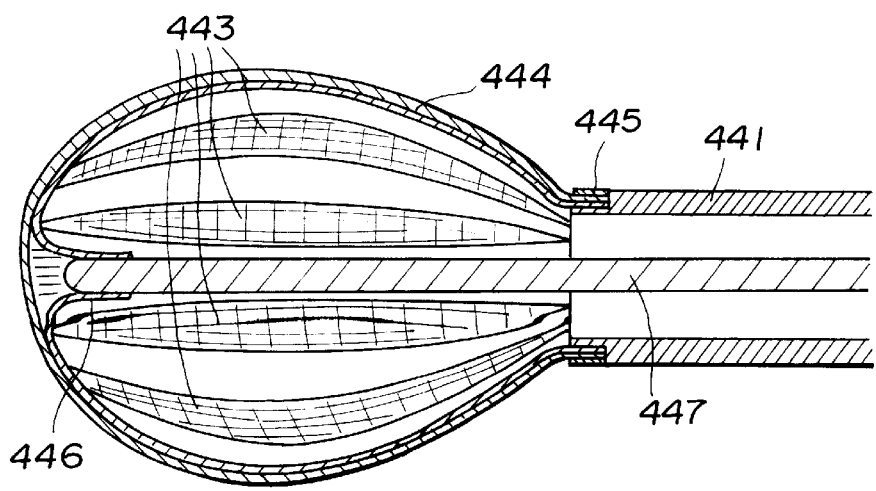
Figure 112A:
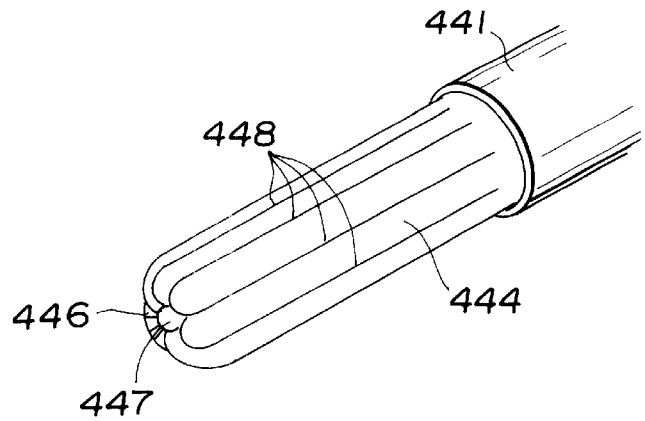

FIGS. 110–112 refer to the twenty-seventh embodiment of this invention:

FIG. 110 gives an overview of a detachment tool for surgery;

FIG. 111 gives a sectional view of a working tip;

FIG. 111A gives a sectional view showing how the working tip looks like when inserted;

FIG. 111B gives a sectional view showing how the working tip is expanded after being inserted;

FIG. 112 gives an external view of working tips exposed after being removed of a mesh;

FIG. 112A illustrates how working tips look like when inserted; and

Figure 112B:
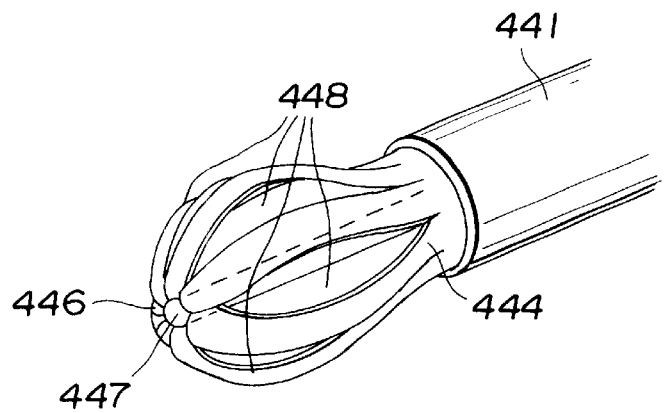

FIG. 112B illustrates how working tips are expanded after having been inserted.

Figure 113:
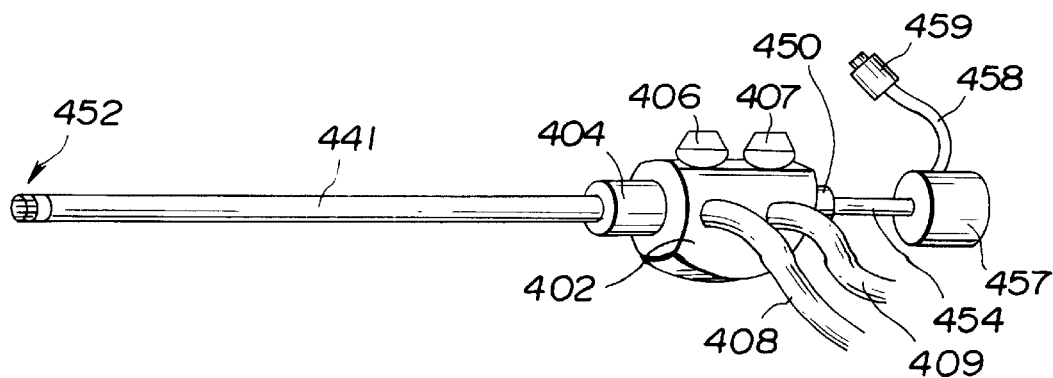
Figure 114:
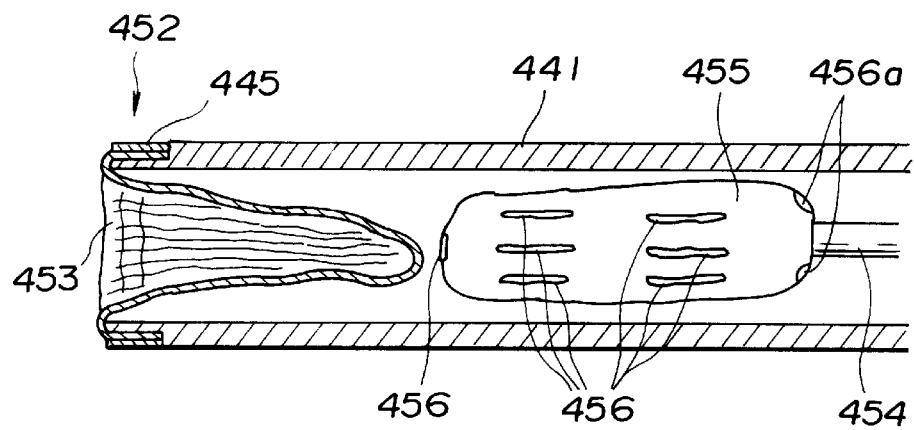
Figure 115:
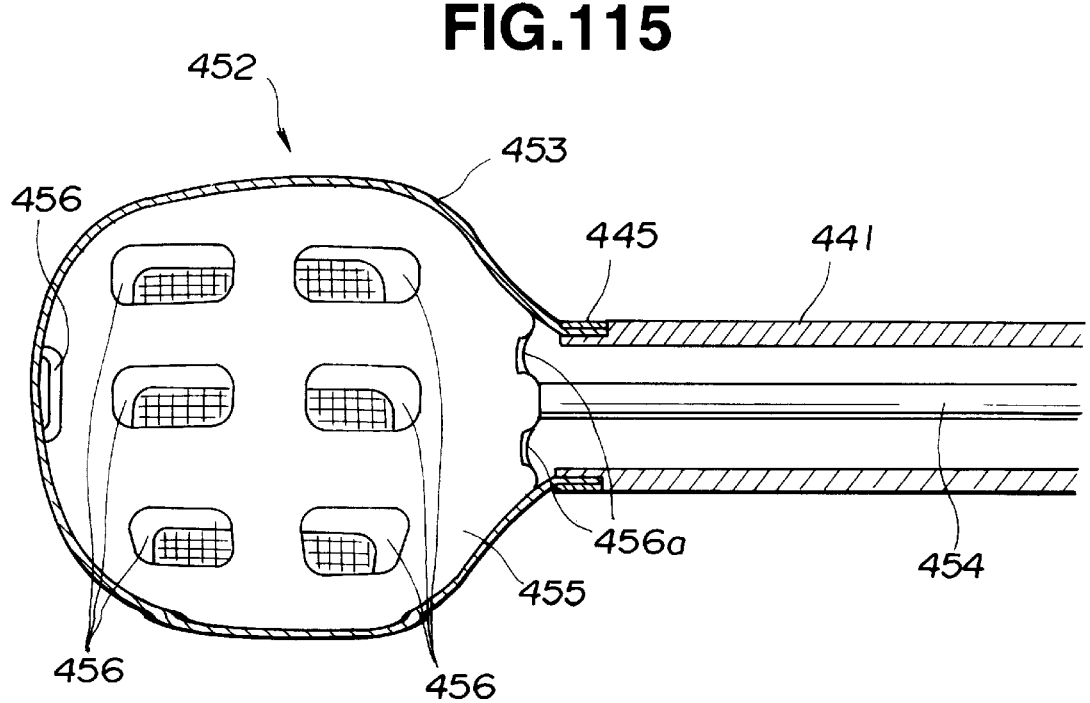

FIGS. 113 and 115 refer to the twenty-eighth embodiment of this invention:

FIG. 113 gives an overview of a detachment tool for surgery;

FIG. 114 gives a sectional view of a working tip before insertion; and

FIG. 115 gives a sectional view of a working tip after a mesh has been inflated.

Figure 116:
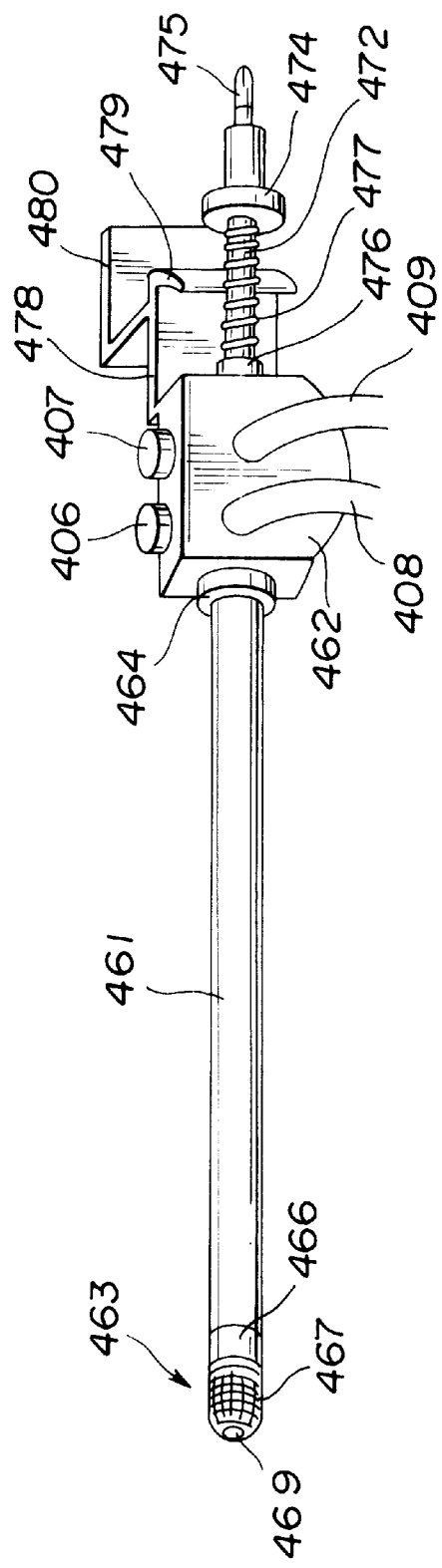
Figure 117:
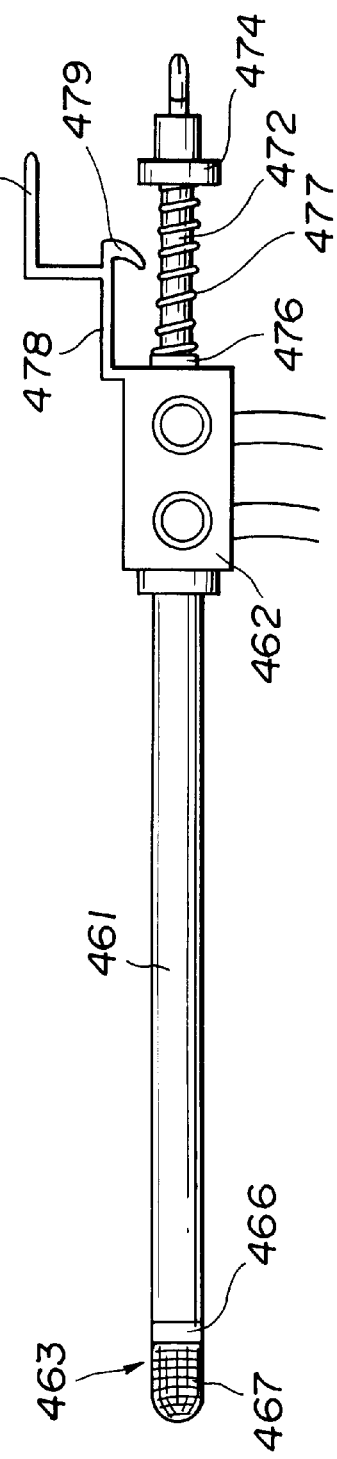
Figure 118:
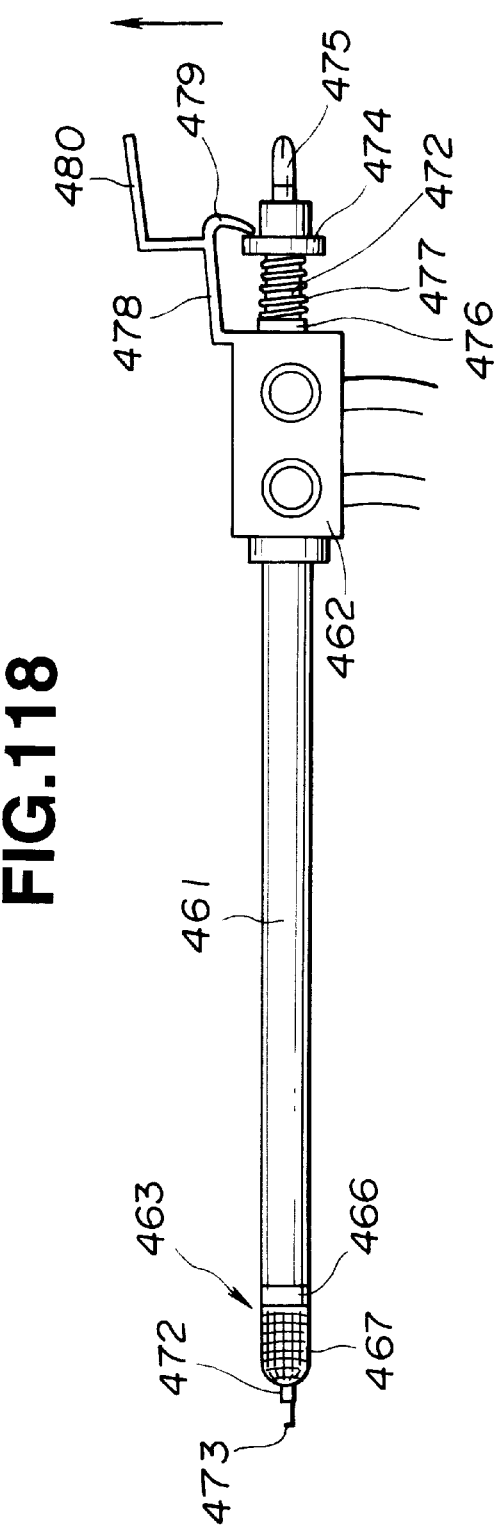
Figure 119:
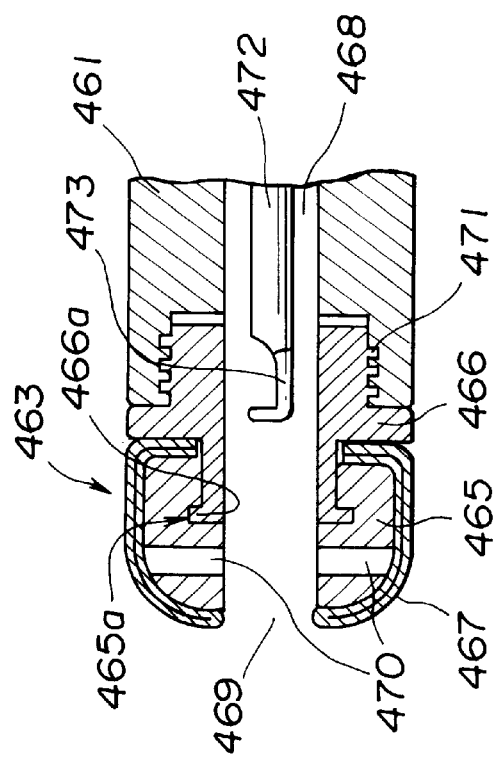

FIGS. 116–119 refer to the twenty-ninth embodiment of this invention:

FIG. 116 gives an overview of a detachment tool for surgery;

FIG. 117 illustrates the detachment tool whose insert receives an electrode within its space;

FIG. 118 illustrates the detachment tool of which the electrode protrudes from the tip of a treatment part; and FIG. 119 gives a sectional view of the working tip depicted in FIG. 117.

DETAILED DESCRIPTION OF THE PREFERRED EMBODIMENTS

The first embodiment of this invention will be described below with reference to FIGS. 1–9.

As seen from FIG. 1, a cavity-retaining tool for bone surgery of the first embodiment is provided with a sheath system for vertebral surgery which comprises a plurality of parts.

The system comprises a cavity-retaining sheath 1 to be introduced into body tissues, a mandrin for expansion (also referred to as a core needle) 2, a rod 3, an air-tight core cylinder 4, spikes 5, a plug for scope channel 6, and plugs for spike channel 7, and is further supplemented with a suction tube 8.

The sheath 1 is provided with a number of channels. One of them is a treatment channel 11 through which treatment tools pass. The treatment channel 11 exists as a straight passage formed in the very cavity of the sheath 1.

As seen from FIGS. 2A and 2B, the treatment channel 11 is a straight tunnel extending linearly from the top to bottom ends whose cross-section is circular in form. The front end of this treatment channel 11 forms a work space for bone surgery described later.

On the upper wall of the sheath 1 is implemented a scope channel 12 into which an endoscope will be introduced. The scope channel 12 has a slanting angle to the treatment channel 11 and is placed adjacent to the treatment channel 11. The front end opening of the scope channel 12 directly communicates, through the internal cavity of the sheath 1, with the treatment channel 11. The scope channel 12 is placed linearly with a small angle to the treatment channel 11 in such a way that its front end approaches the center of the treatment channel 11 and its base end stays increasingly away from the center of the treatment channel 11. The central axis of the scope channel 12 is apart from the central axis of the treatment channel 11 at the cross-section of the front end of sheath 1. This arrangement is chosen in order to prevent as far as possible an endoscope which will be introduced into the channel 12, from protruding into the space within the sheath 1.

As seen from FIG. 2A, the upper wall of the sheath 1 protrudes increasingly upward in accordance with the angle with which the scope channel 12 inclines. As seen from FIG. 2B, the protruded upper wall has its external surface, in cross-section, made as round as possible, or made free from any concavity, or at least made with a group of flat surfaces. Accordingly, the sheath 1 has a cross-section, at whatever level it may be cut, whose perimeter comprises a combination of convex surfaces, or, at worst, a combination of flat surfaces, and does not comprise any concave surfaces.

To the basic end of the sheath 1 is attached a flange. 13 which surrounds openings 11a and 12a which communicate with the treatment and scope channels 11 and 12, respectively. The opening 12a to communicate with the scope channel 12 has an O-ring 14 on its internal surface. The O-ring 14 acts both as a fixing means to fix, at any desired position, the optical tube 16 of a rigid endoscope, for example, of a laparoscope 15 which will be inserted through the ring, and as an air-tight means to helmetically seal the opening.

Figure 3A:
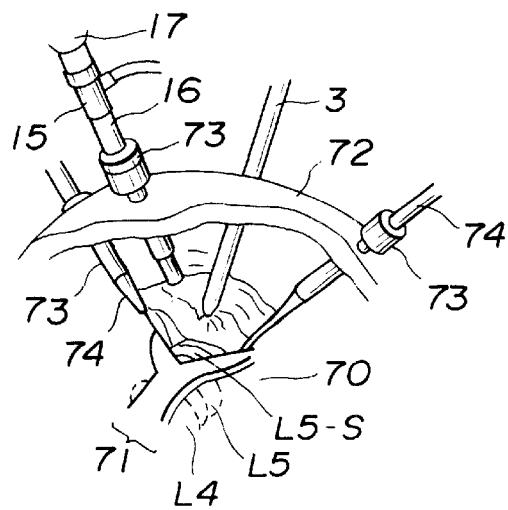
FIG. 3A gives a step where a trochar is inserted through the abdominal wall after a pneumoperitoneum has bee prepared.

As seen from FIG. 3A and others, the laparoscope 15 here concerned is adapted for direct vision, and has an optical tube 16 whose basic end is equipped with an eye-piece 17. The optical tube 16 and eye-piece 17 are arranged linearly, and this arrangement is commonly adopted by conventional laparoscopes available in the market.

The tip of the sheath 1 is so prepared as to fit the body of a vertebra which will be placed opposite to the sheath 1, and has a form close to that of the body of a vertebra. As seen from FIG. 2C, the tip of the sheath 1 has a curved surface. In addition, the tip of the sheath 1 has a taper 19 in profile in its internal rim so that the internal cavity expands outwards.

The tip of the sheath 1 is provided with a fitting means which allows the sheath 1 to fit to the body of a vertebra, and the sheath 1 is further provided with two spike channels 21 through which fixing means (also referred to as anchoring means) are passed to allow the sheath 1 to fix onto the body of a vertebra. The spike channels 21 are so constructed as to allow spikes 5 which act as a fixing means, to pass through them. The spike channels 21 are made of a pipe material, run through the internal wall of the sheath 1 down close to the tip, and are arranged on both sides of the scope channel 12, having their outlets opened at recessed places. The basic end of the spike channel 21 penetrates the wall surrounded with the flange 13 of the sheath 1 to open its mouth towards outside. The spike channels 21 of this embodiment are represented by the two channels displaced on one end of the sheath, or upwards in the cross-section of the sheath 1. The two spike channels 21 are arranged as represented in FIG. 2C so that they can correspond with the curvature of a vertebral body.

Further, on the internal rim of the tip of sheath 1 are prepared shelter ports 23 which are formed after part of the wall surrounding the tips of the spike channels has been removed. The front end of the spike channel 21 opens its mouth into this recessed alcove or the shelter port 23. In short, the spike channel 21 opens its front end into the recessed alcove formed in the wall of the sheath 1, and thereby communicates with the interval cavity of the sheath 1. Further, the spike channel 21 is so constructed in the wall of the sheath 1 so that the inner portion of the shelter port 23 comes into the visual field of an endoscope, and hence, things protruding from the tip of the spike channel 21 including the tip of the spike 5 can be seen in the internal cavity of the sheath 1 with the endoscope. Further , the internal surface of the taper 19 prepared at the tip of the sheath 1 also comes into the visual field of the endoscope, and can be watched through the endoscope.

The sheath 1 is provided, on both sides of the tip, with depressions 24 for rejected organs.

The sheath 1 is made of a resin which is permeable to X-rays, and is preferably made of a transparent material such as polysulfone, polycarbonate, or acryl resins or the like. Further, the sheath 1 has its tip rounded off for fear that it may injure adjacent nearby vessels and organs.

As shown in FIG. 1, the mandrin 2 for expansion is a structure cylindrical in form which is to be introduced into the treatment channel 11 of the sheath 1, and acts as a core needle (adapter) when the sheath 1 is inserted into the body. The mandrin 2 for expansion is so constructed that, its insert 31 which is to be introduced into the treatment channel 11, becomes longer than the treatment channel 11. Thus, the tip 32 of the mandrin 2 protrudes from the tip of the sheath 1 when fully pushed in. The tip 32 is shaped like a tapered cone. Around the outer surface of the mandrin 2 for expansion, is placed an O-ring 33 which acts both as a sealing means to seal the gap between the mandrin and the sheath 1, and as a means fixing the mandrin to the sheath 1. At the rear end of the mandrin 2 for expansion is placed a flange 34. At the terminal end of the mandrin 2 for expansion, is placed a rubber cap 36 which acts as a sealing means and allows tools to be introduced into the internal cavity (channel) 35 of the mandrin 2, to be introduced there in an air-tight manner. The rubber cap 36 is provided with a rubber plug 37 which will close the opening left when a tool which has been introduced into the internal cavity of the mandrarin is withdrawn.

The flange 34 placed around the mandrin 2 for expansion has part of its upper wall which corresponds with the passage of the scope channel 12 and spike channels 21, removed to form a flat surface or an escape 38 so that it does not interfere with the passage of tools through the scope channel 12 and spike channels 21. As shown in FIG. 2A, the mandrin is so constructed as to allow a positioning pin 39 to be attached on the base side of the flange 34. This positioning pin 39 acts as a means by which to adjust the positioning of the mandrin 2 relative to the sheath 1: the escape 38 is placed directing its face properly upwards when, after the mandrin 2 has been introduced into the treatment channel 11, the positioning pin 39 is inserted into a fitting groove 18 prepared on the flange 13 of the sheath.

The rod 3 is a slender tool to be inserted into the mandrin for expansion 2. The length of this rod 3 is longer than the length of the mandrin for expansion 2. The outer diameter of the rod 3 is smaller than a trocar conventionally used. The rod 3 has both ends similarly rounded and pointed, and can be easily inserted into the mandrin for expansion 2 regardless whether it is inserted from one end or the other.

The air-tight core cylinder 4, like the mandrin for expansion 2, has a cylindrical shape which is to be inserted into the treatment channel of the sheath 1. The insert 41 of the air-tight core cylinder 4 which is to be inserted into the treatment channel 11 has its length so adjusted that, even when it is inserted into the treatment channel 11 and an endoscope into the scope channel 12 of the same sheath 1, it will not interfere with the movement of the endoscope in the space of the treatment channel 11.

Around the basic end of the insert 41 of the air-tight core cylinder 4 are fastened an air-tight means which hermetically seals the gap between the cylinder 4 and the sheath 1, and an O-ring 42 which acts as a fixing means to stabilize the cylinder 4 with respect to the sheath 1. In addition, around the rear end of the air-tight core cylinder 4 is placed a flange 43. Further, at the rearmost end of the air-tight core cylinder 4 is provided a rubber cap 45 so that tools to be inserted into the internal cavity 44 are allowed to enter into that cavity in an air-tight manner through this rubber cap. To the rubber cap 45 is attached a rubber plug 46 which is to seal the hole to be made in the rubber cap when a tool which has been inserted into the cap is withdrawn therefrom. At the center of the rubber plug 46 attached to the rubber cap 45 is prepared a needle insertion point 47 which is made of a thin rubber film and has a convex surface towards the internal cavity. This is so constructed as to allow steel wires to be withdrawn without impairing the air-tightness of the cylinder. The flange 43 has its upper edge removed, and the resulting vacancy is to act as an escape 38 for tools which are to be inserted through the scope channel 12 and spike channels 21.

The spike 5 is made of a hard material, for example, a metal constituting a stainless steel wire. Further, the. spike 5 is so constructed as to have an outer diameter which allows it to pass through the spike channel 21. Further, the tip of the spike is sharp and acts as a penetrating point 49. The penetrating point is shaped, for example, like a tetrahedron. The rear end of the spike 5 has a hold 50.

These spikes 5 are separately inserted through the spike channels 21 so that their tips penetrate into the vertebral body of a vertebra. This arrangement allows the spikes not only to act as a fixing means for the sheath 1 with respect to the vertebral body but also to act as a second joining means for the tip of the sheath 1 against the bone.

The plug for scope channel 6 is inserted into the basic end of the scope channel 12 to hermetically seal that channel while the channel remains vacant without receiving the endoscope, and achieves this end by closely contacting with the O-ring 14 placed around the scope channel 12 of the sheath 1.

The plug for spike channel 7 is to close the spike channel 21 prepared in the body of the sheath 1. This is inserted into the basic end of the spike channel 21 while that channel remains vacant without receiving the spike 5. This plug for spike channel 7 is made of an elastic material such as nylon, teflon or the like, and consists of an insert 51 and a handle 52. The insert 51 consists further of a tip segment which is thinner than the internal diameter of the spike channel 21, and of an air-tight segment which is placed more close to the base than the tip segment, and is as thick as, or slightly thicker than the internal diameter of the spike channel. 21.

For the present embodiment, a suction pipe 8 is provided as an element of the system. This suction pipe 8 is equipped with a body 55, and is connected through a nearly 90° bent to the body 55. To the base of the body of the suction pipe 55 is attached a metal mouth 56 which is to be connected to a suction tube not illustrated here. To the body 55 of the suction pipe 8 is attached a joint adapter 57. To the rear end of the sheath 1 which forms the outlet of the treatment channel 11 may be attached a stopper mechanism (not shown) which will restrict the inward movement of treatment tools, particularly of chisels and drill cutters whereby they are prevented from being inserted beyond a certain depth.

Now, the use of the cavity-retaining tool for bone surgery of this embodiment will be described.

In this example, the tool is applied for a surgery case where approach towards the spinal column is made through a peritoneal membrane under laparoscopic monitoring, to resect and fix the intervertebral disc (L5-S) between the fifth lumber vertebra (L5) and the sacral bone (S) as shown in FIG. 7.

As shown in FIG. 7, on the front aspect of the vertebral body 70 run aorta and inferior vena cava 71 (aorta 71a and inferior vena cava 71b) or principal vessels in the body. Aorta 71a and inferior vena cave 71b bifurcate at a level corresponding with the sacral bone S, and their branches are placed one over the other. To get access to the site to be treated of the vertebral body 70, it is necessary therefore to approach the vertebral body 70 from the side as indicated by arrow B in the figure, avoiding these vessels, and to expose the site in question.

In view of this, as indicated in FIG. 3A, a pneumoperitoneum is made according to convention, and trocars 73 are inserted through the abdominal wall 72. Then, a laparoscope 15 and a retractor 74 are inserted through these trocars 73, and under endoscopic monitoring, aorta and inferior vena cava 71 are pushed aside sufficiently from the frontal aspect of the vertebral body 70 to expose the site to be treated of the vertebral body 70 and its surrounds.

Next, a superficial incision is made on the site of the abdominal wall 72 that will give a best route for the cavity-retaining tool to approach the vertebral body in question, and a rod 3 is inserted through the incision. Or otherwise, if a trocar 73 is close to the ideal site, the rod 3 may be inserted through the trocar into the peritoneal cavity. If the rod employs a trocar 73 hole for penetration, it should be kept in position after having been inserted through the trocar 73 and the trocar 73 been removed. As the rod 3 is slender in form as mentioned above, and its external diameter is constant all through its length, the trocar can be smoothly removed from the body leaving the rod 3 to stay in the body.

Let's assume that a mandrin for expansion 2 has been inserted through a treatment channel 11 prepared in the body of a sheath 1, a plug for scope channel 6 has been inserted into a scope channel 12, and plugs for spike channels 7 have been inserted into spike channels 21. At this state all channels of the sheath 1 remain closed. An O-ring 33 placed around the mandrin for expansion 2, an O-ring 14 placed around the scope channel 12 and the plugs for spike channels 7 are all made of elastic materials, and they maintain air-tightness by undergoing deformation when pushed into respective channels.

Figure 3B:
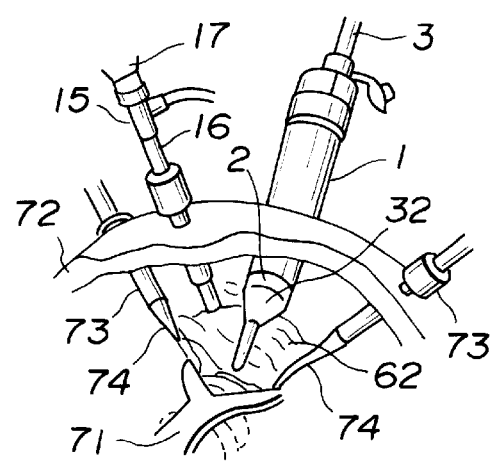
FIG. 3B shows how the sheath is introduced into the body after muscle layers have been pushed aside by the tip of a mandrin for space expansion.

Next, another superficial incision is made about the hole through which the rod 3 has been inserted, such that the hole can narrowly accommodate the insertion of the sheath 1. At this state, the sheath 1 is adjusted in its position with respect to the rod 3 which has been kept inserted into the peritoneal cavity 72 so that the rear end of the rod 3 slides into the internal cavity 35 of the mandrin for expansion 2 which has been placed in the sheath 1. The sheath 1 is allowed to advance until its front end strikes against the incision, and then the mandrin for expansion 2 is screwed in utilizing the rod 3 inserted in the body as a guide. As the mandrin for expansion 2 has a tapered end 32 as shown in FIG. 3B, it separates muscle layers to leave a room for the sheath 1 to advance therethrough into the body.

As seen from above, the pneumoperitoneum maintains its air-tightness while the sheath 1 is being advanced into the body, and hence it is possible to observe the advancement into the peritoneum with a laparoscope 15. Because the sheath 1 has a convex surface all around its periphery, it is easy for the sheath to be inserted into body and to keep air-tightness during insertion.

Then, the mandrin for expansion 2 and rod 3 are removed from the sheath 1, and an air-tight core cylinder 4 is applied to the treatment channel 11 of the sheath 1. An O-ring 42 of the air-tight core cylinder 4 maintains the air-tightness of the peritoneal cavity. During this operation, the internal cavity 44 of the air-tight core cylinder 4 should be kept closed with a rubber plug 46.

As the pneumoperitoneum maintains its air-tightness at this state, it is possible to open the rubber plug 46 of the air-tight core cylinder 4 and to insert a laparoscope 15 through the core cylinder to observe the peritoneal cavity. Alternatively, according to a given condition, the laparoscope 15 inserted through the trocar 73 may be withdrawn and inserted through the core cylinder for the same purpose. Or a plug for scope channel 6 may be removed, and the laparoscope 15 may be inserted through the now opened scope channel to observe the peritoneal cavity. During this operation, the air-tightness of the peritoneal cavity is maintained with a rubber cap 45 attached to the air-tight core cylinder 4 and an O-ring 14 placed around the scope channel 12.

It is possible to insert a treatment tool through the air-tight core cylinder 4 while the air-tightness of the interval cavity 44 of the cylinder is being maintained.

Figure 3C:
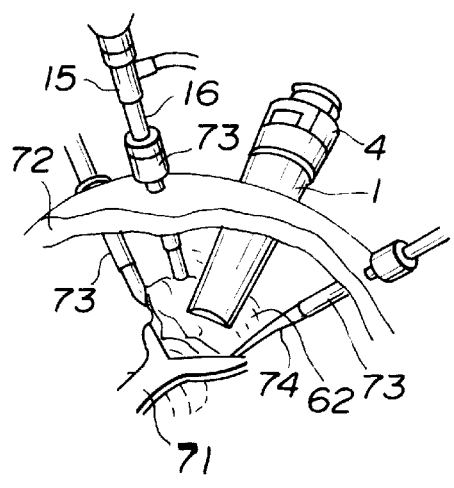
FIG. 3C shows how a cavity to receive the tip of the sheath is formed after tissues such as muscles have been pushed aside by pressure, and how the sheath is introduced into that cavity under microscope monitoring.
Figure 3D:
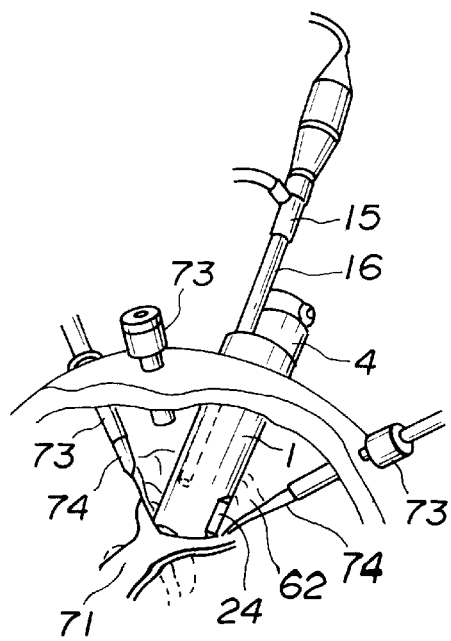
FIG. 3D shows how the sheath is properly stabilized by contacting its tip onto the surface of a vertebral body.

Next, as shown in FIG. 3C, tissues 62 such as vessels, organs and muscles are pushed aside mechanically to make such a wide room that the tip of the sheath 1 can be safely stabilized against a vertebral body 70, and then, under endoscopic monitoring, the sheath 1 is pushed in until its front end securely rests against the vertebral body. At this point of time, the plug 6 for scope channel is removed, and the laparoscope 15 inserted through the scope channel and fixed in a position to give a good view of the site to be operated. At this state the operator can observe the vertebral body 70 from front through the internal cavity of the sheath 1. The tip of the sheath is finely adjusted so as to allow the operator to watch the intervertebral disc between L5-S at the center of the contour of sheath 1. Because the sheath 1 has a tip whose external outline is shaped like a concave arch so that the outline corresponds with the perimeter of a vertebral body 70, the sheath 1 can securely rest against the vertebral body 70 by placing the tip in close contact with the vertebral body 70 (see FIG. 3D). Further, as shown in FIG. 6, the two spike channels 21 are adjusted in position so that their tips rest on one side of the vertebrae sandwiching the L5-S intervertebral disc.

At this stage, adjacent vessels and muscles are prevented from entering into the internal cavity with the wall of the sheath 1, or captured by a depression 24 for rejected organs. Even if vessels enter by accident from under the bottom of the sheath 1 into the internal cavity, or lie beneath the bottom of the sheath 1, they can be easily recognized because the tip of the sheath 1 has an outwardly widened rim or a taper 19 to facilitate the visibility of the periphery.

At this stage it is possible, to check whether a proper approach has been made towards the intervertebral disc to be treated, to insert a metal wire into a needle insertion point 47 made of a thin rubber membrane of the rubber plug 46 while keeping that rubber plug 46 of air-tight core cylinder 4 closed, to penetrate the wire into the intervertebral disc under endoscopic monitoring, and to take X-ray photography of the site for inspection. As the air-tightness of the peritoneal cavity is maintained after the wire has been withdrawn, this checking will not interfere with any subsequent operations. Further, because the sheath 1 is made of a resin, it will not interfere with X-ray photography.

Figure 4A:
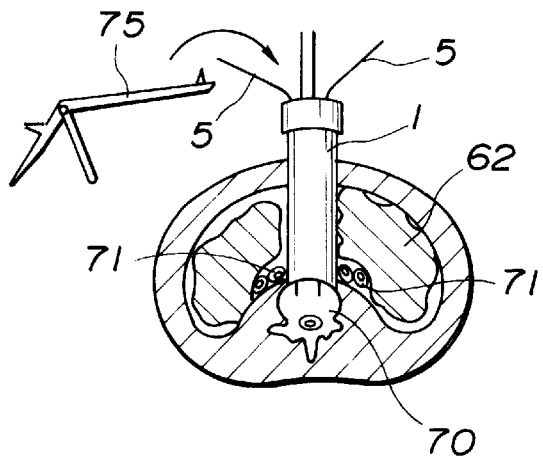
FIG. 4A shows how spikes are driven into a vertebral body.
Figure 4B:
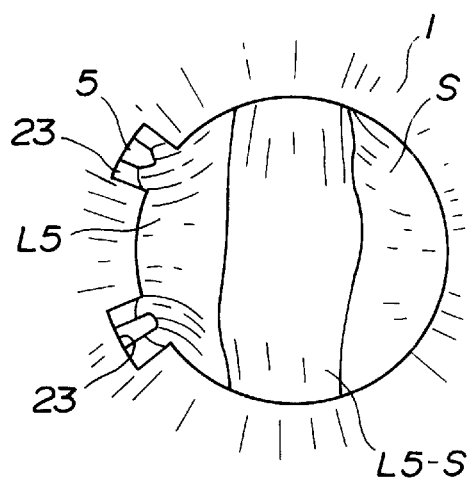
FIG. 4B gives a view after the spikes have been driven into the vertebral body.

At the time when the sheath 1 has securely rested against the front aspect of the vertebral body 70, and the laparoscope 15 has been inserted through the sheath 1 and properly positioned with respect to the vertebral body 70, spikes 5 are inserted through the spike channels 21 of the sheath 1 as shown in FIGS. 4A and 4B. The spikes are allowed to protrude from the front ends of the spike channels 21, and to be driven into the vertebral body 70, thereby to further stabilize the sheath 1 with respect to the vertebral body. During this operation, as the sheath 1 has shelter ports 23 at the periphery of the visual field of the scope, driving of spikes into the vertebral body can take place under direct vision through endoscopy. Further, as the front end of the spike channel 21 opens its mouth in and communicates with the internal cavity of the sheath 1, it is safely avoided to inflict injuries to organs close to outside of the sheath 1 during driving of the spike 5 into the vertebral body.

Treatment of the vertebral body 70 will be directly performed by way of the sheath 1 while the visual images supplied by the laparoscope 15 inserted through the sheath 1 are being monitored. Because no entry of organs into the internal cavity of the sheath 1 takes place, the sheath 1 is securely fixed against the vertebral body, and the laparoscope 15 shares a common field with the treatment channel 11, subsequent operations can be safely performed in the interior of the sheath 1 using tools adapted for the vertebral treatment such as curettes 75. The endoscope is securely fixed to the sheath 1 and provides a stable visual field. The pneumoperitoneum may be relaxed at this point of time (see FIG. 4A). Needless to say, the pneumoperitoneum may be resumed as appropriate.

Figure 5:
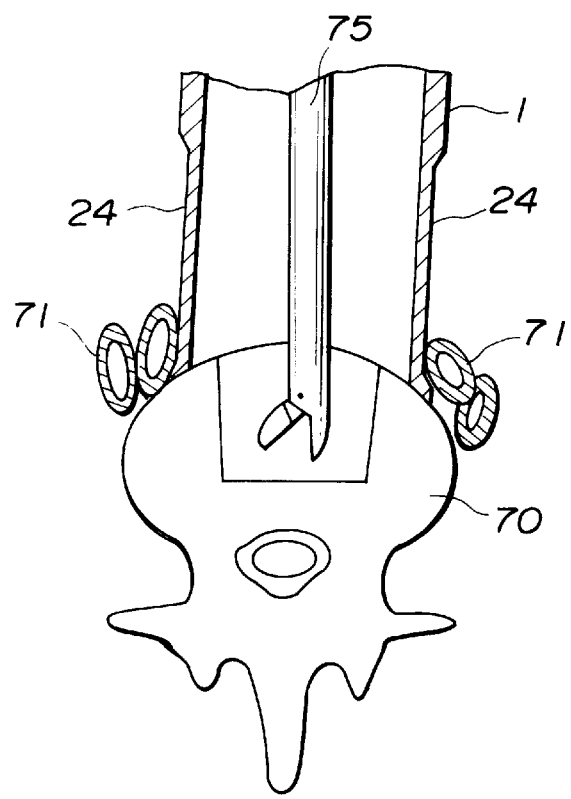

The air-tight core cylinder 4 is removed from the sheath 1, and tools for vertebral treatment are inserted through the treatment channel 11 to treat the vertebra as shown in FIG. 5. Take as an illustration a case where an autograft is implanted for fixation of the front aspect of a vertebra. A lancet 76 is pushed into the L5-S intervertebral disc as shown in FIG. 6A, to cut part of a fibrous ring 61. Then, the medullar nucleus and disc are removed with, for example, a curette 75 as shown in FIG. 6B. Further, as shown in FIG. 6C, bones of L5 and S are removed with a chisel 77. As the cavity within the sheath 1 forms a straight channel, it allows the operator to impose a linear, intense strength to those tools which is necessary for this type of surgery Then, the two vertebral bodies are stretched in opposite directions with a wound opener not illustrated here. The spikes 5 do not stand in the way of this operation, because they have been driven into the same vertebral body. Later, as shown in FIG. 6D, an autograft 78 is implanted into the extended cavity between the vertebral bodies, to complete the operation for anterior fixation.

Alternatively, an implant such as disclosed in WO 94/17759 is inserted between vertebral bodies, and a fixing agent is applied through the treatment channel 11 of the sheath 1.

Needless to say, this invention can be applied for every possible operation requiring an approach towards a vertebral body, not to mention of the fixation of a vertebral body.

Figure 8:
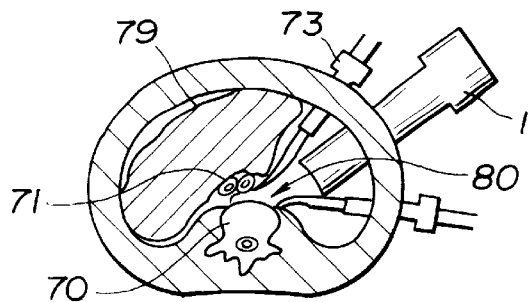
Figure 9:
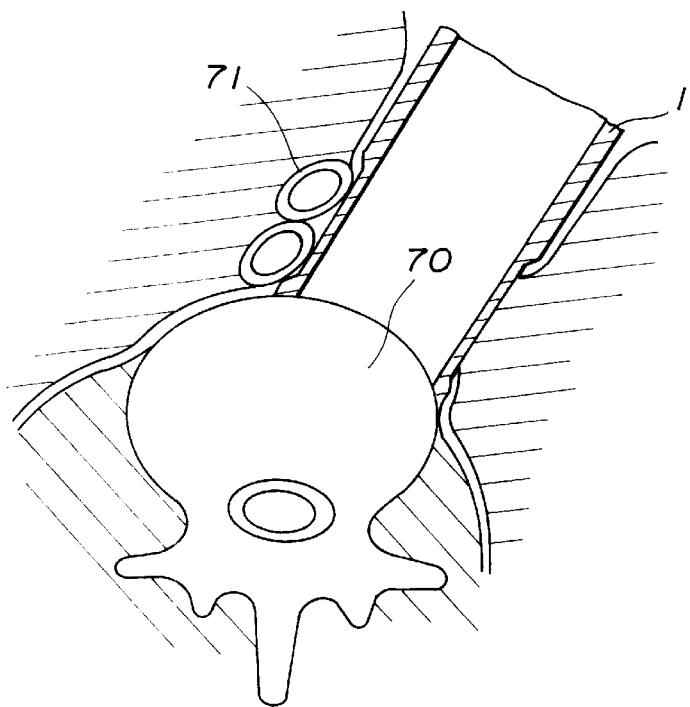

As a further modification, when a periperitoneal approach is made towards the L4-5 intervertebral disc instead of the L5-S intervertebral disc, the sheath 1 is allowed to approach towards a vertebral body 70, stripping the peritoneum 79 under laparoscopic observation as is shown in FIG. 8. After aorta and inferior vena cava 71 have been pushed aside together, a cavity 80 is formed into which the sheath 1 is inserted as shown in FIG. 9. As in the foregoing operation, the sheath 1 rests securely against the vertebral body by means of the joining and fixing means. Then, approach is made towards the vertebral body 70 from the direction indicated by arrow C in FIG. 7.

As seen from above, as this embodiment has the sheath 1 equipped with the spike channels 21 which act as a passage through which spikes 5 or an anchoring means are passed, it is possible to fit the sheath 1 to the vertebral body and to fix it thereto. This arrangement relieves the operator of the necessity of rejecting organs once the sheath has been fixed, ensures a work space within the internal cavity of the sheath 1 for surgery of bones, and isolates that work space from adjacent organs and tissues, thereby freeing the operator from anxieties involved in possible infliction of damages to adjacent organs. This arrangement further ensures a good field of vision.

Further, once the sheath 1 has been fitted to and fixed against the vertebral body 70, organs are prevented from entering into the internal cavity of the sheath 1, and hence the pneumoperitoneum may be relaxed. Thus, it becomes unnecessary to maintain the distended state of the pneumoperitoneum by the infusion of carbon dioxide gas. This dispenses with the use of gas infusion, and encourages the progress of the treatment.

Further, this will shorten the time necessary for maintenance of the pneumoperitoneum, which will relieve the patient of a burden involved in the operation. This will cause carbon dioxide gas to be consumed less, and be economical. Further this will lessen the effect of carbon dioxide gas on the patient's body.

Furthermore, as an endoscope and a treatment tool are inserted into the sheath 1 to serve for the treatment, a proper treatment can be done only in the confine of the sheath 1, once the sheath 1 has been stabilized against the vertebral body.

The sheath 1 has a tip shaped like a concave arch to act as a fitting means which corresponds with the external perimeter of a vertebral body. This arch not only helps the tip to be fixed against the vertebral body without slipping over its surface but also prevents organs from entering from under the tip into the internal cavity of the sheath 1. This arrangement further relieves the operator of anxieties involved in possible infliction of damages to adjacent organs.

Further, as the front opening of the spike channel 21 is directed towards and communicates with the internal cavity of the sheath 1, it is safely avoided to inflict injuries to organs outside the outer rim of the sheath 1 during driving of the spike 5 into the vertebral body.

Still further, as the spike channel 21 is so designed as to come into the visual field of the endoscope inserted through the sheath 1, it is possible to check how the spike 5 is driven into the vertebral body, which will help the stabilizing operation to proceed more safely than otherwise possible.

Still further, as the spike channels are prepared on one side of the sheath 1, it is possible to spread an intervertebral space while keeping the sheath fixed against an adjacent vertebral body.

Still further, as the spike channel is provided at its rear end with a plug 7 for spike channel to keep the channel air-tight, the spike can be used even during the operation requiring air-tightness.

Still further, as the spike channel 21 is prepared in the wall of the sheath 1, it scarcely suffer damages. Furthermore, as part of the spike channel 21 is arranged inside the sheath 1, even'if the channel is destroyed by accident, the spike inserted therein will never come out from the sheath 1. This will contribute to the improvement of safety.

This embodiment is the system comprising the sheath 1 equipped with the scope channel 12 and the treatment channel 11, the mandrin 2 acting as a core needle, and the air-tight cylinder 4 acting as an air-tight adapter and allows the sheath 1 to be inserted into a pneumoperitoneum in an air-tight manner. When the mandrin 2 is exchanged for the air-tight cylinder 4, it will be possible to take photographic images of tissues in the pneumoperitoneum through the sheath 1. Further, as the internal cavity of the air-tight cylinder 4 allows, while maintaining air-tightness, operating tools to be inserted through, it enables the operation to proceed in the space of the sheath 1.

Further, as the scope channel 12 communicates with the treatment channel 11 with a slight angle, the axis of the endoscope and that of the treatment channel 11 separate from each other , as they move towards the rear end of the sheath 1. This arrangement will allow tools and a scope to be inserted into the treatment and scope channels 11 and 12 respectively, and to be handled without being interfered by the movement of each other.

Still further, as the axis of the endoscope and that of the treatment channel 11 are so made as to fall on different points at the cross-section of the tip of the sheath 1, so that protrusion of the endoscope into the internal space is minimized. This arrangement will allow a maximally effective utilization of the cross-section of the treatment channel 11 of the sheath 1 for operation, which then will enable a considerably big site to be operated by this system.

Still further, the O-ring 14 is mounted to the scope channel 12 to immobilize the endoscope at any desired position. This is very convenient for the operator when in work, because he can only hold the scope to maintain its stability. This arrangement ensures images free from blurs and a constant field of vision.

Still further, as the sheath 1 has part of its tip made transparent, it is possible, while operation proceeds within the space of the sheath 1, to observe the surround through the transparent segment. Or, the operator can watch through the transparent segment with a laparoscope not only the operation taking place in the internal cavity of the sheath but also organs on the opposite side. This ensures the operation to proceed safely and easily.

Still further, as the sheath 1 is made of a resin which is electron-permeable, it will not interfere with electron transmission even when X-ray photography or X-ray monitoring is carried out.

Still further, as the sheath 1 has a wall whose cross-section comprises convex or straight lines, it will not develop any conspicuous frictions when inserted through an incision, and maintain air-tightness because its wall will get a close contact with surrounding tissues.

The system of this embodiment can be applied for the operation not only of lumbar vertebrae but also of any other bones including cervical vertebrae.

Further, this system can be applied with profit to a bone which is bounded with tissues including no cavities or which is embedded in tissues (for example a bone embedded in subcutaneous tissues such as muscles) by separating or cutting the tissues to reach the bone, and inserting the sheath of this embodiment down to the bone, and applying the same treatment on that bone. For example, dorsal approach to a lumber vertebra, or treatment of bones in an upper or lower limb is possible with this system.

Figure 10:
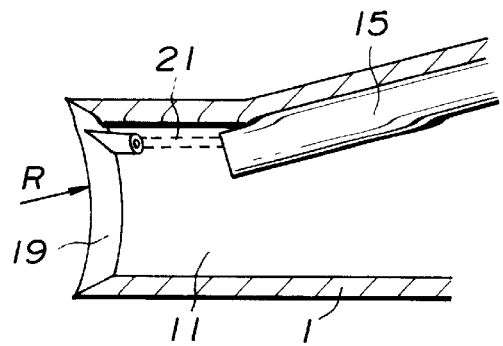
FIG. 10 gives a sectional view of the tip of a modified version of the sheath used in the first embodiment.

In the first embodiment described above, the sheath 1 has a tip shaped like a concave arch, which refers to the surface inwardly curved of the tip when seen from the direction indicated by arrow A in FIG. 1. The curvature of the arch can be varied according to the site to which the system is applied. Thus, the tip of the sheath can have an inwardly curved surface along the long axis as shown in FIG. 10. Of course, the tip can take any other shape by combining the two extremes above as appropriate according to the shape of a bone to which it is applied.

Needless to say, this embodiment can be applied for the operation which will not require pneumoperitoneum as well (for example, by retaining a cavity while raising the abdominal wall with a steel member or the like, or through other means).

The second embodiment of this invention will be described below with reference to FIGS. 11 and 12.

Figure 11A:
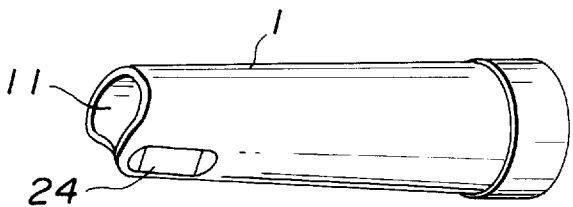
FIG. 11A shows how an inner sheath is inserted into an outer sheath.
Figure 11B:
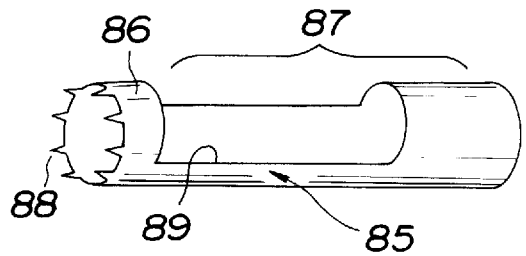
FIG. 11B gives a perspective view of the inner sheath.
Figure 12:
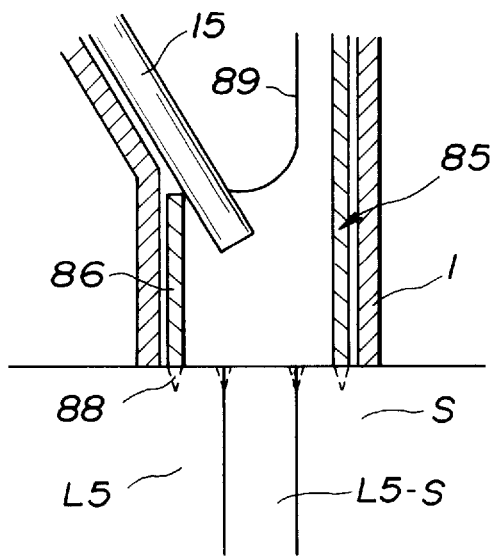

A sheath 1 of this embodiment lacks such spike channels 21 as are provided for the first embodiment, as is shown in FIG. 11A. Fitting and fixing of the sheath 1 against a vertebral body is achieved by an inner sheath for fixation 85 (inner sheath) which is to be inserted into a treatment channel 11 of the sheath 1 as shown in FIG. 11B. This inner sheath for fixation 85 is a cylinder-shaped member whose outer diameter is nearly the same with the internal diameter of the above sheath 1 (outer sheath), and consists of a fixing end 86 at the tip. and a stem 87 at the base. The fixing end 86 takes a ring form, and has spines 88 at its terminal edge. The spines 88 penetrate into a vertebral body, and fit to the bone, thereby to fix the sheath 1 against the vertebral body.

The fixing end 86 is shorter than the distance between the tip of sheath 1 and the site at which the scope channel 12 communicates with the internal cavity of sheath 1. Posterior to the fixing end 86 is prepared a window 89 which is to receive the passage of an endoscope. The sheath 1 is otherwise similar to that used in the first embodiment.

The system of this embodiment can be used similarly to that of the first embodiment, but when the sheath 1 is fixed onto the front aspect of a vertebral body, an air-tight core cylinder 4 is withdrawn and instead the inner sheath for fixation 85 is inserted into the treatment channel 11 of the sheath 1. Before the inner sheath is inserted, a laparoscope 15 must be withdrawn until it reaches a position where it completely comes out of the range covered by the treatment channel 11 of the sheath 1. After the fixing end 86 of the inner sheath 85 moves past an imaginary point where the extensions of treatment channel 11 and of scope channel 12 intersect, the endoscope is moved so as to give a good view, and the fixing end 86 is viewed through the internal cavity of the inner sheath 85. Under endoscopic monitoring the inner sheath 85 is advanced further until it strikes against a vertebral body. Then, the rear end of the stem 87 is struck with a hammer to drive the fixing end 86 with spines 88 into the vertebral body under endoscopic monitoring (see FIG. 12).

The outer diameter of the inner sheath 85 is nearly the same with the internal diameter of the treatment channel 11 of the sheath 1, and hence the sheath 1 is fixed against the vertebral body.

Treatment of the vertebral body proceeds in the same manner as described above. The sheath 1 can be rotated around the inner sheath 85, and thus, when a different angle of view is required, the sheath is turned around so that a desired angle of view can be obtained.

As seen from above, because the sheath 1 can be easily rotated, it is also easy to change a field of vision of the endoscope.

Figure 13:
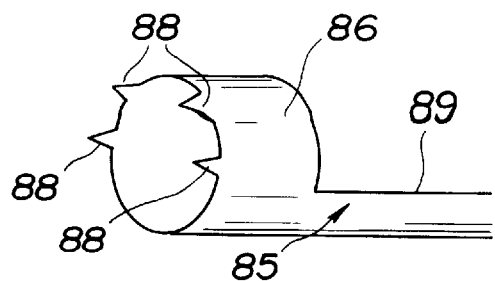
FIG. 13 gives a perspective view of the tip of a modified version of the sheath used in the second embodiment.

A modification of the second embodiment will be described with reference to FIG. 13.

In this modification, unlike the system of the second embodiment, spines 88 are placed on one half of the fixing end 85, instead of its whole circumference, namely, spines 88 are placed, for example, on the upper half of the fixing end 85.

This is applied for a case where an intervertebral space must be spread, and the spines 88 of the fixing end 85 are applied onto one of the adjacent two vertebrae.

As seen from above, as this fixing end has spines 88 only on one half of its circumference, and thus can apply them only to one vertebra, it is possible to spread the intervertebral space while observing it y endoscopy from the sheath 1.

The third embodiment of this invention will be described with reference to FIG. 14.

This embodiment is different from the first one in that the sheath 1 has a duplicate structure composed of two overlapped elements which can rotate freely over each other.

Figure 14A:
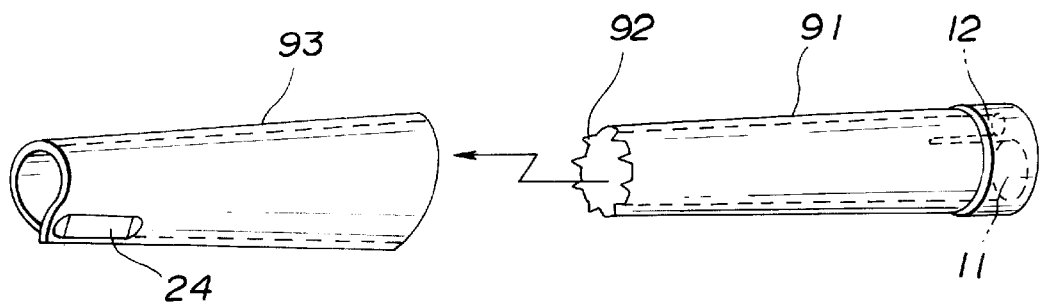
FIG. 14A illustrates the relation between outer and inner sheaths.

As shown in FIG. 14A, an inner sheath 91 is similarly shaped to the sheath 1 of the first embodiment described above, but it lacks spike channels, and has spines 92 at its tip.

Figure 14B:
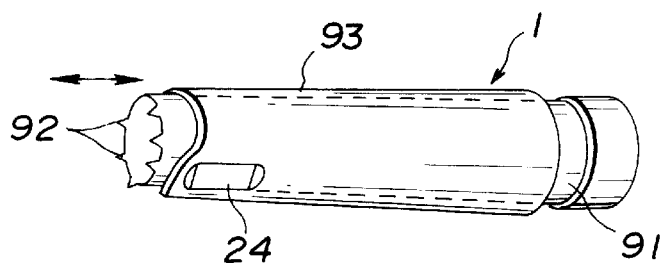
FIG. 14B illustrates how the inner sheath and the outer sheath are placed one under the other.

The outer sheath 93 can be fixed, with respect to the inner sheath 91, at a position just to cover the tip of the inner sheath 91 (not shown). As shown in FIG. 14B, the inner sheath 91 can freely slide within the outer sheath 93 so that its end can come out from the tip of outer sheath 93 as is indicated by the arrow. Further, the outer sheath 93 has the tip shaped like a concave arch. as in the sheath of the first embodiment so that it can apply the tip snugly to a vertebral body, and thus the tip acts as a fitting means. An air-tight means (not shown) is provided between the inner and outer sheaths 91 and 93.

The use of this embodiment takes place principally in the same way as in the first embodiment. When the sheath is inserted, the sheath assembly with the outer sheath being kept at a position to allow it to just cover the tip of the inner sheath 91, is inserted into the body. It is advanced further until it strikes against a vertebral body, and then fixed there. An endoscope is inserted into a scope channel 12 of the inner sheath 91, and the fixation of the inner sheath 91 against the outer one 93 is released. Then, under endoscopic monitoring through the inner sheath 91, the inner sheath 91 is advanced until it strikes against a vertebral body, and spikes are driven into the vertebral body to fix the sheath assembly. After fixation, in the same manner as in the first embodiment, under endoscopic monitoring, a treatment is made on the vertebral body through the treatment channel 11.

Through this operation, the same effect as in the first embodiment can be obtained.

The fourth embodiment of this invention will be described with reference to FIGS. 15 and 16.

This embodiment is different from the first one in the shape of the tip of sheath 1. The sheath of this embodiment is specially designed to be adapted for the intervertebral discs between L4-5, and between L3-4.

Figure 15:
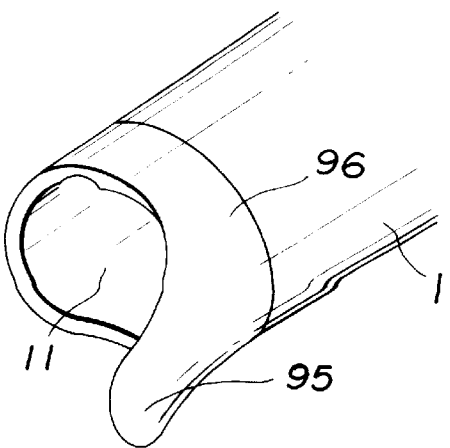
FIGS. 15 and 16 refer to the fourth embodiment of this invention.
Figure 16:
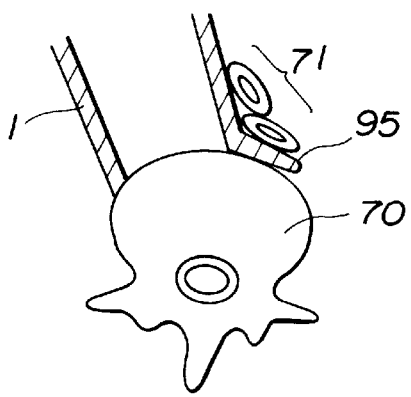

As shown in FIG. 15, a sheath 1 has a tip which has a front end 96 with a rejecter 95 in the form of a lobe (a projection). This lobular rejecter 95 is preferably made of an elastic material.

On the front aspect of the intervetebral disc of L4-5 run aorta and inferior vena cava 71 as shown in FIG. 7. These big vessels, as shown in FIG. 16, must be pushed aside sufficiently with a rejecter 95, before the sheath 11 is stabilized against the front aspect of the vertebral body 70.

As seen from above, as the rejecter 95 allows a secure rejection of such big vessels as aorta and inferior vena cava 71, the operation involving rejection of organs becomes easy and safe.

Figure 17:
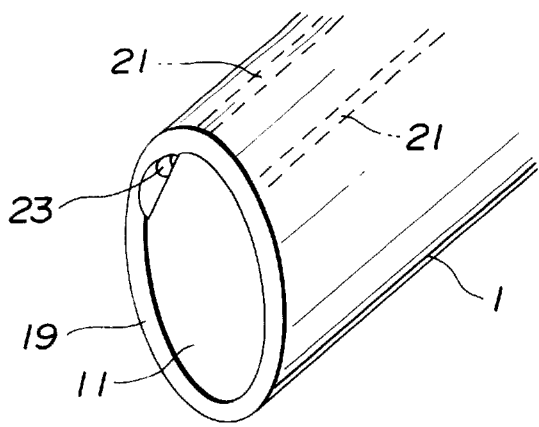
FIGS. 17 and 18 refer to the fifth embodiment of this invention.

The fifth embodiment of this invention will be described with reference to FIGS. 17 and 18.

This embodiment is different from the first one in the shape of the tip of sheath 1.

The sheath of this embodiment is specially designed to be adapted for the intervertebral disc between L5-S.

Figure 18:
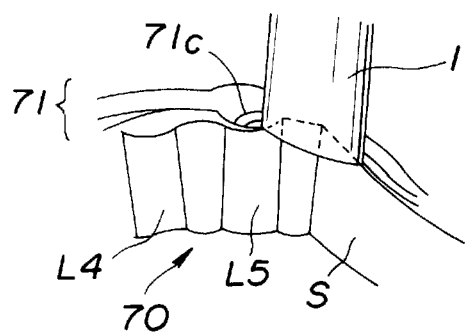

The shape of the structure around the L5-S intervetebral disc is as shown in FIG. 18. The tip of the sheath 1 is shaped as shown in FIG. 17 so as to fit to the structure around the L5-S intervetebral disc, that is, it has an obliquely cut end.

On the front aspect of the intervetebral disc between L5-S, as shown in FIG. 7, there exist bifurcations 71c of aorta and inferior vena cava 71, and as shown in FIG. 18, the sheath 1 is stabilized by fitting its tip to the outer rim of a vertebral body 70 beneath the bifurcations 71c.

As seen from above, as the sheath has a tip snugly fitting to the outer rim of the vertebral body, risk of injuring other organs will become less likely.

The sixth embodiment of this invention will be described with reference to FIG. 19.

Figure 19A:
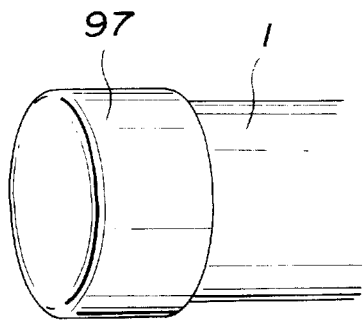
FIG. 19A gives a perspective view of the tip of a sheath.

This embodiment is different from the first one in the means by which the sheath is fitted to a vertebral body. As shown in FIG. 19A, a sheath 1 has its tip equipped with a fitting member 97. This fitting member 97 is made of a rubber-like elastic material, to put it more concretely, an elastic material such as teflon, or a rubber-like material such as silicone, and thus when it is pressed against a hard object, it undergoes deformation according to the shape of the object.

Figure 19B:
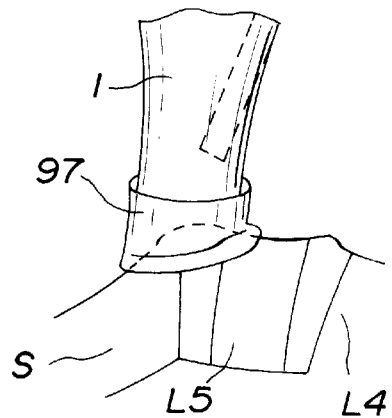
FIG. 19B illustrates how the sheath is put into use.

When the sheath 1 is stabilized against the front aspect of a vertebral body, the fitting member 97 of the sheath 1 is pressed against the vertebral body 70 as shown. in FIG. 19B. By this operation, the fitting member 97 undergoes deformation according to the external shape of the vertebral body 70, thereby to snugly fit, through the elastic deformation, to the external shape of the vertebral body 70.

As seen from above, as the fitting member 97 attached to the sheath 1 snugly fits to the external surface of the vertebral body 70 with no gap in between, it rejects the entry of other organs into the space within the sheath 1, thereby maintaining the cavity for treatment, and ensuring safe treatment. Further, as the fitting member 97 can be varied in form, it can be applied to vertebrae with different forms.

The seventh embodiment of this invention will be described with reference to FIG. 20.

A sheath 1 of this embodiment has a tip which is hinged with a pair of claws 98. These hinged claws 98 are so shaped that, when they are open, they come into close contact with and fit to the periphery of a vertebral body 70, and thus they act as a fitting means by which to fit the sheath to the external shape of a vertebral body. To each claw is connected a wire 99. The wire passes through the sheath 1 to the operator's hand, and thus, the operator can handle the claws 99 by manipulating the wire at hand.

Figure 20A:
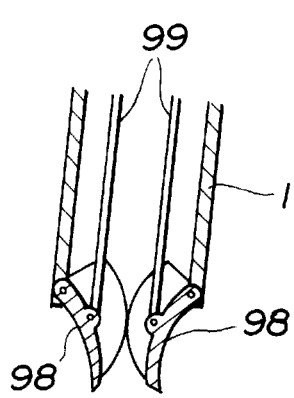
FIG. 20A gives a perspective view of the tip of a sheath.
Figure 20B:
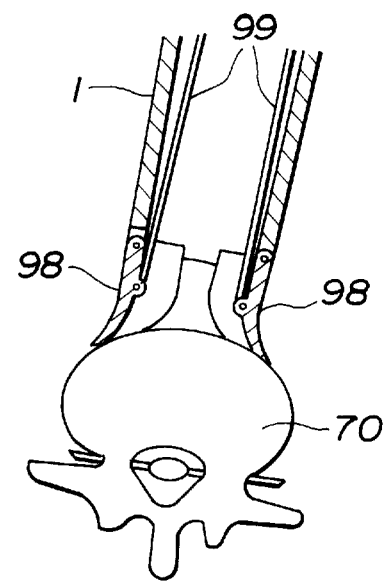
FIG. 20B illustrates how the sheath is put into use.

While the sheath is being inserted into the body, or until the sheath 1 is stabilized against a vertebral body, the claws 98 remain closed as shown in FIG. 20A. Then, as shown in FIG. 21B, just before the sheath comes into contact with a vertebral body, they are allowed to open, to take a shape to fit to the periphery of the vertebral body, and then to rest against the front aspect of the vertebral body thus to stabilize the sheath with respect to the vertebral body. As another application, the closed claws 98 can be inserted between organs in front of a vertebral body, and allowed to open, to separate those organs mechanically.

As seen above, the hinged claws 98, when organs are in front of a vertebral body and must be rejected before the sheath rests against the vertebral body, are inserted between those organs and allowed to open to separate the organs, thus to pave the way for the sheath to advance and to be stabilized against the front aspect of the vertebral body 70.

The eighth embodiment of this invention will be described with reference to FIGS. 21 and 22.

In this embodiment, a sheath 1 has in its wall one or a plurality of channels 111a, 111b, . . . to utilize them as channels for air-vent, water-suction, water-supply, or for them all, or for any one of them. One end of each channel. is connected to a metal port 112 at the base, which is provided with a cock 113 to open/close the passage through that channel 111a, 111b, . . .

Figure 21:
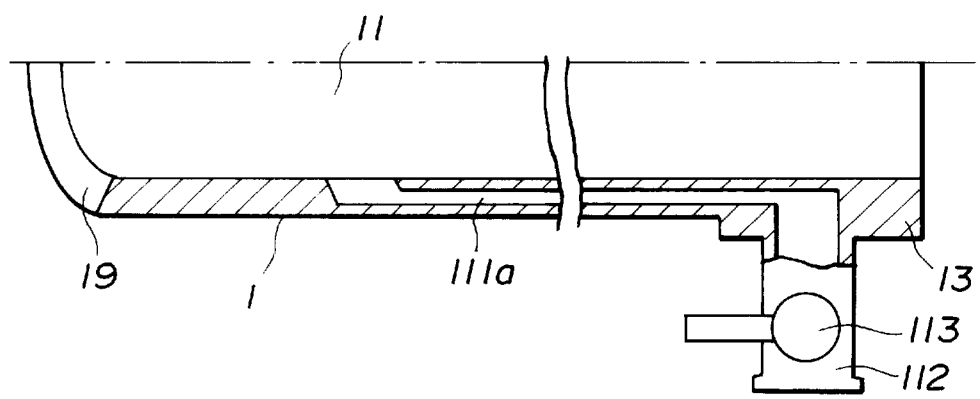
FIGS. 21 and 22 refer to the eighth embodiment of this invention.

The channel 111a shown in FIG. 21 is for the passage of exhaust gasses and sucked water. This channel 111a opens its mouth at a position on the sheath's internal wall slightly off from the tip of the sheath 1.

Figure 22:
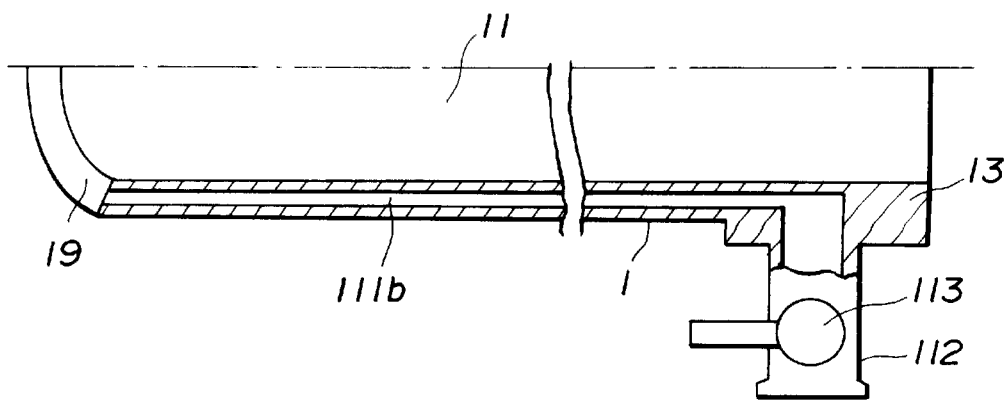

The channel 111b shown in FIG. 22 is for the passage of washing liquids and sucked water. This channel 111b opens its mouth at a point on the taper 19 of the sheath 1. The sheath 1 is provided with the two channels 111a and 111b shown in FIGS. 21 and 22. The sheath is otherwise similar to that of the first embodiment.

When an exhaust gas is discharged, a suction tube (not shown) is connected to a port 112 communicating with the channel 111a for the passage of exhaust gasses and sucked water, while a water-feed pipe(not shown) is connected to the other port 112 communicating with the channel 111b for the passage of washing liquids and sucked water for washing, or a water-suction tube is connected to the same port for water-suction, as the case may be. When necessary, a connector may be attached so that any desired tube can be selected as appropriate.

Take as an example a case where an electrocautery knife is used under endoscopic monitoring. During this operation, the cock 113 for the channel 111a is opened so that fumes can be discharged.

When part of a bone is removed, the resected bone bleeds continuously. To treat such bleeding, blood is suctioned through the channel 111b for the passage of washing liquids and sucked water. When part of a bone is resected, the channel is kept open for continuous suction, and then blood accumulating at the bottom of the sheath 1 is automatically suctioned and carried through the channel 111b which opens its mouth just at the tip of the sheath 1.

When it becomes necessary during operation to clean the work space, a washing liquid is supplied through the channel 111b, and the liquid is suctioned through the same channel 111b.

Further, when it becomes necessary to push away blood and tissue debris with a flush of liquid, thereby to clean the field of vision, an endoscope with a water-feed channel is inserted into the scope channel 12, or a washing liquid is fed through the channel 111b to pour the liquid into the space within the sheath 1, and the liquid is suctioned through the same channel 111b or through the other channel 111a, thereby to maintain the circulation of the liquid.

Gas-vent, water-suction and water-feed can take place by the channel 111a shown in FIG. 21 or by the channel 111b shown in FIG. 22. But generally speaking, the channel 111a shown in FIG. 21 is more appropriate for gas-vent and liquid circulation (water-feed and water-suction), while the channel 111b shown in FIG. 22 is more adapted for washing and water-suction such as suction of blood.

As seen from above, the sheath 1 provided with the channel 111a for gas-vent and water-suction and the channel 111b for washing and water-suction readily achieves gas-vent, washing, continuous suction, and continuous circulation.

Figure 23:
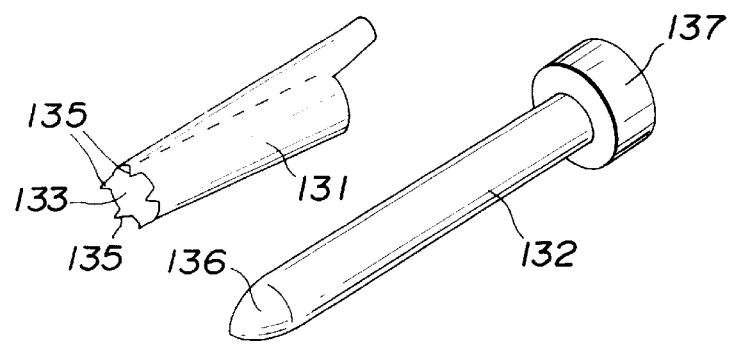
FIGS. 23–25 refer to the ninth embodiment of this invention.

The ninth embodiment of this invention will be described with reference to FIGS. 23–25.

This embodiment represents a cavity-retaining tool which approaches dorsally a lumbar vertebral body. As shown in FIG. 23, this cavity-retaining tool is provided with a sheath 131 and a slender core needle (rod) 132 to be inserted into the former, and the internal cavity of the sheath 131 constitutes a treatment channel 133. The rod 132 is inserted into the treatment channel 133 as if to penetrate it through.

Otherwise the sheath 131 has the same structure with that of the first embodiment including its constituent parts, that is, it has a scope channel 134, spike channels, etc.

The sheath 131 has spines 135 at its tip end. Thus, the sheath 131 drives the spikes 135 into the bony portion of a vertebral body, thereby to fitting and fixing itself to the vertebra.

The rod 132 has a tip rounded off like a cone. Therefore, the rod 132 can be safely driven into muscles or subcutaneous tissues, or inserted between tissues. The rod 132 has a handle 137 at the base end.

To approach a lumbar vertebra dorsally and retain a cavity there, firstly the rod 132 is inserted into the sheath 131 until its tip 136 comes out definitely from the tip of the sheath 131. Then, an incision is made on the skin posterior to the vertebra 140, and the rod 132 is allowed to penetrate through the incision, and to cut or tear off muscles until its tip reaches the bony part.

Figure 24:
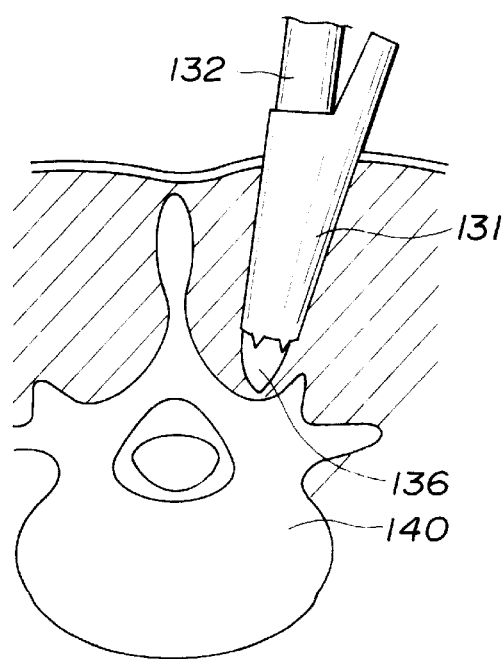
Figure 25:
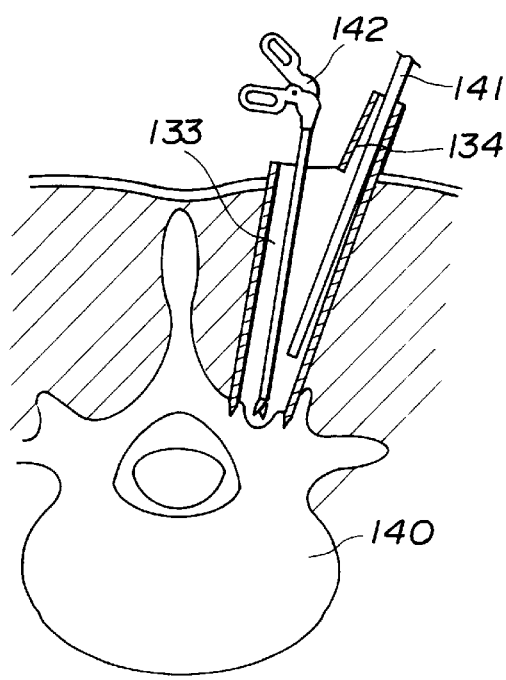

Then, as shown in FIG. 24, the sheath 131 is allowed to advance utilizing the rod 132 as a guide until its tip reaches the bony part. Further the spikes 135 are driven into the bony part so that the sheath 131 can come into close contact with and fit to the bony part (see FIG. 25).

Later, the rod 132 is withdrawn, to leave the treatment channel 133 of the sheath 131 vacant. Thus, a work space is ready for use in the cavity of the treatment channel 133 of the sheath 131. Then, an endoscope 141 is inserted into a scope channel 134. Thus, while the front space within the sheath 131 is monitored by endoscopy, treatment tools 142 such as forceps are inserted through the treatment channel 133 to make bone surgery. This arrangement is suitable for removal of an intervertebral disc or a vertebral arch.

Figure 26:
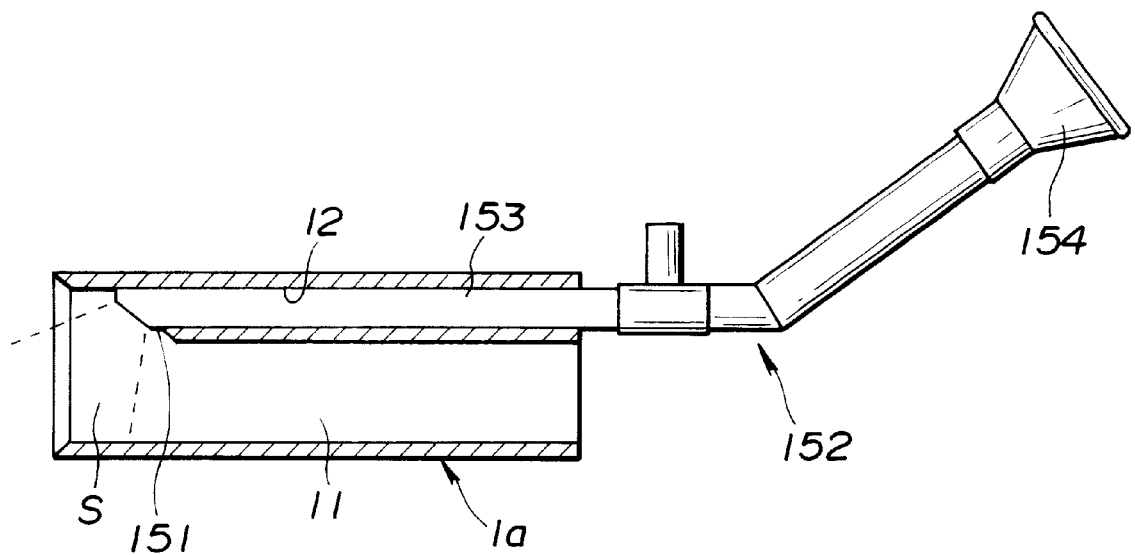
FIGS. 26 and 27 refer to the tenth embodiment of this invention.
Figure 27:
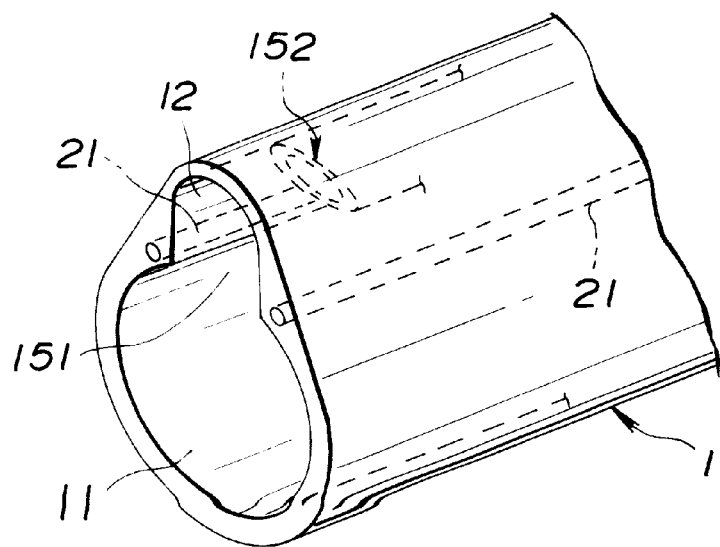

The tenth embodiment of this invention will be described with reference to FIGS. 26 and 27.

The cavity-retaining tool of this invention represents a modification of that used in the first embodiment. For the cavity-retaining sheath 1a of this embodiment, a scope channel 12 is placed in parallel with the treatment channel 11 which takes the form of a straight pipe as shown in FIG. 26. The scope channel 12 communicates at its tip with the tip of treatment channel 11 through a window 151 prepared at the junction as shown in FIG. 27.

An endoscope inserted into the scope channel 12, for example, a rigid-tube scope with an oblique eye-piece 152 adjusts the position of the tip of its light-guide tube 153 with respect to the window 151, and the sheath is so constructed as to allow the endoscope to see the work necessary for bone surgery within the confine of the treatment channel 11 through the window 151. The eye-piece segment 154 at the base end of the rigid scope 152 is so bent that it is placed apart from the treatment channel 11 although the light-guide tube 153 is closely apposed to the same channel.

The system is used in the same manner as in the first embodiment, but it is advantageous in that as the scope channel 12 is placed in parallel with the treatment channel 11, the endoscope does not interfere with the work executed in the work space for bone surgery in the treatment channel 11. As the rigid scope 152 with an oblique eye-piece can be used for endoscopy, the operator can enjoy a satisfactory and evenly-focused vision of the work space.

The eleventh embodiment of this invention will be described with reference to FIG. 28–45.

Figure 28:
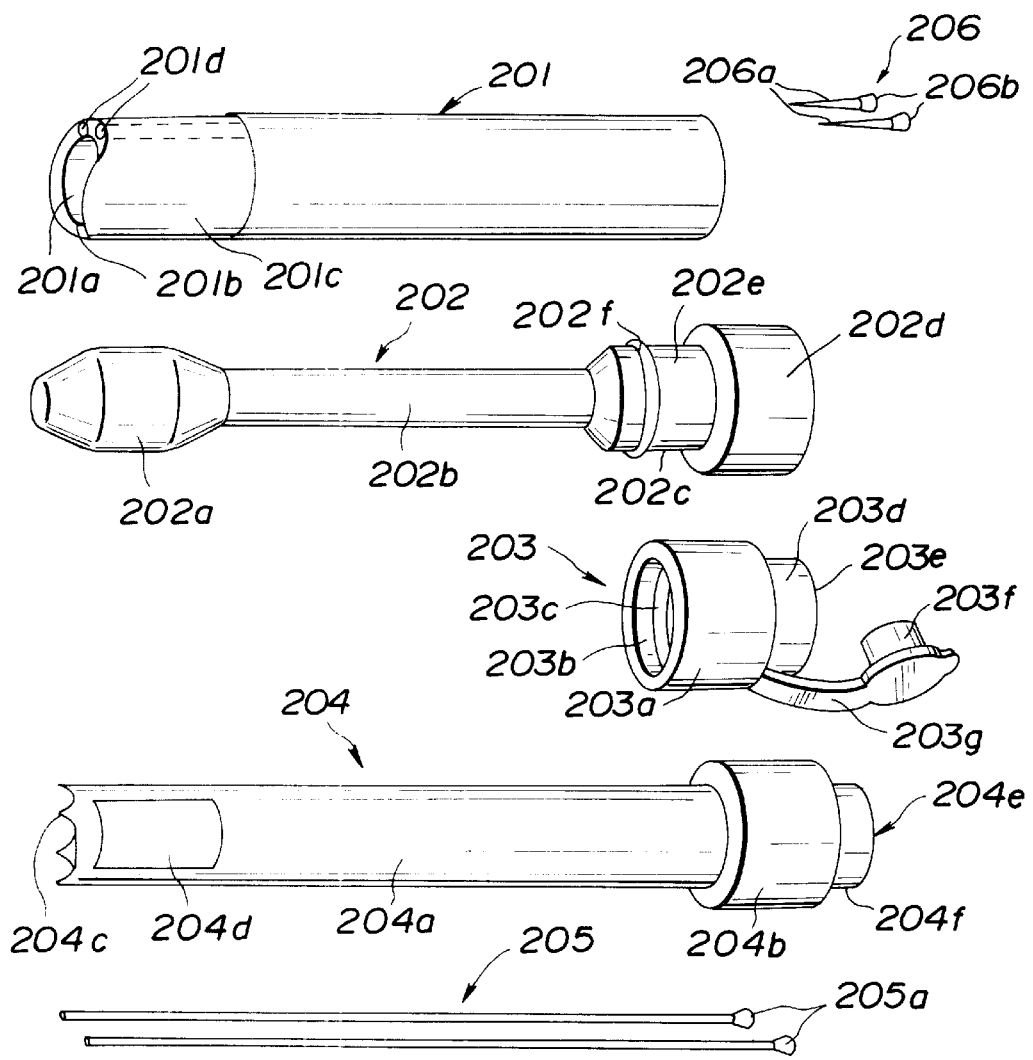

This embodiment relates to an intervertebral implant system. The intervertebral implant system comprises two subsystems: an implant guide sheath system as shown in FIG. 28 and a treatment tool system as shown in FIGS. 30–35. The implant guide system as shown in FIG. 28 is constituted principally with an outer sheath 201, a mandrin for expansion 202, an air-tight cap for outer sheath 203, an inner sheath 204, spikes 205 and spike channels 206.

The outer sheath 201 is made of a material shaped like a straight pipe whose cross-section is circular, and the internal cavity serves as a treatment channel 201a and a work space for bone surgery. The outer sheath 201 has its tip curved to form an escape 201b so that the tip can snugly fit to the surface of a vertebral body. This construction helps the sheath to fit to and to be properly placed with respect to the vertebral body. The tip of the outer sheath 201 is formed by a transparent segment 201c made of a transparent material which acts as a means through which to watch the work of bone surgery in the cavity of the sheath. Two spike channels 201d which run through the wall of the outer sheath 201 from the tip to the base are placed close to each other. Although in this embodiment the tip of the outer sheath is so constructed as to have an escape 201b to fit to a vertebral body, it may be made of a material (such as silicone rubber, polyurethane, vinyl chloride, etc.) which is so elastic as to freely fit to the external shape of a vertebra, and hence can be put in a proper position with respect to the vertebra.

The mandrin 202 for expansion is inserted into the treatment channel 201a of the outer sheath 201, and is used as a guide when the outer sheath 201 is inserted into the body. The mandrin 202 for expansion is constituted with a tip 202a, a stem 202b and a base 202c. The tip 202a is shaped like a cone, and its tip point is formed blunt. The tip 202a preferably has the maximum diameter nearly equal to the inner diameter of the treatment channel 201a of the outer sheath 201. To the rear end of the base 202c is attached a flange 202d. Around a small-bore segment 202e just anterior to the flange 202d is placed an O-ring 202f which acts as a seal when the mandrin 202 is inserted into the outer sheath 201. The small-bore segment is so constructed as to have an external diameter nearly equal to the internal diameter of the treatment channel 201a of the outer sheath. The stem 202b is so constructed that, when the mandrin 202 is inserted into the outer sheath 201 until the flange 202d hits against the rear end of the outer sheath 201, the tapered cone of the tip 202a can completely come out of the tip of the outer sheath 201.

Into the spike channel 201d, is inserted a spike 205 whose outer diameter is nearly equal to the internal diameter of that channel. The spike 205 has a sharply pointed tip like a cone or a pyramid and a hold 205a at its rear end. The spike 205 is so constructed that, when it is inserted into the spike channel until the hold 205a hits against the rear end of the outer sheath, its tip comes out by about 1.5 cm from the tip of the outer sheath 201.

While the spike channel 201d does not receive the spike 205 and remains open, a plug 206 for spike channel is pushed into this spike channel 201d. The plug 206 for spike channel is constituted with a plug segment 206a shaped like a tapered cone and a hold segment 206b.

A cap 203 for the outer sheath can be freely attached to or detached from the rear end of the outer sheath 201. The cap 203 for outer sheath has a concentric outer wall 203a. Around the internal annular segment 203b of the concentric outer wall 203a and close to the tip is placed an O-ring 203c. The internal annular segment 203b has an inner diameter close to that of the outer diameter of the outer sheath 201. The cap 203 for outer sheath has a port (not shown) for treatment tools at a position close to its rear end and at another position further towards the base a rubber cap 203d. The rubber cap 203d together with an opening 203e, a plug 203f and a connector 203g forms one segment. The opening 203e has a diameter close to the internal diameter of the outer sheath 201.

Figure 29:
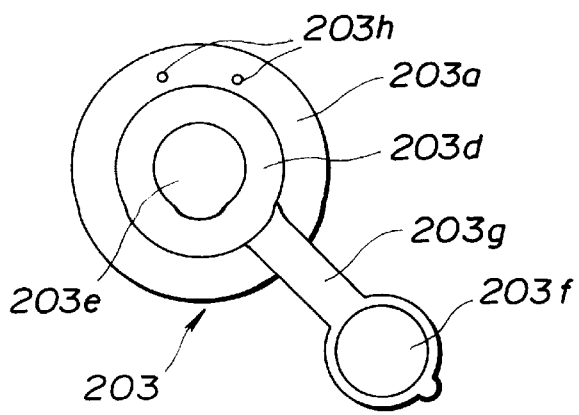

On the cap 203 for outer sheath are prepared small holes 203h which, when the cap is applied to the outer sheath 201, correspond with and communicate with the spike channels 201d (see FIG. 29).

The inner sheath 204 is inserted into the treatment channel 201a of the outer sheath 201 when use. The inner sheath 204 is constituted with a sheath segment 204a in the form of a straight pipe and a body 204b at the base. The internal cavity of the sheath segment acts as a treatment channel, or acts as a work space for surgery when the inner sheath 204 is slid into the outer sheath 201. The sheath segment 204a has sharp teeth on its tip end, and a window 204d on the lateral wall close to the tip which will provide an observation means. The sheath segment 204a is made of a metal, and has an external diameter close to the internal diameter of the treatment channel 201a. The body 204b placed to the base of the sheath segment 204a has a hollow cavity, and has, within that cavity, an air-tight valve (not shown) such as a flap valve or a duckbill-valve. To the rear most end of the body 204b is attached a rubber cap 204f having an opening 204e.

A plug for the opening 204e is so constructed that, when a treatment tool belonging to this system is inserted therethrough, the plug can maintain air-tightness of the system. The body 204b also acts as a flange. The sheath segment 204a is so adjusted in its length with respect to the outer sheath 201 that, when the inner sheath 204 is inserted into the outer sheath 201 until the body 204b hits against the rear end of the outer sheath 201, the window 204d is positioned just beneath the transparent segment 201c prepared close to the tip of the outer sheath 201.

Next, the treatment tool system will be described. As shown in FIGS. 30–35, the treatment tool system consists of a drill, an intervertebral space opener, a reamer, a bone tap, an implant driver and an implant.

As shown in FIG. 30, the drill 207 is constituted with a handle 207a, a stem 207b and a drill cutter 207c. The handle 207a is placed normal to the stem 207b thus depicting a letter T. The stem 207b has an outer diameter close to the internal diameter of the treatment channel 201a of the outer sheath 201. The drill is as long as or longer than the outer sheath 201. To the tip of the stem 207b is attached the drill cutter 207c, and the long axis of the stem 207b is in alignment with that of the cutter. Close to the rear end of the stem 207c is placed a flange 207d. The drill cutter 207c has a smaller outer diameter than does the stem 207b.

As shown in FIG. 31A, the intervertebral space opener 208 is constituted with a stem 208a and an opener plug 208b. The stem 208a has a knurl 208c on its rear surface, and a thread 208d around its tip. The stem 208a has an outer diameter close to the inner diameter of the treatment channel 201a of the outer sheath 201. It has a length equal to or larger than that of the outer sheath. Close to the rear end of the stem 208a is placed a flange 208e. As shown in FIG. 31B, the opener plug 208b is constituted with a cylinder segment 208f and a cone segment 208g. The cone segment has its external wall so treated as to have a rough surface. The cylinder segment 208f has its rear end so processed that it has a hole there with a female thread 208h inscribed which corresponds with the male thread 208d prepared around the stem 208a. A plurality of opener plugs different in diameter by about 1mm are available to meet the demand from the operator according to the distance by which he wants to widen a given intervertebral space.

As shown in FIG. 32, the reamer 210 is constituted with a handle 210a, a stem 210b and a reamer cutter 210c. The handle 210a is placed normal to the stem 210b in the form of a letter T. The stem 210b has an outer diameter close to the internal diameter of the treatment channel of the inner sheath 204. It has a length equal to or larger than that of the outer sheath. To the stem 210b is placed the reamer cutter 210c, and the long axis of the stem 210b corresponds with that of the reamer. Close to the rear end of the stem 210c is placed a flange 210d. The reamer cutter 210c has a smaller outer diameter than does the stem 210b, and has a slightly larger diameter than does the drill-cutter 207c of the drill 207.

As shown in FIG. 33, the bone tap 211 is constituted from base to front with a handle 211a, a stem 211b, and a tap 211c. The handle 211a is placed normal to the stem 211b in the form of a letter T. The stem 211b has an outer diameter close to the internal diameter of the treatment channel of the inner sheath 204. It has a length equal to or larger than that of the inner sheath 204. To the stem 211b is placed the tap 211c, and the long axis of the stem 211b corresponds with that of the tap. The tap 211c has a smaller outer diameter than does the stem 211b, and is so constructed that, when applied to a hole prepared with the reamer 210, can make a hole with a thread.

Figure 34:
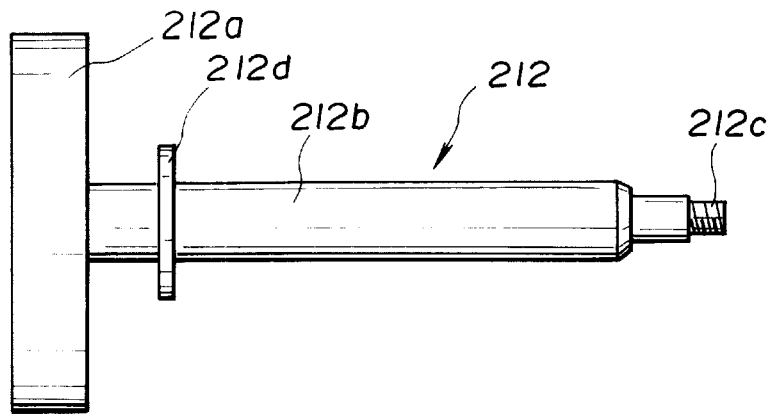

As shown in FIG. 34, the implant driver 212 is constituted from base to front with a handle 212a and a stem 212b. The handle 212a is placed normal to the stem 212b in the form of a letter T. The stem 212b has a male thread 212c on its front end. The stem 212b has an outer diameter close to the internal diameter of the treatment channel of the inner sheath 204. It has a length equal to or larger than that of the inner sheath 204. Close to the rear end of the stem 212b is placed a flange 212d.

Figure 35:
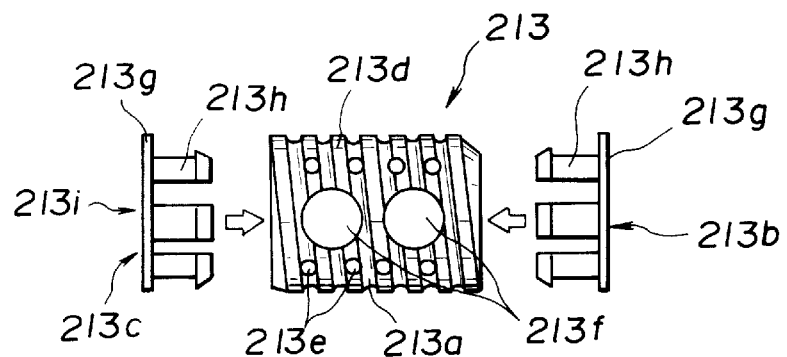

As shown in FIG. 35, the implant 213 is constituted with a body 213a in the form of a hollow cylinder, and a lower lid 213b and an upper lid 213c which are to be attached to both ends of the body. They are preferably made of titanium materials, ceramic materials, or apatite materials. The body 213a has on its outer surface a male thread 213d which corresponds with the female thread prepared with the bone tap 211 in the hole within an intervertebral disc. The body 213a has also on its surface many small holes 213e leading to the internal cavity, and big holes 213f which penetrate linearly through the core of the body. The lower and upper lids 213b and 213c are constituted each with a cap segment 213g and hooks shaped like nails 213h. When the lid is applied to the body, the hooks engage with the step prepared on the internal surface of the body 213a, and hence the lids 213a and 213c are so firmly fixed to the body that they will rarely fall therefrom. The internal cavity of the implant 213 is filled with a bone graft sampled from the patient himself, or a bone prosthesis made of β-TCP (calcium phosphate). At the center of the upper lid 213c there is a hole which has a female thread 213i corresponding with the male thread 212c placed around the tip of the implant driver 212c.

Next, the use of the implant guide sheath system in this embodiment will be described. Here as an illustration attention is paid to a case where two implants are introduced under endoscopic monitoring into a lumbar intervertebral disc.

Figure 36:
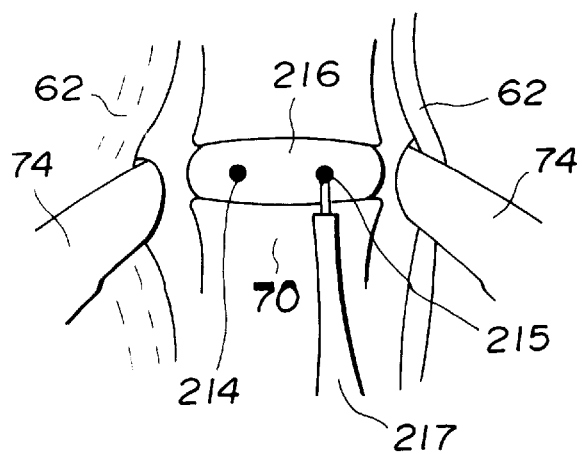
Figure 37:
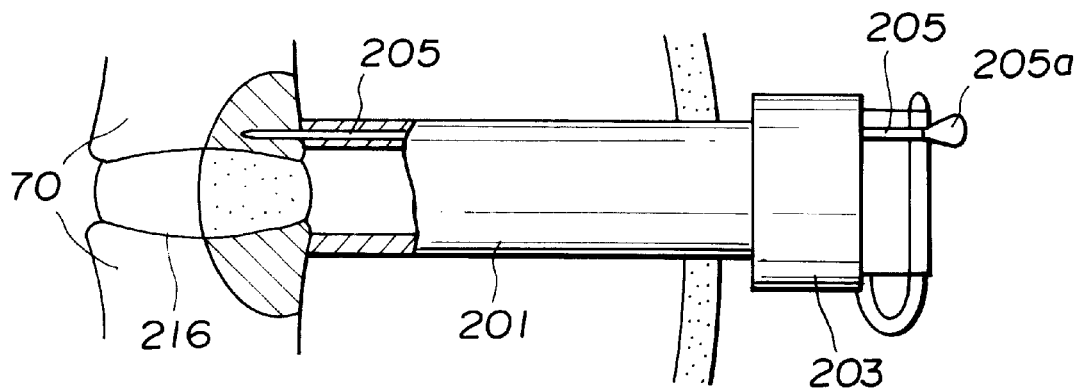
Figure 38:
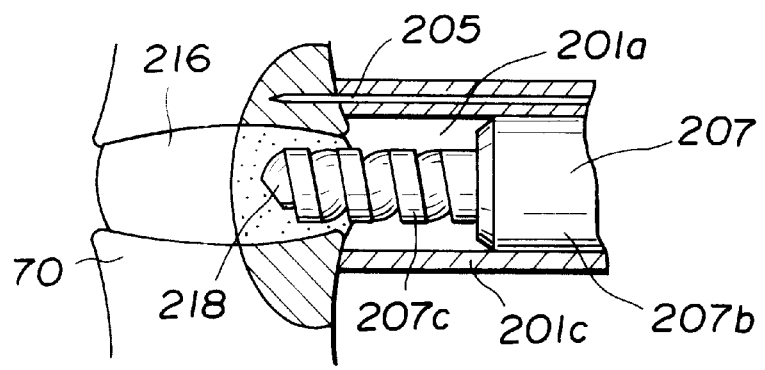

On the front aspect of lumbar vertebral bodies run aorta and inferior vena cava being placed one over the other, and the front aspect of the vertebral bodies is covered with major psoas muscles. Accordingly, to make a treatment safely on a vertebral body, it is necessary to push aside those vessels and muscles thoroughly to expose the complete aspect of the vertebral body of interest as described in the first embodiment. Then, in the same manner as in common endoscopic surgery, a pneumoperitoneum is made, trocars are inserted through the abdominal wall, treatment tools such as an laparoscope, grasping forceps 74, etc. are inserted into the body cavity through the trocars, and vessels and muscles 62 are pushed aside to expose the vertebral body of interest 70 and its surrounds (see FIG. 36). Then, as shown in FIG. 36, two dots are marked on an intervertebral disc 216 one 214 for the first implant and the other 215 for the second implant with a heating point from a high-frequency diathermy generator 217.

Then, an incision is made on the abdominal wall in such a manner as to allow the operator to approach the vertebral body of interest and to introduce the implants into it in an optimal way. Thus, a port for the introduction of the implant guide sheath is produced. The length of the incision is so adjusted as to maintain air-tightness of the body cavity after the outer sheath 201 of the implant guide sheath has been inserted into the body cavity. In place of incision, trocar perforation may be used for the same purpose: a plurality of trocars are prepared, a small-bore trocar is used to make a first hole, which is exchanged for a next larger trocar, and the same process is repeated until a sufficiently large hole for the entry of the implant guide sheath is formed.

At this stage, the mandrin 202 for expansion is inserted into the treatment channel 201a of the outer sheath 201, and the plugs 206 for spike channel are applied to the rear end of the spike channels 201d. Here the mandrin 202 for expansion is inserted down to such a level as to allow its flange 202d to hit against the rear end of the outer sheath 201. In this position, the O-ring 202f placed around the small-bore segment 202e of the mandrin 202 for expansion comes into close contact with the internal wall of the treatment channel 201a, thereby maintaining air-tightness between the treatment channel 201a and the mandrin 202 for expansion. Further, as the plugs 206 for spike channel with a tapered tip have been inserted sufficiently deep as to come into close contact with the terminal surface of the spike channels 201d, the spike channels are also kept air-tight.

Next, while the mandrin 202 for expansion is being firmly held so that it does not fall from the outer sheath 201, the tip of the mandrin 202 for expansion coming out from the tip of the outer sheath 201 is placed properly against the port prepared on the abdominal wall, and the system is pressed down through the port into the body cavity. As described above, as the treatment channel 201a of the outer sheath 201 and the spike channels 201d are kept air-tight, no leak of gas from the penumoperitoneum will occur.

After the outer sheath 201 has been inserted into the body cavity, the mandrin 202 for expansion is withdrawn, leaving the outer sheath 201 to be placed in the body cavity, and the cap 203 for outer sheath is applied to the rear end of the outer sheath 201. The cap 203 for outer sheath maintains air-tightness because its rubber cap opening 203 is closed with the plug segment 203f, and hence the outer sheath 201 is kept air-tight against atmosphere.

Next, the outer sheath 201 is rotated so that the escape 201b at the tip of the outer sheath 201 faces towards the vertebral body of interest, and is advanced until its tip 201 is so placed with respect to the vertebral body 70 that the tip surrounds the site 214 for the first implant within its confine.

Then, the plugs 206 for spike channels are removed, and spikes 205 are introduced instead into the spike channels 201d. The rear end of the spike 205 or the hold 205a is struck with a hammer to drive its tip into the vertebral body by a desired depth. Through this operation, the outer sheath 201 is stabilized while its tip being pressed against the vertebral body 70. The spike channels 201d are closely placed to each other in the outer wall of the outer sheath 201. Accordingly, the two spikes 205 are driven into the one and same vertebral body upper or lower from an intervertebral disc of interest as the case may be. Thus, when the intervertebral space is opened as will be described later while the outer sheath 201 is stabilized against a vertebral body 70, no tool will get in the way of operation.

In this embodiment, even when the spike 205 is inserted until its hold 205a hits against the rear end of the outer sheath 201, the tip of the spike 205 will come out from the tip of the outer sheath 201 only by about 1.5 cm, and hence it will not inflict damages upon organs situated 1.5 cm or more apart from it. As seen from FIG. 37, fixing the outer sheath 201 against the vertebral body 70 through close contact will prevent adjacent organs from entering into the internal cavity of the outer sheath 201 and dispense with the work necessary for rejection of those organs once the outer sheath 201 has been stabilized. Accordingly, following operations to be executed in the internal cavity of the outer sheath 201 will become easier with this system.

The rubber cap plug segment 203f of the cap 203 for the outer sheath is removed, and the drill 207 is inserted instead into the treatment channel 201a of the outer sheath 201. While the drill 207 is being pressed against the vertebral body 70, the handle 207a is turned round to make a hole 218 which is to receive an implant 213 for the intervertebral disc 216 (see FIG. 38). During this operation, as the stem 207b of the drill 207 has the same diameter as does the treatment channel 201a of the outer sheath, the central axis of the drill 207 will stay constant even when the drill is put into rotation, which ensures the stable operation of the drill. When a hole 218 is opened to a desired depth, the flange 207d placed around the stem 207b of the drill 207 hits against the rear end of the outer sheath 201, to block the further advancement of the drill. Accordingly, there will be no risk involved in the drill operation of making a too deep hole 218 in the vertebral body, such as injuries on the spinal cord. While the drill 207 is kept inserted in the treatment channel 201a, the internal cavity within the outer sheath 201 maintains air-tightness through the rubber cap 203d.

How the drill work proceeds within the outer sheath 201 can be monitored with a laparoscope through the transparent segment 201c prepared at the tip of the outer sheath 201. Accordingly, if adjacent organs enter by accident into the internal cavity of the outer sheath 201 during drill operation, it will be possible to immediately stop the drill work and to reject those organs before resuming the work. This ensures safe drill operation.

Figure 39:
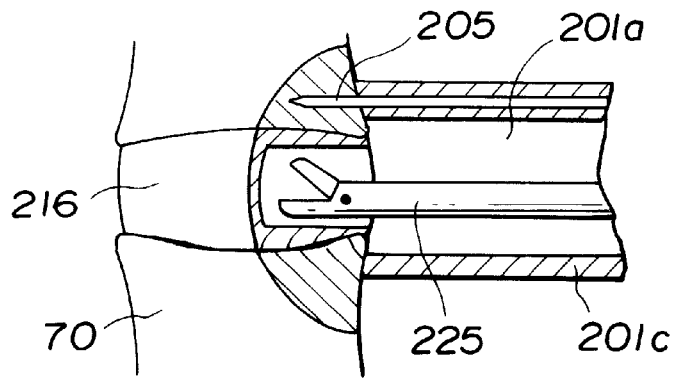

The drill 207 is withdrawn from the outer sheath 201, and a curette or a sharply pointed scissors 225 is inserted into the hole 218 prepared with the drill, to remove the medullar nucleus and fibrous ring constituting the substance of the intervertebral disc 216 (see FIG. 39). Sufficient removal of the medullar nucleus and fibrous ring will ensure the safe introduction of the implant 216 into the intervertebral space 216. This operation can be monitored with a laparoscope as is described above. During this operation, the internal cavity of the outer sheath 201 remains air-tight through the action of the rubber cap 203d.

Figure 40A:
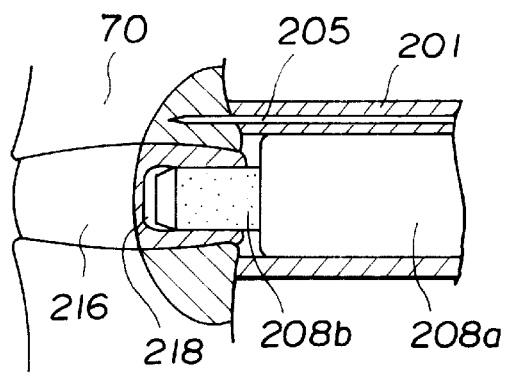
FIG. 40A illustrates how the opening plug is driven into the hole prepared by the drill.
Figure 40B:
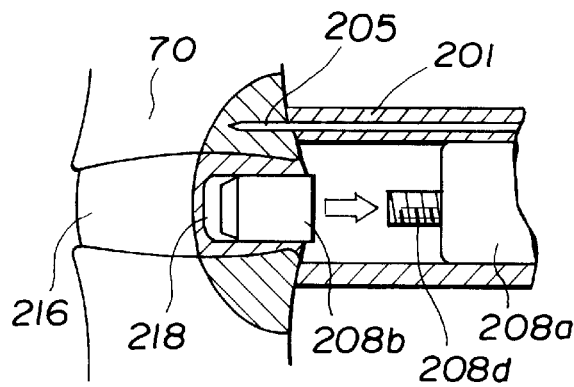
FIG. 40B illustrates how the opening plug is left in the hole prepared by the drill.
Figure 41:
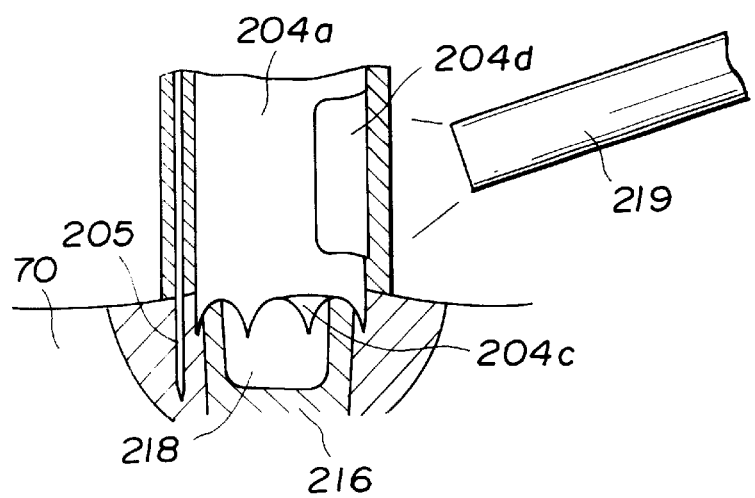
Figure 42:
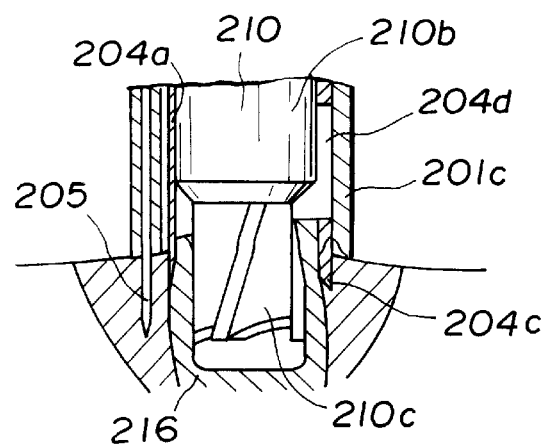
Figure 43A:
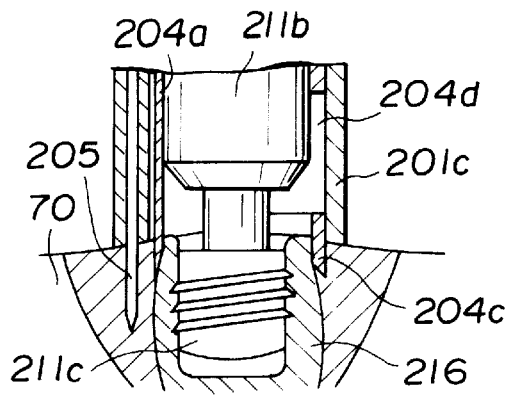
FIG. 43A illustrates how a thread has been cut on the internal surface of the hole.
Figure 43B:
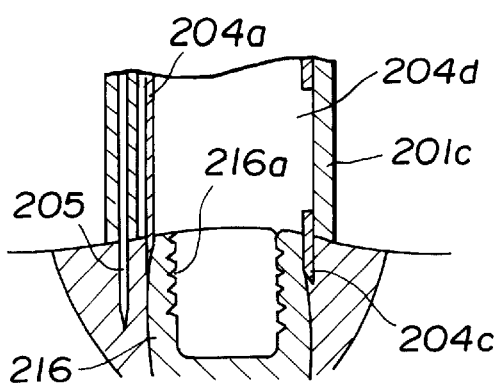
FIG. 43B illustrates how cutting of threads on the internal surface of the hole is completed.
Figure 44A:
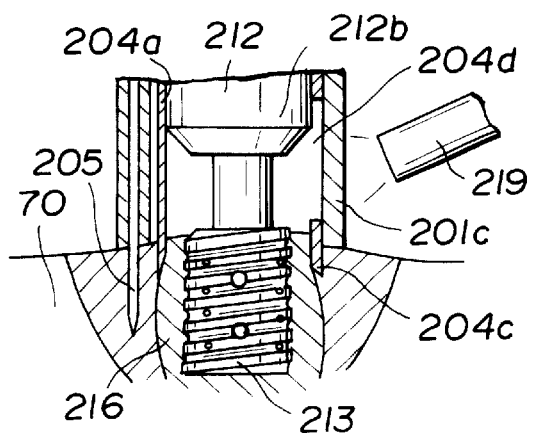
FIG. 44A illustrates how an implant is screwed into the hole.
Figure 44B:
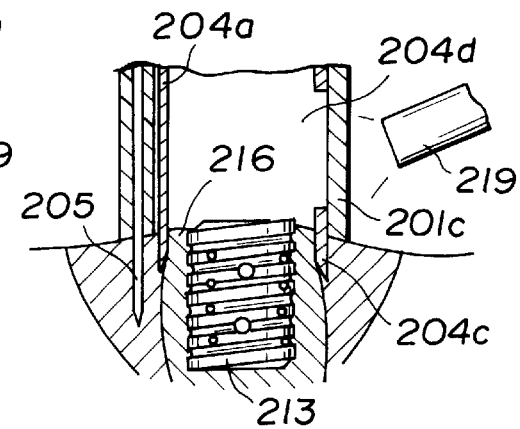
FIG. 44B illustrates how the implant is left in the intervetebral space.

Next, the intervertebral space opener 208 is introduced into the treatment channel 201a of the outer sheath 201, and the rear end of the stem 208a of the opener 208 is struck with hammer to advance the opener plug 208b into the hole 218 until the flange 208e placed around the stem 208a hits against the rear end of the outer sheath 201 (see FIG. 40A). A plurality of opener plugs are available which are different in diameter by about 1 mm, and an appropriate plug is chosen to give a desired opening.

As the stem 208a of the intervertebral opener 208 has a diameter close to that of the outer sheath 201a, only insertion of the intervertebral opener 208 into the treatment channel 201a of the outer sheath will allow automatically the central axis of the hole 218 to correspond with the central axis of the opener plug 208b. This dispenses with the work necessary for alignment of the opener plug 208b with the hole 218. Further, as the opener plug 208 is prevented from advancing further when the flange 208e hits against the rear end of the outer sheath 201, there will be no danger of advancing the opener too far into the vertebral body by accident.

Further, as the opener plug 208b has a cone segment 208g at its tip, it can be smoothly inserted into the intervertebral disc 216. Furthermore, as the opener plug 208b has its cylinder segment 208f so treated as to give a rough surface, the segment is prevented from slipping, and hence the opener plug 208b, once it is driven into the intervertebral space, will not fall easily. Once the opener plug 208b has been driven sufficiently deep into the intervertebral disc 216, the stem 208b is unscrewed from the stem 208a and the plug opener 208b, leaving the plug opener 208b placed in the intervertebral disc 216 (see FIG. 40B). How the plug 208b is driven into the intervertebral disc can be also monitored with a laparoscope through the transparent segment 201c prepared at the tip of the outer sheath 201. Further, while the intervertebral opener 208 is being inserted into the treatment channel 201a, the internal cavity of the outer sheath 201 remains air-tight through the action of the rubber cap 203d.

At this stage, the rubber cap opening 203e of the outer sheath cap 203 is closed with the plug segment 203f, and the spikes which have been inserted through the spike channels 201d and driven into the vertebral body 216 are withdrawn, thereby releasing the fixation of the outer sheath 201 to the vertebral body 216. Then, the outer sheath 201 is allowed to place its tip 201 with respect to the vertebral body 70 such that the tip surrounds the site 216 for the second implant within its confine, and, in the same manner as describe above, is stabilized against the vertebral body 70 by driving the spikes 205 into that body. The same preparation as described above is made for the insertion of the second implant: drill works, and removal of medullar nucleus and fibrous ring with a curette or a scissors 225. The operation is also monitored with a laparoscope as described above. Further, during this operation, the internal cavity of the outer sheath 201 maintains air-tightness through the action of the rubber cap 203d.

Next, the inner sheath 204 is inserted into the treatment channel 201a of the outer sheath, and the rear end of the inner sheath 204 is struck with a hammer to drive the teeth 204c on the terminal end of the inner sheath 204 into the vertebral body 70. During this operation, the window 204d of the inner sheath 204 is placed at the center of the visual field of the laparoscope, and under endoscopic monitoring, the inner sheath is driven until the body 204b of the inner sheath hits against the rear end of the outer sheath 201. This operation is made possible by placing the transparent segment 201c of the outer sheath 201 over the window 204d of the inner sheath 204, and by monitoring, for example, with a laparoscope 219 how operation proceeds in the work space within the inner and outer sheaths 201 and 204 (see FIG. 41).

As seen above, as the inner sheath 204 is driven into the vertebral body 70 under endoscopic monitoring, and hence, the fixation of this sheath system to the vertebral body 70 is further strengthened, there will be no danger that the sheath system will fall from the vertebral body during operation.

Further, while the inner sheath 204 is being stabilized against the vertebral body 70, the rubber cap 203d of the outer sheath cap 203 ensures air-tightness of the space between the inner and outer sheaths 203 and 204, and further while the treatment channel of the inner sheath 204 is kept vacant without receiving a treatment tool, the air-tight valve installed in the body 204b of the inner sheath is activated to keep air-tightness of the inner sheath 204, and still further while a treatment tool is kept inserted into the treatment channel, the rubber cap 204f at the rear end of the inner sheath 204 prevents leakage of gas from the pneumoperitoneum prepared in the body cavity. Further, after the inner sheath 204 has been stabilized, the outer sheath 201 remains stabilized against the vertebral body 70. This arrangement prevents adjacent organs from entering through the window 204 of the inner sheath 204 into the work space.

Then, the reamer 210 is inserted into the treatment channel of the inner sheath 204, and the reamer 210c is allowed to enter into the hole 218 prepared in the intervertebral disc 216. The reamer 210 is advanced through the rotation of the handle 210a until the flange 210d placed around the stem 210b of the reamer 210 hits against the rear end of the inner sheath 204, to finish the hole 218 (see FIG. 42)

As the stem 210a of the reamer 210 has a diameter close to that of the inner sheath 204, only insertion of the reamer into the treatment channel of the inner sheath 204 will allow automatically the central axis of the hole 218 to correspond with the central axis of the reamer 210. This dispenses with the work necessary for alignment of the reamer 210 with the hole 218. Further, as the reamer is prevented from advancing further when the flange 210d hits against the rear end of the inner sheath 204, there will be no danger of advancing the reamer 210 too far into the vertebral body by accident and inflicting injuries on the spinal cord.

As seen from above, as the reamer 210 can finely finish the hole 218, it is possible to make a hole having an optimum size for receiving the implant 213, and thereby to ensure secure fixation of the implant in the intervertebral space 216.

After the reamer operation has been finished, the bone tap 211 is inserted into the treatment channel of the inner sheath 204, and the tap segment 211c is inserted into the hole 218. Then, the bone tap handle 211a is turned round to drive the tap segment into the hole until the flange 211d placed around the stem 211b of the bone tap 211 hits against the rear end of the inner sheath 204. Through this operation, on the internal surface of the hole 218 prepared in the vertebral body 70 is formed a thread 216a which serves as a guide when the implant 213 is screwed into the hole 218 (see FIGS. 43A and 43B).

As the stem 211b of the bone tap 211 has a diameter close to that of the treatment channel of the inner sheath 204, only insertion of the bone tap 211 into the treatment channel of the inner sheath 204 will allow automatically the central axis of the hole 218 to correspond with the central axis of the bone tap 211. This dispenses with the work necessary for alignment of the bone tap 211 with the hole 218. Further, as the bone tap 211 is prevented from advancing further when the flange 211d hits against the rear end of the inner sheath 204, there will be no danger of advancing the bone tap 211 too far into the vertebral body by accident and inflicting injuries on the spinal cord.

As seen from above, as the bone tap 211 prepares a thread 216a on the hole 218 which will not only enable smooth screwing in of the implant 213, but also prevent erratic insertion of the implant 213 such as insertion from a wrong angle or too deep insertion. Thus, through this operation, the implant 213 can be placed most properly in the intervertebral disc 216.

Next, the implant 213 is screwed to the tip of the implant driver 212. The implant 213 attached to the implant driver 212 is inserted into the treatment channel of the inner sheath 204. The implant is inserted into the hole 218. The implant driver handle 212 is turned round to drive the implant 213 into the hole 218 until the flange 212d placed around the stem 212b of the implant driver 212 hits against the rear end of the inner sheath 204 (see FIG. 44A).

The depth by which the implant 213 is driven into the intervertebral disc 216 is limited by the flange 212d placed around the stem 212b of the implant driver 212. This not only ensures safe and proper placement of the implant in the intervertebral cavity, but also avoids the danger of digging a too deep hole, and thereby inflicting injuries on the spinal cord. Further, as the stem 212b of the implant driver 212 has a diameter close to that of the treatment channel of the inner sheath 204, only insertion of the implant driver 212 into the treatment channel of the inner sheath 204 will allow automatically the central axis of the hole 218 to correspond with the central axis of the implant driver 212. This dispenses with the work necessary for alignment of the implant 213 with the hole 218.

When the implant 213 is left in place, the implant is preferably so positioned as to allow the big holes 213f to face the end surfaces of the upper and lower vertebrae. At this stage, the implant driver 212 is unscrewed from the implant 213, to leave the implant 213 alone in the intervertebral disc 216 (see FIG. 44B). The above operation completes the work necessary for implantation of the second implant 215.

Such placement of the implant 213 with respect to the intervertebral disc 216 ensures not only safe and easy placement of the implant 213 in the intervertebral disc 216, but also readier bone fusion and reinforcement of intervertebral connection, because the bone graft or prosthetic bone contained in the implant 213 will fuse more easily through big holes 213f with surrounding bony tissues from upper and lower vertebrae.

Next, the inner sheath 204 is withdrawn, and the rubber cap 203d of the cap 203 for outer sheath is applied for closure. Then, the spikes 205 driven into the vertebral body 70 are withdrawn to relieve the outer sheath 201 from fixation to the vertebral body 70. Then, the outer sheath 201 is allowed to place its tip 201 with respect to the vertebral body 70 such that the tip surrounds the site 214 for the first implant within its confine, and, in the same manner as describe above, is stabilized again against the vertebral body 70 by driving the spikes 205 into the body 70.

The stem 208a of the intervertebral opener 208 is inserted into the treatment channel 201a of the outer sheath, the male thread 208d around the tip of the stem 208a is screwed, engaging with the female thread 208h, into the opener plug 208b resting in the intervertebral space, and the opener plug 208b is withdrawn from the intervertebral space after the stem 208a is firmly held and pulled out. While the stem 208a is being screwed into the opener plug 208b, the operation can be watched by endoscopy through the transparent segment 201 prepared at the tip of the outer sheath 201. This ensures smooth operation.

The inner sheath 204 is inserted into the treatment channel 201 of the outer sheath 201, and the rear end of the inner sheath 204 is struck with a hammer to advance the inner sheath until the teeth prepared on the terminal end of the inner sheath 204 penetrate into the vertebral body 70. During this operation, the window 204d of the inner sheath 204 is placed at the center of the visual field of the laparoscope as described above. The same operation is applied for the site 214 for the first implant as in the second implant, including reamer woks, bone tap works, and implantation of the implant. This completes the work necessary for the implantation of the two implants.

Figure 45:
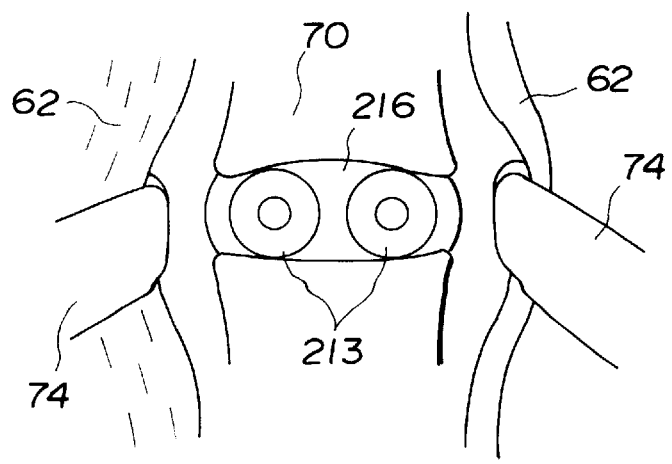

When the two implants 213 have been implanted into the vertebral body 70, they are placed parallel to each other (see FIG. 45). This arrangement allows the implants to securely sustain the weight of vertebral body 70 even when the patient stands upright. As the implants 213 have been narrowly inserted into the space opened by the plug opener 208b, they are securely fixed after operation by the pressure from upper and lower vertebrae, and the fixation is further strengthened by screws. Thus, they will never fall from the intervertebral disc 216 after operation.

As seen from above, as this embodiment allows the implant guide sheath to act also as a fitting means to the vertebrate body 70, the work involved in the rejection of adjacent organs after fixation of the sheath becomes unnecessary. Accordingly, there is no danger, after fixation of the implant guide sheath to the vertebrate body 70, of inflicting damages to nearby organs. Particularly as this embodiment uses the inner sheath 204 with teeth 204c on its terminal end which fixes against the vertebral body 70 by driving the teeth into the vertebral body 70, fixation of the sheath system to the vertebral body 70 is further strengthened, and danger that the sheath system may fall by accident from the vertebral body 70 during operation will be negligible. Thus, when this implant guide sheath system is used, attention is more directed towards the operation itself. When the touter sheath 204d is allowed to stabilize against the vertebral body 70 after the inner sheath 204 has been stabilized against the vertebral body 70, it is possible to prevent adjacent organs from entering into the internal work space through the window 204d of the inner sheath 204.

As the space between the outer and inner sheath 201 and 204 is kept air-tight by the action of the rubber cap 203d of the cap 203 for outer sheath, gas from the pneumoperitoneum is prevented from escaping even after the inner sheath 204 has been stabilized against the vertebral body 70. This also prevents blood and other liquids from bursting, with gas from the pneumoperitoneum, into the internal cavity within the treatment channel of the inner sheath. Thus, the good view of the internal cavity will not be interfered.

As the observation means is available by which to endoscopically observe, through the transparent segment 201c and the window 204d of the inner sheath, how operation proceeds in the internal cavity of the sheath, and hence safety can be checked even if adjacent organs invade by accident from the gap between the sheath and the vertebra 70 into the internal cavity, danger of inflicting damages on those organs will be negligible. Particularly, when medullar nucleus and fibrous ring are removed from the intervertebral disc 216, when the depth of the opener plug 208b and the implant 213 is checked, or when the stem 208b of the intervertebral opener 208 is screwed into the opener plug 208b, to recover the plug 208b from the intervertebral disc 216, this system allows the operation to proceed under endoscopic monitoring. This ensures safe and smooth operation.

As the treatment tools used in this system are designed to have the same diameter with that of the outer sheath 201 or inner sheath 204, only insertion of the treatment tool into the treatment channel will allow automatically the central axis of the hole 218 to correspond with the central axis of the treatment tool. This dispenses with the work necessary for alignment of the treatment tool with the hole 218, or eliminates the possibility of enlarging the hole because the two central axes are not in alignment.

The treatment tool of this treatment tool system has a flange close to the base end of the stem. This arrangement limits the tool to move further when the flange hits against the rear end of the sheath, which will not only allow the tool to be placed to a desired position but also prevent it from advancing too far, and thus from inflicting undue damages on the spinal cord.

The twelfth embodiment of this invention will be described with reference to FIGS. 46 and 47.

The sheath system of this embodiment is similar to the eleventh embodiment except that it lacks the inner sheath 204. Accordingly, the reamer 210, bone tap 211 and the stem of the implant driver 212 are designed to have the same diameter with that of the treatment channel 210a of the outer sheath. The flange placed around the stem of each tool is so designed as to allow the tool to reach an appropriate position with respect to the intervertebral body when the flange hits against the rear end of the outer sheath 201.

Figure 46:
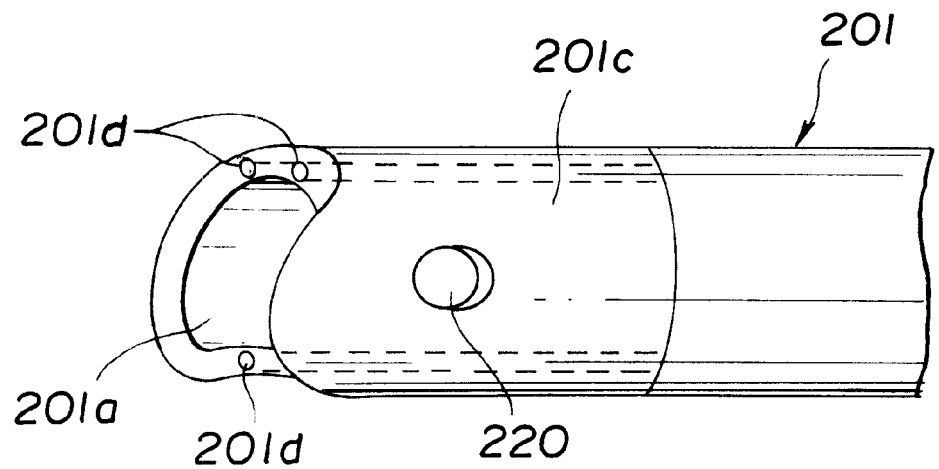
FIGS. 46 and 47 refer to the twelfth embodiment of this invention.
Figure 47:
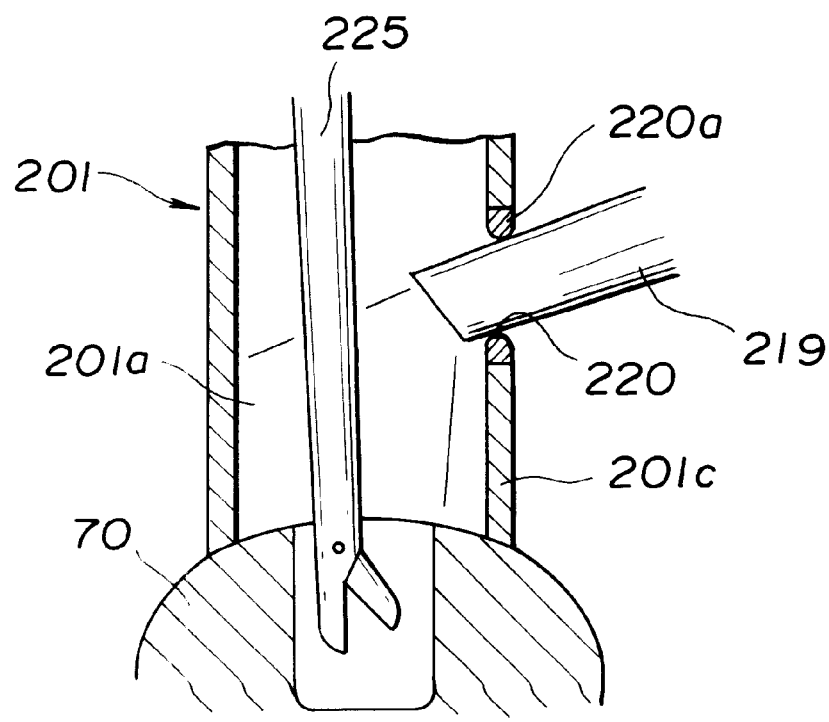

As shown in FIG. 46, besides the two spike channels 201d placed closely to each other, another spike channel 201d is prepared in the outer wall of the outer sheath 201. Thus, the outer sheath 201 has three spike channels 201d in total. The three spike channels 201d are so placed relative to each other that their summits form a triangle when seen from the tip. In association, the spikes 205 and plugs 206 for spike channel are prepared by three for this sheath system.

The outer sheath of this embodiment is provided with a flanking means close to the tip to facilitate endoscopic monitoring. The flanking means is to receive the insert of a scope 219 such as a laparoscope. Namely, the outer sheath 201 has a round hole close to the tip, and, as shown in FIG. 47, the periphery of the hole is surrounded by an elastic material 220a made of a rubber material. The internal diameter of the round hole 220 is so adjusted as to allow the insert of the scope 219 to be freely inserted and removed, and to be securely fixed once the scope 219 is put into a proper place. The rubber cap attached to the outer sheath has a diameter which ensures air-tightness when a treatment tool properly adapted for the present system is inserted through. Otherwise, the constitution is the same as in the eleventh embodiment.

This embodiment can be used in the same manner as in the eleventh embodiment. Firstly, the outer sheath 201 is allowed to place its tip with respect to the vertebral body 70 such that the tip surrounds the site 214 for the first implant within its confine, which is followed by drill operation, intervertebral opening, and implantation of the implant. Up to this stage, the sheath is stabilized by inserting two spikes only into the upper vertebral body 70a. Then, before the second implant 215 is implanted into the site 215, in addition to the two spikes driven into the upper vertebral body 70a, a third spike 205 is driven into the lower vertebral body 70b, to further fix the outer sheath 201 securely against the vertebral bodies 70.

Next, when the outer sheath 201 is fixed again this time with respect to the site 214 for the first implant, three spikes are also used: two spikes into the upper vertebral body 70a and a third spike into the lower vertebral body 70b. As seen from above, as the number of spikes used is varied according to the type of necessary operation, the intervertebral disc 216 can be opened without interfering with the fixation of the outer sheath 201 against the vertebral body 70, and this further strengthens the fixation of the sheath against the vertebral body 70 through operation.

Works involving the use of reamer 210, bone tap 211 and implants 213 are executed in the treatment channel 201a of the outer sheath. The flange placed around the stem limits the tool to move further when it hits against the rear end of the sheath, which will not only allow the tool to be placed to a desired position with respect to the vertebral body 70, but also prevent it from advancing too far, and thus from inflicting undue damages on the spinal cord.

To observe how operation proceeds in the cavity within the sheath, it is necessary to insert the insert of the scope 219 through the round window 220 prepared at the tip of the outer sheath 201 and fix it in a proper place. Alternatively, the endoscopic monitoring may take place not through the round window 220 but through the transparent segment 201c prepared at the tip of the same sheath.

As seen from above, as this system dispenses with the use of the inner sheath 204, it can improve efficiency in operation and cost performance of the system. Further, as the spike 205 has such a small diameter that the damage it will inflict upon the vertebral body 70 is far less than that caused by the teeth prepared on the end of the inner sheath 204, bleeding from the spongy portion of the vertebral body 70 will be slight.

The observation means of this embodiment does not consist of watching through the transparent segment 201 prepared on the outer sheath 201, but of viewing directly the internal cavity with a scope inserted through the window. This ensures stable and clear visibility of the operation site, and keeps the visibility from being impaired by soils from blood and fat adhering to the transparent segment 201c, and once the scope 219 has been inserted through the outer sheath 201 and put in a proper place, it is unnecessary to hold the scope, which dispenses with the work necessary for the fixation of the scope 219. This will help to lessen the burden imposed on the operator. Ready fixation of the scope 219 with respect to the outer sheath 201 ensures a stable and constant visual field.

In place of the elastic member 220a placed around the round window 220 prepared at the tip of the outer sheath 201, a magnetic body may be used. This arrangement allows the scope 219, once it is inserted through the round window 220, to be fixed with respect to the outer sheath by magnetism from the magnetic body. Further, as the outer tube of an endoscope commonly used for endoscopic surgery is made of steel, the magnetic body, when properly chosen, is attracted to that tube with a sufficiently strong force.

When the magnetic body is employed as a bonding means for the scope 219, it becomes unnecessary to push the scope 219 through the round window, and hence the scope can be more smoothly attached to or detached from the outer sheath. Further, as the magnetism in the magnetic body 220b is scarcely consumed, repeated use of the magnetic body will not lessen the bonding activity towards the scope 219. Otherwise, the effects are similar to those in the third embodiment.

The thirteenth embodiment will be described with reference to FIGS. 48–53.

The sheath system for vertebral surgery of this embodiment is principally used for the case where it is necessary to dorsally approach a lumber vertebra by separating muscles, to reach a vertebral arch, and then to remove a herniated intervertebral disc. The present system is for dorsal approach from the left side of spinous processes.

As shown in FIG. 48, a sheath for surgery 230 is constituted with a cavity-retaining means 231 (to be referred to as a cavity-retaining segment or ring member) which is prepared at the tip and is shaped like a ring, a handling member 232 which acts as a positioning means of the sheath for surgery 230 which extends from one end of the ring member 231, and a soft sheet member 233 which is connected to the cavity-retaining segment 231.

The cavity-retaining segment 231 is made of a rigid or semi-rigid material shaped like a ring with a certain width. The tip of this cavity-retaining means 231 is so shaped as to correspond with the shape of the bone between adjacent vertebral arches to which it is applied, so that it can be securely fixed to that bone.

To be more concrete, as shown in FIG. 49, the cavity-retaining segment 231 has one part of its tip protruded in such a manner that its contour can snugly fit to a lower vertebral arch, and another part cut obliquely in such a manner that the remaining contour can correspond with a spinous process. Further, the part corresponding with the upper vertebral arch has a concave surface. The soft sheet is omitted from the figure.

The handling member 232 which also acts as a positioning means of the sheath for surgery 230 is made of a rigid member which extends from one end of the ring member 231. It has a bend close to the base, and a handle 234 at the base.

The soft sheet member 233 is made of a soft material like rubber and is shaped like a tapered funnel, and is connected to the cavity-retaining segment 231 as if to cover the perimeter of the latter. This soft sheet member communicates with the internal cavity of the ring member 231, and forms a treatment channel during operation. In short, the soft sheet member 233 provides a means through which tools are guided into the cavity surrounded by the cavity-retaining segment 231, and forms a channel 235 for tool insertion.

Figure 52:
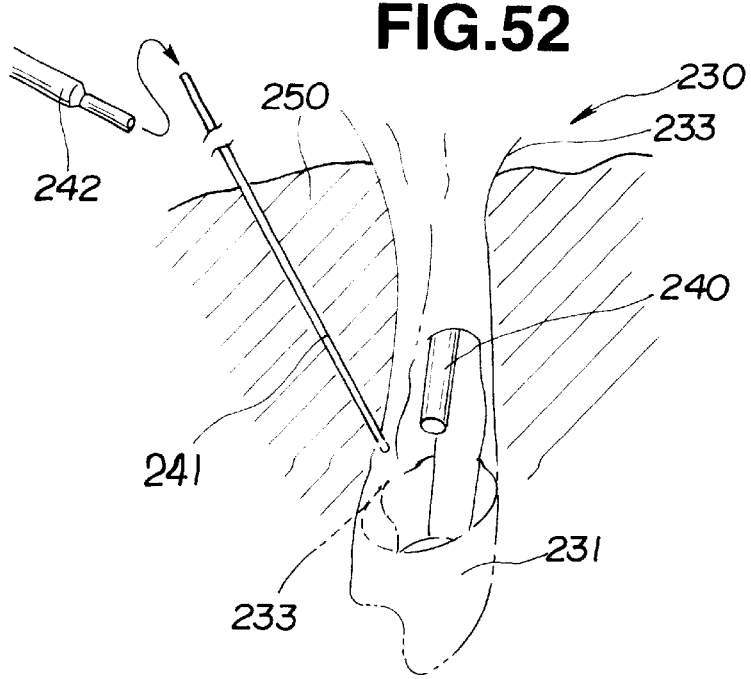
Figure 53:
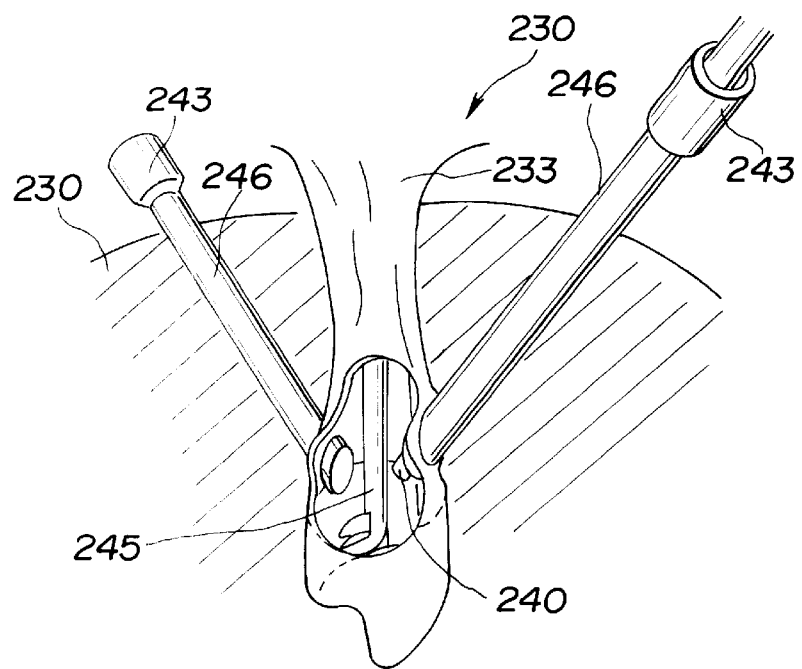

In this embodiment, trocars can be used. The trocar is constituted with a guide needle 241, a dilator 242 and a trocar port 243 as shown in FIGS. 52 and 53. The trocar port 243 is so made as to narrowly slide over the maximum bore of the dilator 242, and to allow an endoscope, or other treatment tools to pass through. The tip has an obliquely cut end.

This embodiment is provided with the dilator 242 which helps the trocar to be introduced into deeper parts of the body. The dilator 242 is the same as the commonly used antenna type dilator, and is constituted with a guide needle 241 and a cylinder member (not shown) which consists of different cylinder segments having diameters increasing stepwise in an ascending order. The cylinder part whose diameter is the smallest can narrowly slide over the guide needle 241. The cylinder segment whose diameter is the largest can slide narrowly under the sheath 230 for surgery. In case it is difficult to drive the sheath 230 for surgery into the body, cylinder segments which can slide over the dilator with the maximum diameter may be prepared, to further separate underlying tissues.

The monitoring in this embodiment takes place by endoscopy. The scope is inserted through the channel 235 for tool insertion which is constituted by a soft sheet member 233 within the sheath 230 for surgery. As described later, the scope can be inserted through a trocar which has been inserted through the soft sheet member 233 (see FIG. 53).

The sheath system for surgery having the constitution as described above will be described.

Firstly, the guide needle 241 is inserted towards a vertebral arch of interest. This operation may be performed while being monitored under X-ray photography or ultransonography. Once the needle has been inserted close to the vertebral arch, the dilator 241 with cylinder segments is inserted stepwise with the guide needle as a guide, thus separating body tissues increasingly. When the cylinder segment with the maximum diameter has been inserted, the sheath 230 for surgery is allowed to slide over the cylinder segment, and the assembly is allowed to advance until the tip hits against a bone (see FIGS. 50A and 50B). In case it is difficult to drive the sheath 230 for surgery into the body, a cylinder segment which can slide over the dilator with the maximum diameter may be inserted to further expand the perforation. Then, only the last cylinder is withdrawn, and the sheath 230 for surgery is inserted instead.

Figure 50A:
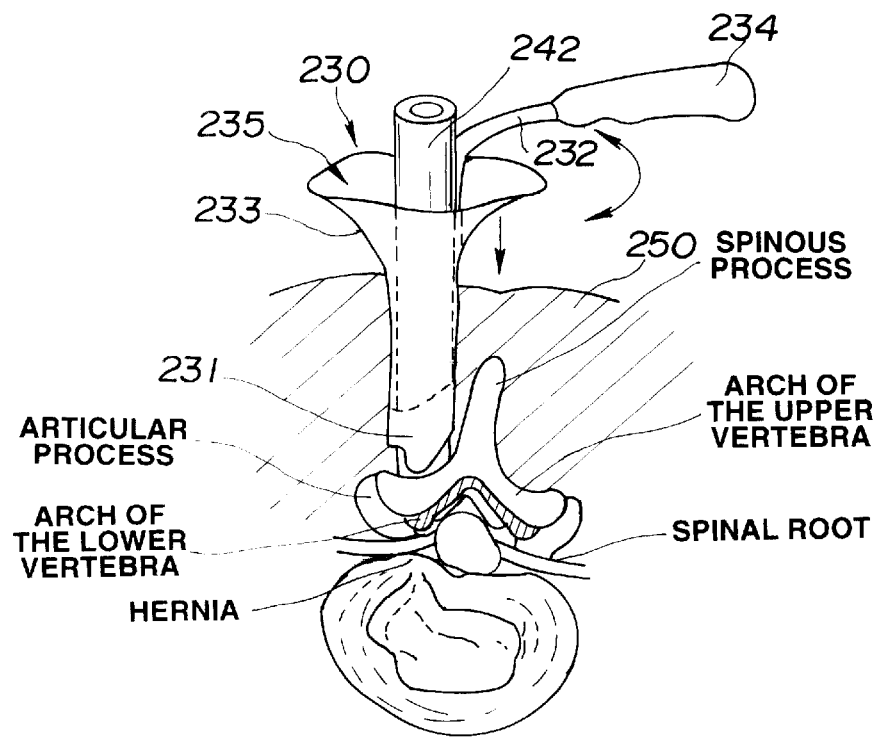
FIG. 50A illustrates how the sheath is introduced into a place of interest.
Figure 50B:
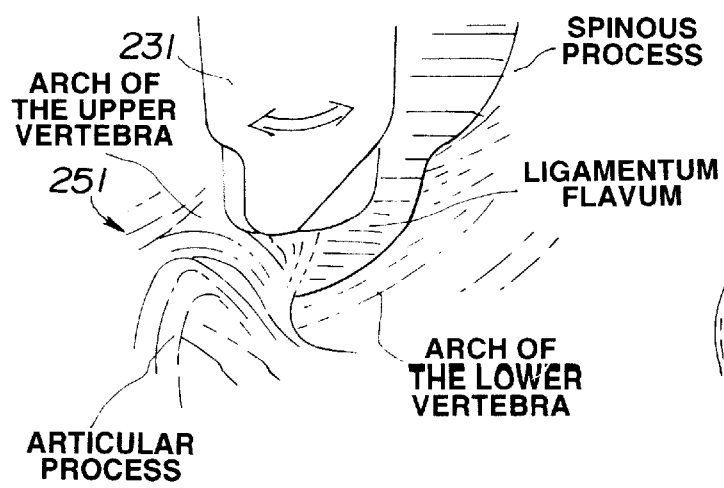
FIG. 50B illustrates how the tip of a cavity-retaining segment comes into contact with a bone, and probes to seek a proper place.
Figure 50C:
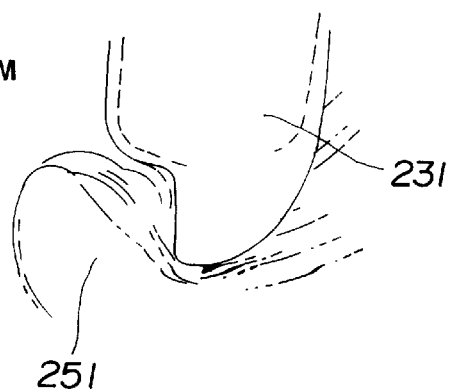
FIG. 50C illustrates how the tip of the cavity-retaining segment is put into a proper place.

The sheath 230 for surgery has a tip so shaped as to allow it to fit snugly against the bone between adjacent vertebral arches. Thus, as shown in FIG. 50B, while the sheath 230 for surgery is pressed against the bone, it is allowed to rotate or displace until it is most deeply pushed in and most securely fixed. At this position the tip of the sheath fits snugly to the vertebral arch 251, as shown in FIG. 50C. Thus, with this system, positioning of the sheath is comparatively easy, because the displacement of the sheath in the depth direction will give a proper position for the sheath. At this stage, the core needle is withdrawn, and the direction of the sheath 230 for surgery is adjusted until the sheath is securely stabilized. At this state, the sheath 230 practically corresponds with the vertebral arch 251 of interest.

Because the tip of the cavity-retaining segment 231 is similarly shaped to the contour of the vertebral arch 251, even if the guide needle is inserted from a wrong angle, the sheath 230 for surgery can be guided to a desired position on the vertebral arch 251 of interest. When the cavity-retaining segment 231 is made of a semi-rigid material, the round cavity (or the internal cavity of the cavity-retaining member 231) contacting with the bone can deform more or less. Thus, by manipulating the handling member 232 so that the sheath 230 for surgery can be pressed against the bone, it is possible to fit the sheath more securely to the bone.

Next, an endoscope 240 and treatment tools 245 are inserted from the rear end of the soft sheet member 233, to remove body tissues including muscles adherent to the vertebral arch in front of the cavity-retaining segment 231, thereby to expose the bone between vertebral arches.

Figure 51:
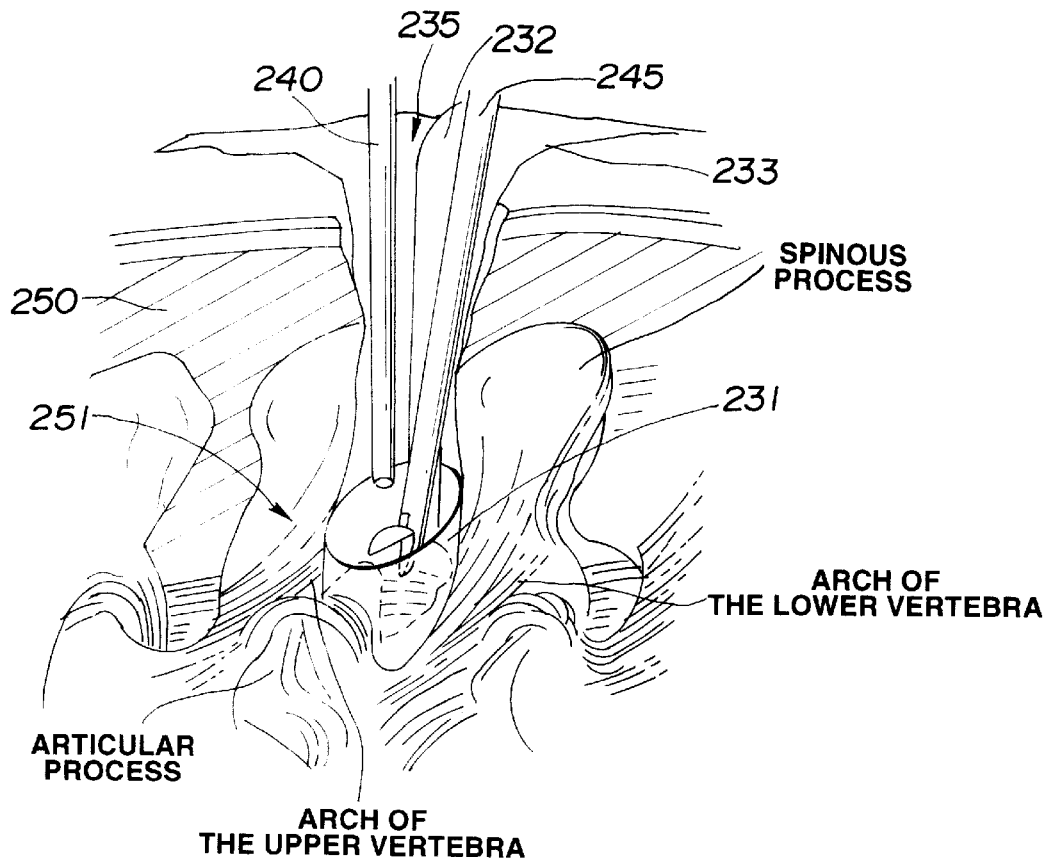

At this stage, body tissues are pushed aside from the frontal aspect of the vertebral arch by the cavity-retaining segment 231, and the work space for surgery is ensured (see FIG. 51). From the cavity-retaining segment 231 extends outward the soft sheet member 233. This outward extending soft sheet member 233, because of its yielding nature, collapses in the face of pressure from body tissues.

However, as the sheath 230 for surgery is a cylinder member in the form of a sheet, and the channel 235 for tool insertion which communicates with the cavity retained by the cavity-retaining segment 231 is formed, the channel for passage of tools is maintained. Thus, as long as body tissues are sustained by operation tools 240 such as an endoscope and treatment tools 245 inserted into the channel, other treatment tools can be inserted easily. Because the sheath 230 for surgery and the channel 235 for tool insertion are soft in nature, tools can be inserted from any desired angles and they can be handled easily not being disturbed by the sheath 230. Further, as shown in FIG. 51, with such constitution, tools can be easily inserted into the cavity and they scarcely interfere with each other during insertion and handling. Still further, as the soft sheet member 233 does not positively reject surrounding tissues, it will not inflict serious damages to nearby muscles.

A case will be described with reference to FIGS. 52 and 53 where an operation involving the use of various treatment tools is performed similarly to the common removal of a hernia.

When tools interfere with each other to hinder the progress of operation, trocars 246 may be used in addition. This is done as follows: firstly a guide needle 241 is inserted towards the cavity retained by the cavity-retaining segment 231 so that it can act as a guide for the passage of other tools (see FIG. 52).

During this operation, the endoscope 240 is kept inserted into the soft sheet member 233 and under endoscopic monitoring the guide needle 241 is inserted from outside the soft sheet member 233 into the cavity.

Next, the dilator 242 is allowed to slide over the guide needle 241 one after another, and to penetrate through body tissues and the soft sheet member 233, thereby gradually enlarging the perforation made by the needle. Finally, a trocar 246 is allowed to slide over the dilator and to penetrate through the soft sheet member 233 (see FIG. 53).

During this operation, as the soft sheet member 233 has a rubber-like nature, and can stretch, the perforation will be smaller if removed of the trocar. Thus, the tip of the trocar 246 is tightly pressed through elasticity by the soft sheet member 233, and is fixed by the pressure to the sheet member. Through this operation, the trocar 246 inserted from outside the soft sheet member comes to communicate with the cavity retained by the cavity-retaining segment 231. Further, as the trocar 246 is firmly fixed by pressure to the sheath 230 for surgery, leakage of muscles and blood through the interstice between the two will not take place. Thus, the visibility of the cavity will be ensured. Further, as the trocar and the sheath are firmly fixed to each other, the trocar will scarcely be drawn out which will ensure smooth insertion of tools through the trocar.

As shown in FIG. 53, a desired number of trocars 246 may be inserted from desired positions as appropriate, and through these trocars 246 necessary tools can be inserted to the operation site. Because these tools are inserted from different positions, no interference occurs between them, which ensures smooth progress of the operation.

Further, when the endoscope 240 is inserted through an added trocar 246, and necessary tools are inserted through the soft sheet member, it is possible to insert tools which are so characteristically shaped or so characteristically sized for passage through the trocar 246, through the soft sheet member into the operation site (see FIG. 53).

When it is necessary during operation to shift the target up or down from the initially marked position, or to push back tissues entering into the cavity creeping under the sheath, it is possible to take appropriate measures by adjusting the position of the handling member 232 or by pressing downward the handling member.

Although in this embodiment the dilator 242 is used as a guide for entry of the sheath 230 for surgery into the body, the insertion of the sheath 230 for surgery can take place in the same manner as in common surgery: body tissues have been removed from spinous processes and pushed aside, and then the sheath is introduced into the body. Or, as in the ninthe embodiment, the sheath 230 for surgery may be introduced into the body, by sliding over an core needle.

As seen from above, as the tip of the cavity-retaining segment 231 at the tip of the sheath 230 for surgery is shaped so as to fit to the vertebral body, it will automatically give a proper position, and, as the proper position of the sheath can be read out from how much the sheath is advanced in the directon of the depth, it will become easy to guide the sheath to a desired position. Further, although it is difficult, when the operation field is small, to get an overview of the field, which often causes the operator to lose the sight of the site to be treated, with this arrangement, by which the sheath 230 for surgery is stably fixed, without deliberate devices, with respect to the site to be treated, the operator will scarcely lose the sight of the site to be treated in the visual field. Still further, even if the sheath 230 for surgery is inserted from a wrong direction and misses the site to be treated, it is possible to find the site by only seeking for the place which will give the most stable foothold to the sheath 230.

After the sheath 230 for surgery has been placed properly, and securely fixed, the visibility of the work space will be scarcely impaired, because the tip of the cavity-retaining segment 231 is so snugly fitted to the vertebral body that it will never displace during operation.

As the tip of the cavity-retaining segment 231 is so securely fixed against the vertebral body, entry of adjacent body tissues into the internal cavity will scarcely take place and the good visiblity of the field will be maintained, once tissues adherent to the vertebral body have been removed.

Further, as the sheath 230 for surgery incorporates the sheet member 233 made of a soft material, it is possible to insert additional trocars 246 through the member into the internal cavity. This will make it possible for other treatment tools to be inserted into the cavity through those trocars 246 without suffering from interference from adjacent tools.

Still further, as the soft sheet member 233 is made of a rubber-like sheet, additional trocars penetrating it will be fixed to the soft sheet member 233 through elasticity of the sheet. This prevents trocars from being withdrawn by accident from the sheet. Further, this arrangement prevents tissues and blood from entering into the cavity through the gap between the soft sheet member 233 and trocars 246, which will lead to the protection of the visibility of the internal cavity. As the soft sheet member 233 is made of a material sufficiently soft, it does not interfere with the movement of trocars 246 penetrating through it, nor with the handling of those trocars.

Still further, when the ring member 231 is made of a semi-solid material, the member yields to deformation, and hence can securely fit to a vertebral body when pressed against it.

Further, as the soft sheet member 233 is employed as the channel for tool insertion 235, no pressure is wrought upon adjacent tissues from this soft sheet member 233, and hence there will be no damage to those tissues. Further, this channel 235 for tool insertion can allow a singularly shaped tool to pass through, and a number of tools to be inserted at the same time. Even when a number of tools are inserted at the same time, scarcely any interference occurs among the tools, and between the tools and the sheath 230 for surgery, and hence handling of those tools is easy.

Figure 54:
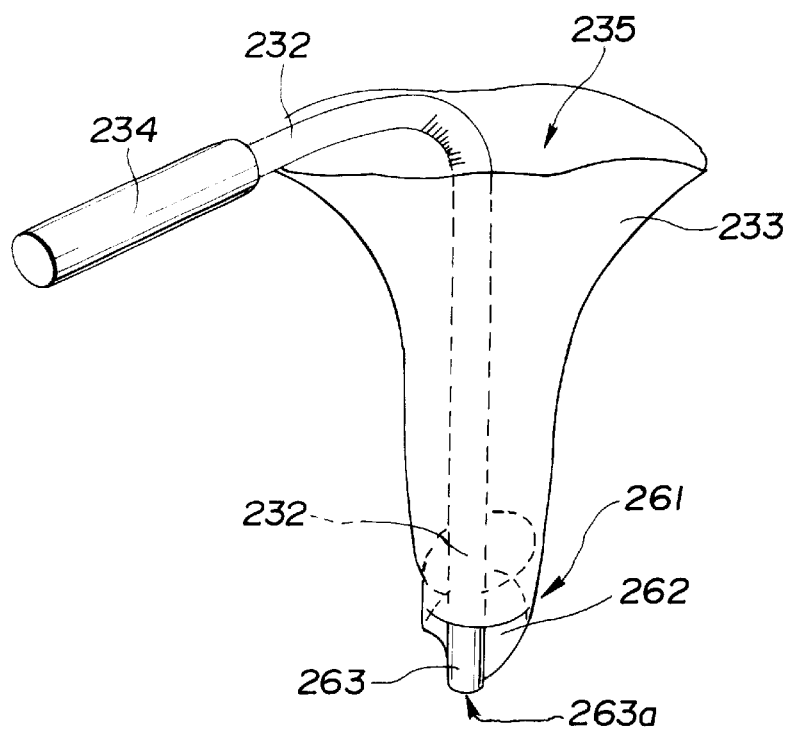
FIG. 54 gives an overview of a sheath for surgery of the fourteenth embodiment of this invention.

The fourteenth embodiment will be described with reference to FIG. 54.

The cavity-retaining means of the sheath 260 for surgery of this embodiment is a cavity-retaining segment 261 whose tip is shaped like a ring. This cavity-retaining segment 261 is constituted with a semi-rigid ring member 262 and a rigid rejecting claw 263 which extends down to the tip of the ring member 262. The tip of the cavity-retaining segment 261 together with the tip of the rejecting claw 263 is so shaped as to fit to the vertebral arch, and is adapted for being fixed to the arch.

The rejecting claw 263 has at its tip a considerably sharp edge 263a. The rejecting claw 263 is connected-to the handling member 232 at the rear end of the ring member 262.

In this embodiment, as in the thirteenth embodiment, the sheath system is guided to a vertebral arch 251, and positioned to a desired point at the posterior end of the arch. The tip of the cavity-retaining segment 261 is principally similarly shaped to that of the thirteenth embodiment, and its operation is similar to the counterpart of the thirteenth embodiment. Thus, it is possible to guide the sheath 260 for surgery to a desired site easily, and, once it has been stabilized against the vertebral body, to prevent adjacent tissues from entering into the internal cavity.

If tissues adherent around the site to be treated are left untouched and remain in the internal cavity after the cavity-retaining segment 261 has been fixed to the arch, they can be stripped off from the bone with the edge 263a of the rejecting claw 263 placed at the tip of the sheath 260 for surgery. During this operation the rejecting claw can be handled through the handling member 232, because the former is directly connected to the latter.

Further, the handling member 232 can be handled to give a pressure sufficiently strong to deform the ring member 262, because the ring member is made of a semi-solid material and can deform more or less under pressure. Thus, handling of the rejecting claw 263 can take place without requiring a considerable displacement of the ring member 262 and thus without increasing the likelihood of tissue invasion from the gap between the ring member and the bone. The subsequent operation is nearly the same as that seen in the thirteenth embodiment.

As the rejecting claw 263 placed at the tip of the cavity-retaining segment 261 can be handled with the handling member 232, it is easy to reject tissues remaining in the internal cavity and interfering with its visibility.

As the ring member 262 of the cavity-retaining member 261 is made of a semi-solid material which can yield to pressure, it is possible to handle the rejecting claw 263 without requiring a considerable displacement of the ring member 262 and thus without increasing the likelihood of tissue invasion. Otherwise, the effects are the same as in the thirteenth embodiment.

The fifteenth embodiment will be described with reference to FIGS. 55 and 56.

Figure 55A:
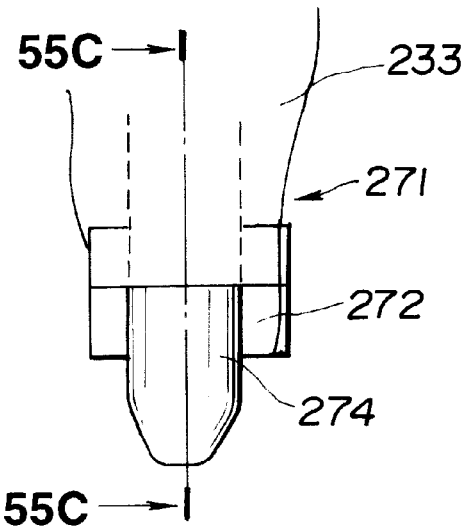
FIG. 55A gives a front view of the tip of a cavity-retaining segment.
Figure 55C:
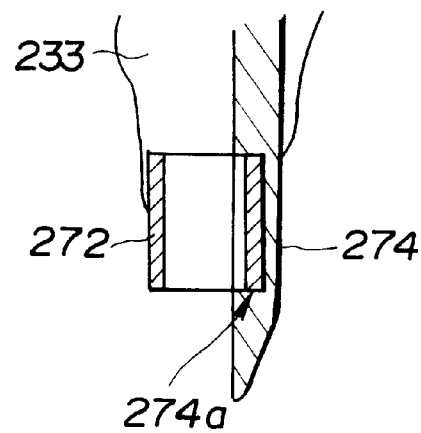
FIG. 55C gives a sectional view along the line 55C—55C in FIG. 55A.
Figure 55B:
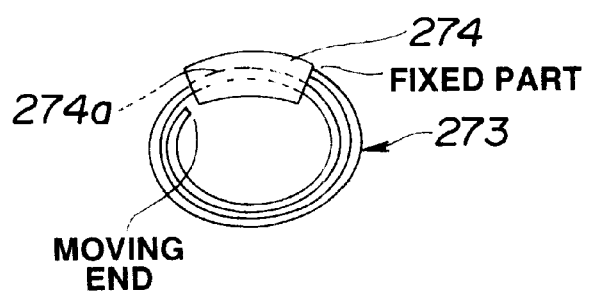
FIG. 55B gives a flat end view of the tip of a cavity-retaining segment.

The cavity-retaining segment 271 acting as a cavity-retaining means in the sheath system 270 of this embodiment is produced, as shown in FIGS. 55A and 55B, after a strip member 272 has been wound into a pipe-like member. In short, this results in a pipe segment 273 whose internal diameter can be varied as appropriate.

As shown in FIG. 55B, one end of the strip member 272 is fixed to the wall of the rejecting member 274. Further, as shown in FIGS. 55B and 55C, the rejecting member has grooves 274a on its wall which provide a channel for the other movable end of the strip member 272 to slide through. The grooves 274a are so shaped as to firmly capture the strip member 272 within their space. The rejecting member 274 has at its tip a tapered edge 274b. The rejecting member 274 and the pipe segment 273 have their tips so shaped, when their external shapes are combined, as to firmly grasp the bone. The cavity-retaining segment 271 is symmetrically constructed with the line 55c—55c in FIG. 55A as a central axis, and hence when this is positioned with its central axis corresponding with a spinous process, its left and right segments will snugly fit to the left and right vertebral arches sandwiching the process.

The use of this sheath 270 for surgery is the same as that in the fourteenth embodiment, and the rejecting member 274 protruding from the pipe segment 273 will penetrate deep down to a site between vertebral arches, to be stabilized there.

Figure 56:
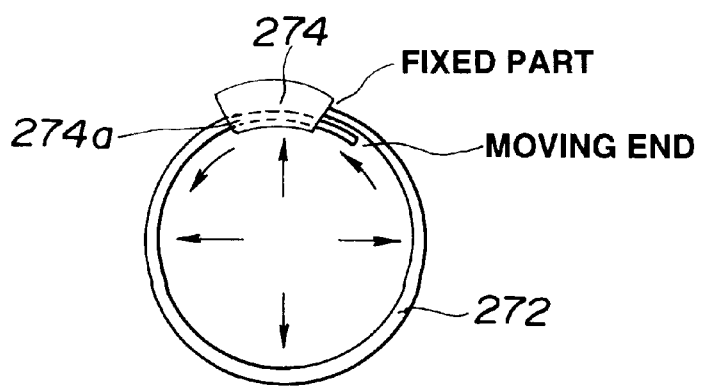

When the visual field is small, and the work space is narrow, the strip member 272 wound in a cylindrical shape is allowed to loosen and to enlarge outward as shown in FIG. 56, thereby to widen the internal cavity. For this purpose, a tool such as a forceps inserted in the cavity may be used to move the movable end of the strip member 272 to loosen the wound ring, so that the internal cavity is widened. Or, the internal cavity may be widened by pushing the movable end of the strip member 272 directly towards the direction to which it is desired to bring about a widening. The strip member 272 is firmly captured by the grooves 274 of the rejecting member 274 and is given a tension. Therefore, the widened cavity can be maintained by the tension developed in the strip member 272 through interaction with the grooves 274a of the rejecting member 274. As the sheath 270 for surgery has a symmetrical form, it can completely fit to both arches of a vertebra.

As seen from above, as the cavity-retaining segment 271 has a cavity-widening means, it is possible to produce a bigger cavity in the body than the perforation initially made. This allows the initial skin incision to be smaller than that commonly observed for this type of operation.

Further, as the cavity-retaining means 271 is constituted with the strip member 272 whose one end is movable, it is possible to elongate the cavity, for example, along the longitudinal axis if it is desired to ensure a visual field in a longitudinal direction. In short, it is possible to widen the cavity to any desired direction.

Still further, as the sheath 270 for surgery has a symmetrical form in its tip, it is possible to fit the tip of the sheath to both arches of a vertebra with its central axis kept in contact with the spinous process.

The sixteenth embodiment of this invention will be described with reference to FIGS. 57–70.

Figure 57A:
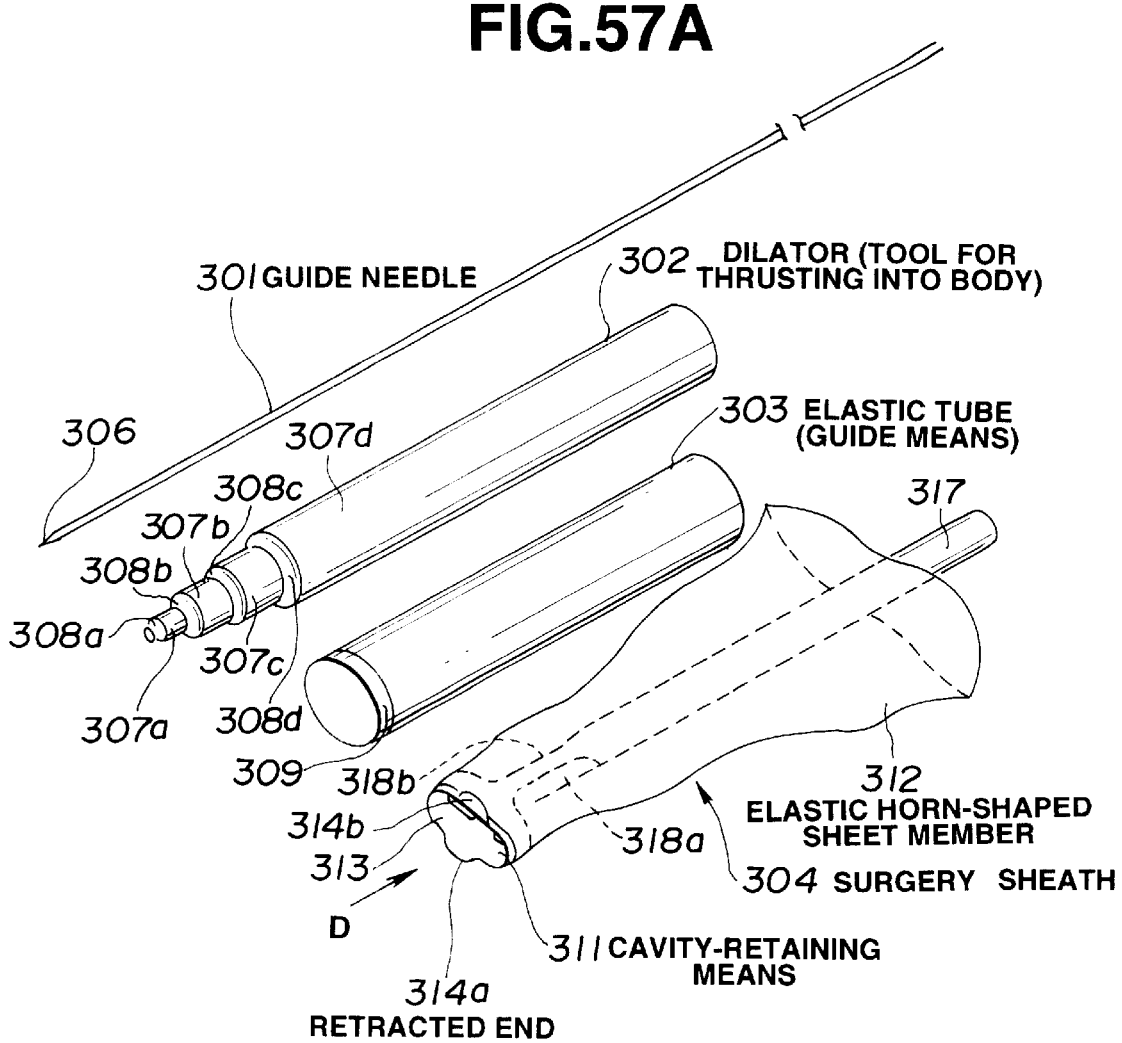
FIG. 57A gives a perspective view of tools constituting a cavity-retaining system for surgery.

FIG. 57A gives tools belonging to a cavity-retaining system for surgery which include a guide needle 301, a dilator 302 or a means by which to drive the system into the body, a soft pipe 303 or a means for guide, and a sheath 304 for surgery.

The guide wire 301 is made of a hard material such as stainless steel, is constituted with an X-ray opaque straight wire, and has a penetrating point 306 at its tip.

The dilator consists 302 of a plurality of tubes 307a–307d placed one over another, or has a multi-tube structure like a stretchable antenna: the smallest-bore tube 307a is allowed to slide over the guide needle 301, the next smallest tube 307b is allowed to slide over the smallest tube 307a, the next, next smallest tube 307c is allowed to slide over the next smallest tube 307b, the same sequence is repeated until a situation is produced where, when the whole assembly is inserted into the body and the guide needle 301 reaches a desired position, the largest-bore tube produces a perforation of a desired size. The smallest or innermost tube 307a has its inner diameter so adjusted as to slide narrowly but smoothly over the guide needle 301. Similarly, the tube 307b is allowed to slide narrowly but smoothly over the tube 307a.

Similarly, the tube 307d is allowed to slide narrowly but smoothly over the tube 307b. Similarly the tube 307c is allowed to slide narrowly but smoothly over the tube 307d. The tubes 307a–307d constituting the dilator 302 have their front edges rounded off to form conical front surfaces 308a–308d.

The soft pipe 303 acts as a guide means when the sheath for surgery 304 is inserted in the body, is constituted, for example, with a tube made of a resin, and is therefore sufficiently elastic as to be deformed in accordance with the shape of the sheath 304 for surgery as will be described later. The soft pipe 303 has its internal diameter so adjusted as to slide narrowly but smoothly over the outermost tube 307d of the dilator 302. The soft pipe 303 has on it front edge a conical front surface 309.

Figure 57B:
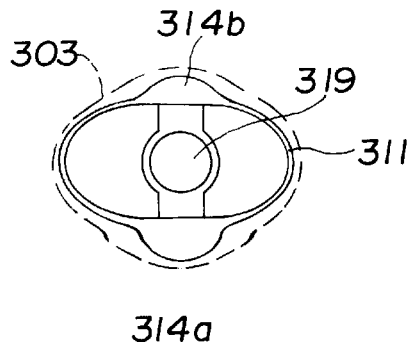
FIG. 57B gives a flat view of a sheath for surgery or a member of the system seen from the direction as indicated by the arrow D in FIG. 57A.
Figure 58:
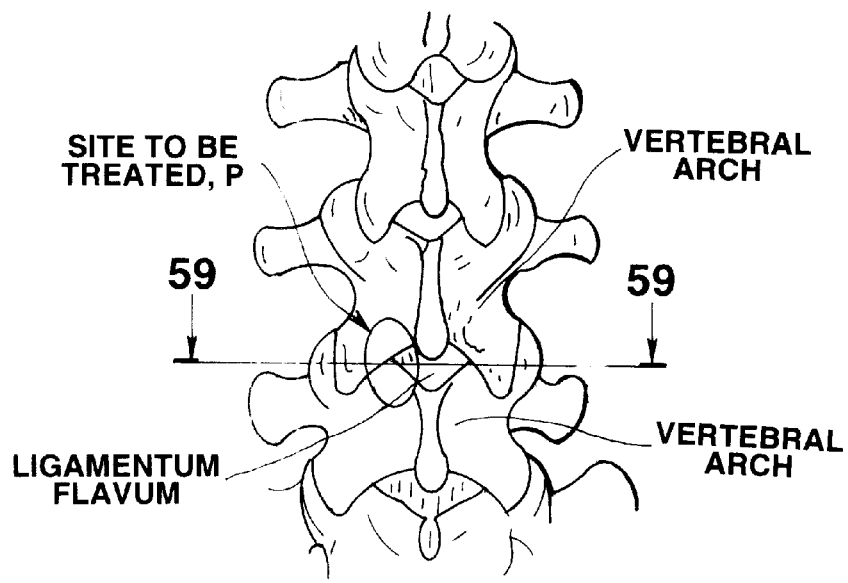

The sheath 304 for surgery is a cavity-retaining tool which comprises a cavity-retaining means 311 which retains a cavity in the body, and a cylinder sheet member 312 which is connected to the cavity-retaining means and acts as a soft tube. The cavity-retaining means 311 is constituted with a ring member 313 whose cavity retaining part consist of a strip wound into a ring. The ring member 313 has an oval form (or ellipsoidal) as shown in FIG. 57B, and contains a space for surgery within its confine. A position retaining means attached to the outer wall of the cavity-retaining segment is constituted with retractions 314a and 314b prepared at the points corresponding with the intersections which the short axis of the ellipsoidal cross-section forms with the periphery of the ring member. These retractions 314a and 314b are hooked against body tissues to further strengthen the fixation of the cavity-retaining means 311 to a desired place in the body, and to prevent adjacent tissues from entering into the internal cavity, thereby ensuring the visibility of the cavity. Generally, the ring member 313 is made of a hard material, but it may be made of an elastic material which can deform under pressure, as long as the material is sufficiently strong to retain the integrity of the cavity.

Although the ring member 313 of the sheath for surgery 304 is singularly shaped, it is so designed that the envelop containing the retractions 314a and 314b has a circumference close to that of the internal wall of the soft pipe 303 (see FIG. 57B). The envelop containing the retractions 314a and 314b of the ring member 313 the sheath 304 for surgery may have a circumference slightly smaller than that of the internal wall of the soft pipe 303. The soft pipe 303 is so designed as to have an internal diameter which is at least smaller than the maximum width of the ring member 313.

The cylinder sheet member 312 is constituted with a soft sheet made of, for example, polyurethane, and is shaped like a tapered funnel. The cylinder sheet member 312 easily collapse, when inserted into the body, under the pressure from surrounding tissues, but treatment tools can be guided through its interior down to the internal cavity retained by the cavity-retaining means 311. The constricted end of the cylinder sheet member 312 snugly fits to the outer wall of the ring member 313, and the remaining part of the cylinder sheet member 312 extends from the fixed joint broadening its width like a skirt. The cylinder sheet member 312 communicates with the internal cavity retained by the ring member 313, and thus acts as a guide for the entry of treatment tools into the cavity retained by the cavity-retaining means 311 during operation, and forms a channel through which treatment tools are conveyed into and carried away from the cavity.

Further, the handling member 317 acting as a handling means is inserted into the cylinder sheet member 312, and the tip of the handling member is connected to the ring member 313 of the cavity-retaining means 311. The handling member 317 is made of a pipe material whose size is considerably smaller than that of the ring member 313, and its end becomes wider in the direction of the short axis of the ring member 313, and comes into contact with both sides of the ring member 313. The handling member 317 has, on its widened tip, two windows 318a and 318b along the long axis of the ring member 313 both of which act as a treatment port. The cylinder sheet member 312 communicates with the internal cavity retained by the ring member 313 of the cavity-retaining means 311 through these windows 318a and 318b. The cylindrical handling member 317 communicates with the internal cavity retained by the cavity-retaining means 311, and form a channel 319 to the cavity. The handling member 317 in the form of a pipe has its internal cavity communicating with the cavity retained by the cavity-retaining means, and hence a continuous channel 319 is formed through the handling member and the cavity-retaining means. The channel 319 through the handling member 311 communicates with the cavity retained by the cavity-retaining means 311 and acts as a means to guide tools inserted into that channel to that cavity. Further, the handling member 317 constitutes a positioning means by which to properly place the cavity-retaining means to a desired position in the body.

Next, the use of this cavity-retaining system for general surgery will be described, with reference to a case where vertebral arches are approached dorsally and a hernia is removed by surgery by the use of this system.

Figure 59:
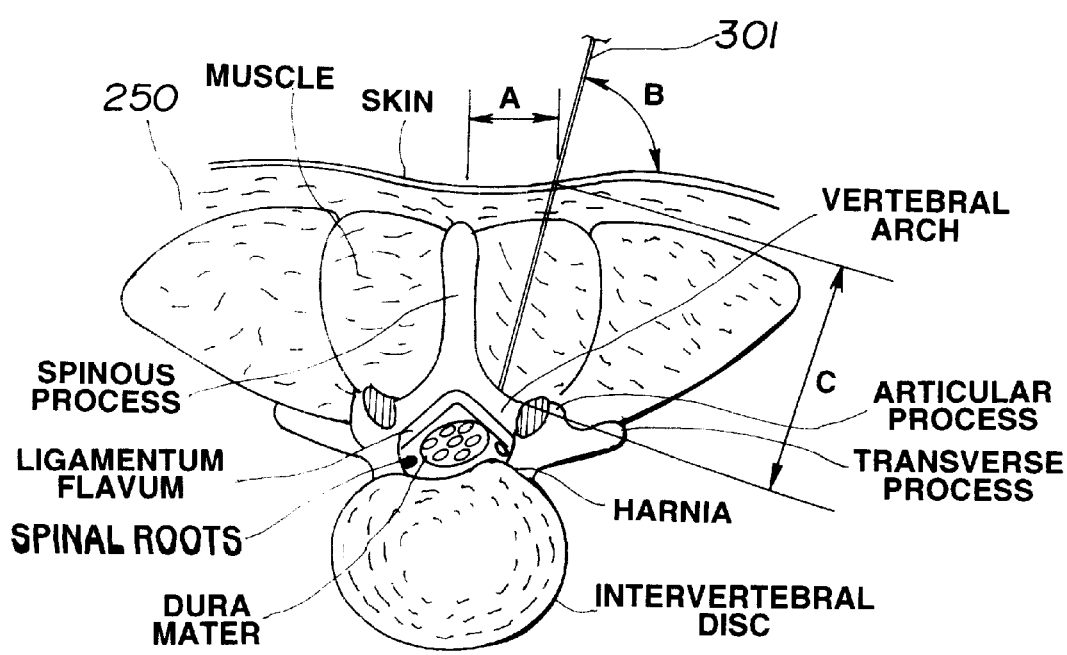

At first, as shown in FIG. 59, the guide needle 301 is inserted through the skin into muscles, aiming at the center of a desired site. The figure illustrates relevant anatomical structures seen from the back of the patient (see FIG. 50). During this operation reference is made to the distance A from the spinous process to the desired site, the insertion angle B, and the depth C down to the vertebral arch in FIG. 59, calculated from the images taken before surgery by X-ray photography or by CT scan. Based on these measurements, positioning is adjusted. After the needle insertion, it is checked by X-ray photography or any other means whether the tip of the needle 301 is properly placed. The needle 301 may be inserted under roentogenographic monitoring.

Figure 60:
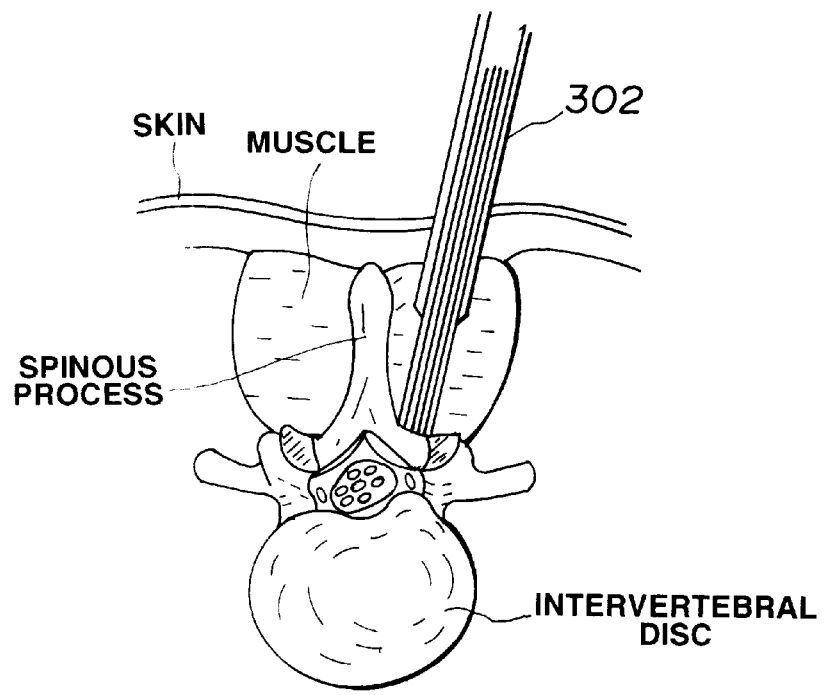
Figure 61:
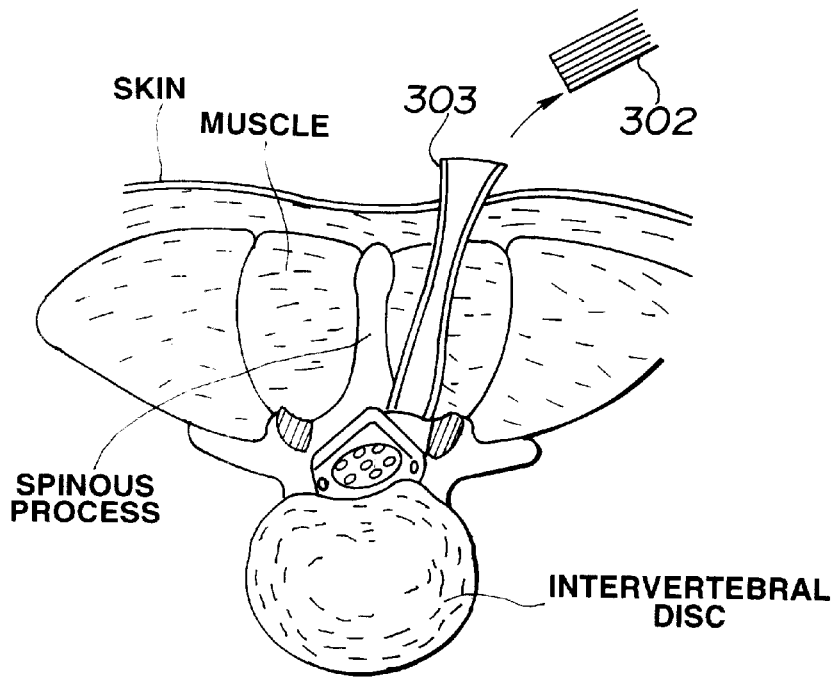

Next, over the guide needle 301, the first tube 307a of the dilator 302 is allowed to slide. The tube 307a is allowed to advance under the guide of the guide needle 301 until its tip reaches the point P. Then, the guide needle 301 is withdrawn. Immediately thereafter, as shown in FIG. 60, the next smallest tube 307b is allowed to slide over the smallest tube 307a, the tube 307c slides over the tube 307b, and the tube 307d slides over the tube 307c until the perforation through muscles becomes as large as the external diameter of the thick tube 307d. At this time, muscles at different layers are stretched in the direction of their muscle fibers, and at the same time split along the fiber directions to elongate themselves. Over the tube 307d or the most thick tube of the dilator 302 is allowed to slide the soft pipe 303, and it is advanced until its tip reaches the point P or the site to be treated. Then, as shown in FIG. 61, only the dilator is withdrawn. Here the soft pipe 303 alone is left in muscles.

Figure 62:
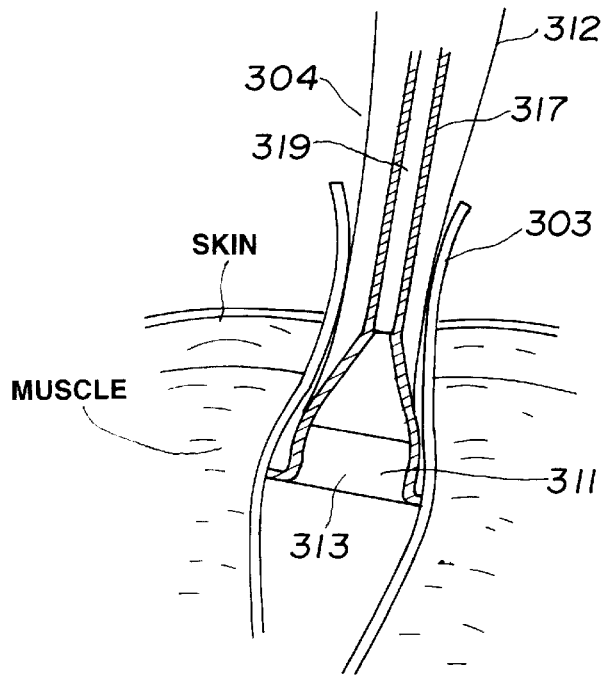

Then, the sheath 304 for surgery is inserted into the internal cavity of the soft pipe 303, using the pipe as a guide as shown in FIG. 62. When the soft pipe 303 is left in muscles, it collapse somewhat under the pressure from surrounding tissues because of its elastic property. However, as the soft pipe 303 is soft and elastic, it is possible to insert the sheath 304 for surgery through the internal cavity of the pipe. Or, as shown in FIG. 61, if the soft pipe 303 is allowed to made of a somewhat tough material, it will more or less maintain the internal diameter even under the pressure from surrounding tissues, which will facilitate the passage of the sheath 304 for surgery.

When the sheath 304 for surgery is pushed into the internal cavity of the soft pipe 303, as shown in FIG. 49B, the ring member 313 of the sheath 304 for surgery which acts as a cavity-retaining means 311 will not undergo deformation. However, the soft pipe 303 will undergo deformation in conformity with the singular shape of the external wall of the ring member 313 including the retractions 314a and 314b. Therefore, the ring member 313 including the retractions 314a and 314b can be introduced into the soft pipe 303 with the interstice being kept intimately closed. Further, as the soft cylindrical sheath is constituted with a cylindrical sheet member and can be folded into a small mass, it does not interfere with the smooth entry of the sheath 304 into the soft pipe 303.

Figure 63A:
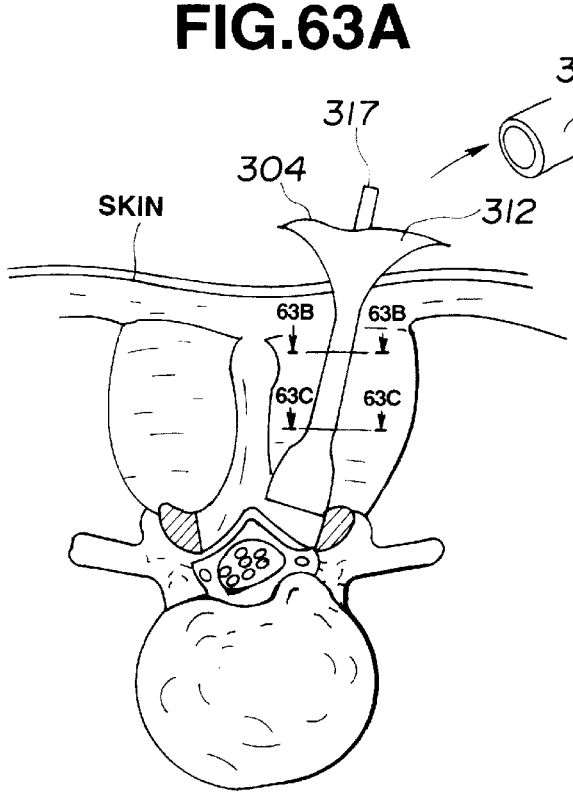
FIG. 63A is an anatomical illustration showing how the sheath for surgery of the cavity-retaining system for surgery reaches the site to be treated and is left there.
Figure 63B:
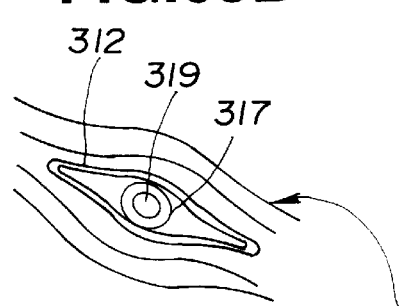
FIG. 63B is an anatomical illustration showing the cross-section along the line 63B—63B in FIG. 63A.
Figure 63C:
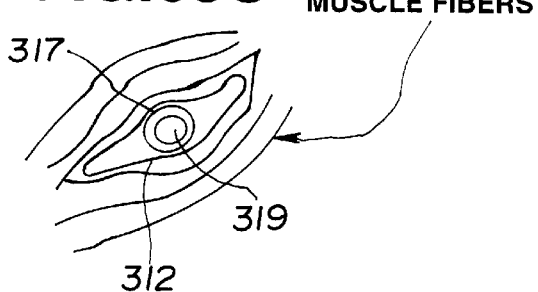
FIG. 63C is an anatomical illustration showing the cross-section along the line 63C—63C in FIG. 63A.

Next, after the ring member 313 of the sheath 304 for surgery has been placed properly on the point P or the site to be treated, the soft pipe 303 is withdrawn. At this stage, as shown in FIG. 63, the soft sheet member 312 takes a flat form along the direction of muscle fibers at different layers under the pressure from those muscles while passing through interstices which are formed after the muscles have been split. For example, as shown in FIG. 63(A), when the sheet member is placed in a point along the line 63B—63B, it undergoes a deformation as represented in FIG. 63B, while when the same member is placed in a point along the line 63C—63C, it undergoes a deformation as represented in FIG. 63C. As the retractions 314a and 314b act as a stopper against muscles surrounding the point P or the site to be treated, they help the ring member 313 of the cavity-retaining means 311 to be securely fixed with respect to the point P. Moreover, they prevent surrounding tissues from entering into the cavity retained by the ring member 313, thereby ensuring the good visibility of the cavity. The widened base end of the soft sheet member 312 extends towards outside.

As seen from above, as the sheath 304 for surgery is stabilized in muscles, the cavity-retaining means 311 can maintain a cavity on the point P or the site to be treated, and this cavity serves as a work place for surgery. The soft sheet member 312 forms a channel through which treatment tools are put into and taken away from the cavity. The channel 319 of the handling member 317 also forms a channel through which treatment tools are introduced into the cavity. Thus, they share the same role as a channel for tools. In agreement with their function, they have their front ends so constricted that their ends can pass through the ring member 3 so smoothly that they do not impose a strong pressure on surrounding muscles.

Figure 64A:
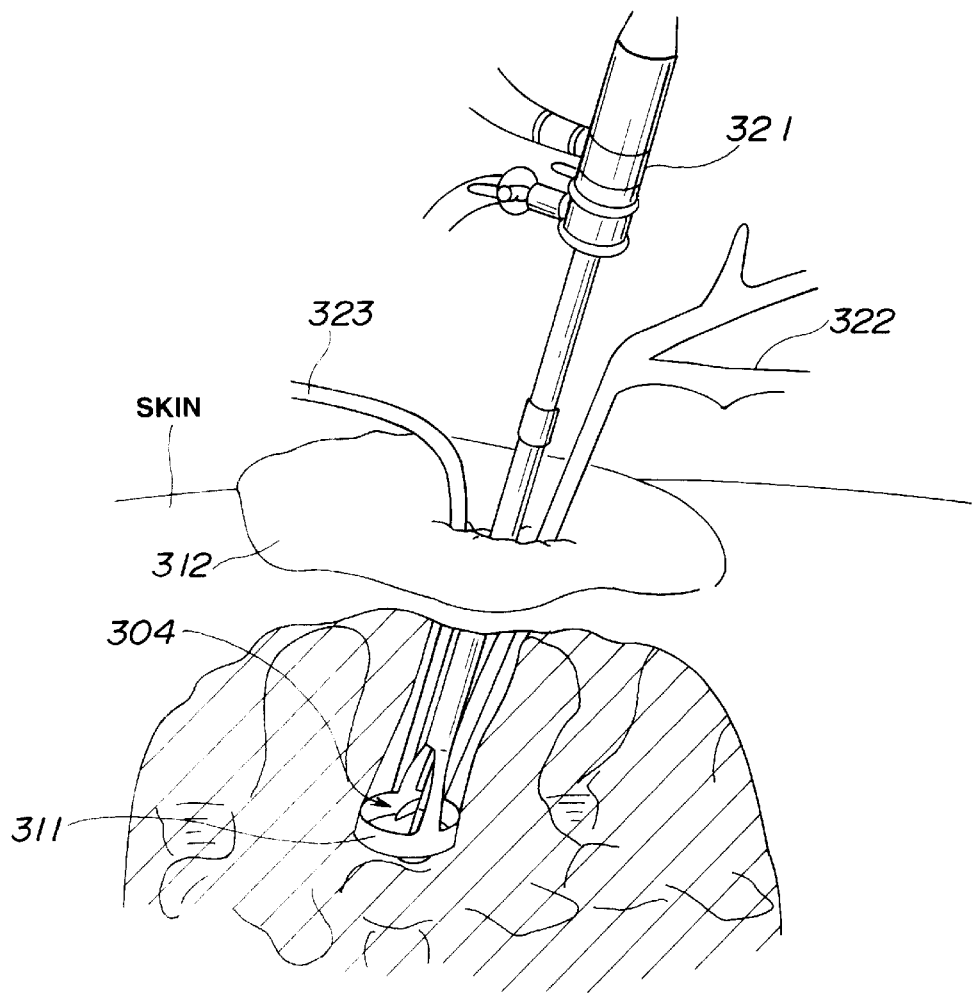
FIG. 64A illustrates how surgery is practiced using the cavity-retaining system for surgery.
Figure 64B:
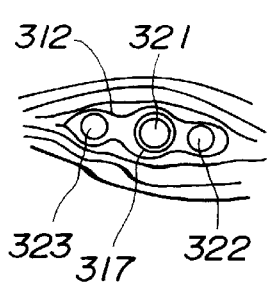
FIG. 64B is an anatomical illustration showing the cross-section of the mid-section of sheath for surgery.
Figure 64C:
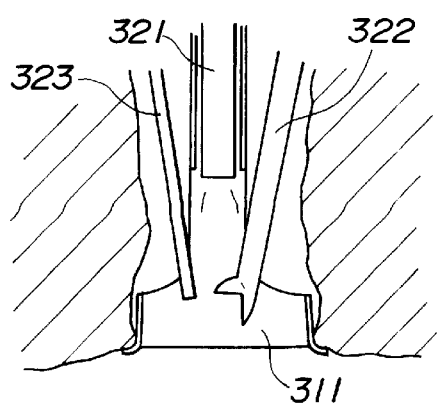
FIG. 64C illustrates how operation proceeds in the cavity.

As shown in FIG. 64A, various tools are inserted through the soft sheet member 312 and reach the work space retained by the cavity-retaining means 311. In this example, a scope 321 with an irrigating device is inserted into the channel 319 of the handling member 317, a curette 322 is inserted from a part of the outward periphery of the soft sheet member 312 which has collapsed flat, and a suction pipe 32 is inserted from another part of the same outward periphery. In this state, as shown in FIG. 64B, those tools are arranged in a row. Further, the tools inserted from opposite ends of the soft sheet member 312 are allowed to reach, through the windows 318 for treatment, the work space as shown in FIG. 64C. Because the soft sheet member 312 does not interfere with the movement of tools inserted therein, it is easy to insert a tool obliquely through the space within the soft sheet member as shown in FIG. 64C. Thus, it allows a high degree of freedom and handiness of tools which are inserted into it. Furthermore, because the sheet member is made of a soft sheath material, it is possible to insert a plurality of tools in one part of its outward periphery. This allows complicated works to be executed efficiently. If blood accumulates in the work space, it is possible to remove it with the suction tube 23.

If a different angle is desired for approach, or if a slightly different field of view is desired, the handle member is used to displace the system with respect to the cavity until the desired angle or field of view is obtained, and then the system is stabilized there. Further, as the scope 321 is equipped with an irrigating device, it may be possible to perform the surgery while circulating saline through the wound. This is advantageous in that it does not allow splashes of blood and hence protects the scope against soils from blood.

Figure 65:
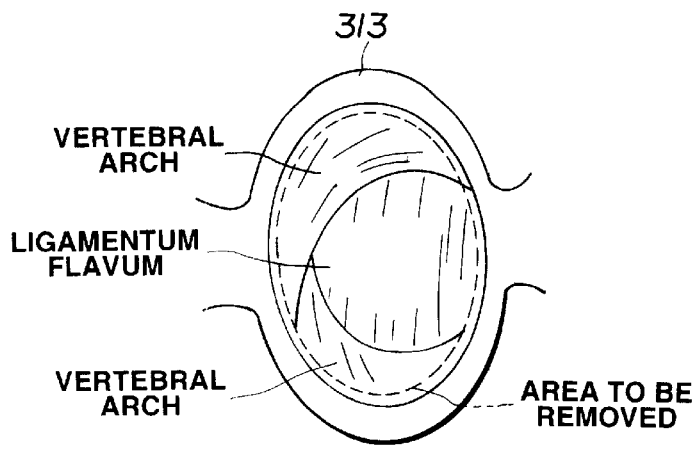

FIG. 65 shows a filed of vision which is conveyed by the scope 321 directed towards the work space retained by the cavity-retaining means 311, and which is focused upon P or the site to be treated. The area delineated by the dotted line indicates what is to be removed.

Steps for resection of affected parts will be described by means of an example.

Figure 66:
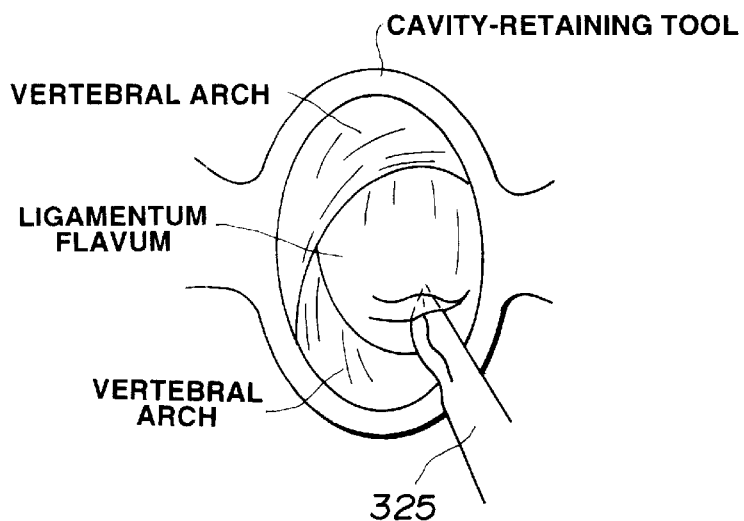
Figure 67:
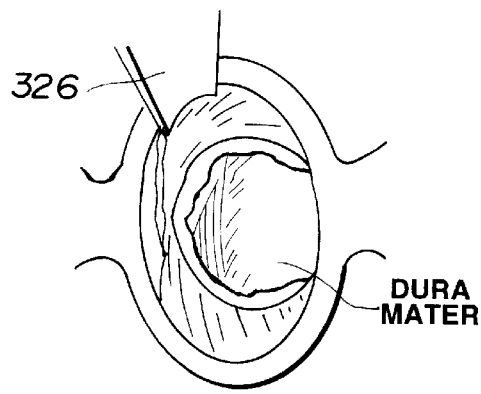

Firstly, as shown in FIG. 66, a scalpel 325 is inserted through the soft sheet member 312 into the cavity, to cut the ligamentum flavum. After the work is completed, the scalpel 325 is withdrawn. Then, as shown in FIG. 67, a drill cutter or a chisel 326 is inserted into the cavity, to scrape away the upper and lower vertebral arches. Then, as shown in FIG. 68, the vertebral arches are further scratched away, thereby to expose underlying dura mater and spinal roots. A nerve probe 328 is inserted and used to push aside dura mater and spinal roots together to one side, as shown in FIGS. 69 and 70. While the dura mater and spinal roots are kept immobilized, a curette 322 is inserted from another part of the soft sheet member to removed the herniated intervertebral disc. The operation may be performed with a plurality of forceps inserted from the same part of the soft sheet member.

After a series of steps necessary for resection of the hernia have been completed, the sheath 304 for surgery is withdrawn from the body, and the wound is sutured to complete the operation.

As this sheath 304 for surgery comprises the cavity-retaining means 311 including the ring member 313, and the soft sheet member 312, as a first merit, it allows the ring member to prepare a work space of the minimum range corresponding precisely with the site to be treated. As a second merit, it inflicts minimal damages to body tissues, because the soft sheet member 312 has scarcely any rejecting activity towards surrounding muscles. As a third merit, it does not exert rejecting activity through the cavity-retaining means 311 neither, because the cavity-retaining means 311 is so singularly shaped as to fit to the site to be treated as closely as possible, thus minimizing the space necessary for operation. Through these features, this system can minimize inflicting damages to dorsal muscles through the rejecting activity, and hence, it can avoid to inflict irreversible major damages to dorsal muscles, dispenses with major incisions, and causes no serious damages in dorsal muscles.

Further, as the soft pipe 303 which acts as a guide when the singularly shaped ring member 313 is inserted into the body, can deform under pressure, the rigid ring member 313 can be inserted into the soft pipe 303, as long as the ring member's circumference is in correspondence with the internal circumference of the soft pipe 303. Accordingly, the internal diameter of the soft pipe 303 requires no further definition as long as it corresponds with the maximum diameter of the ring member 313 of the cavity-retaining means 311. This allows the soft pipe 303 to have a shorter diameter than is possible for a hard pipe, which allows further the soft pipe to pass through a smaller hole and thus to inflict smaller damages to nearby tissues.

Further, as the soft sheet member 312 is constituted with a soft tube which has an edge extending outward like a skirt, it allows a plurality of tools to be inserted obliquely into its interior. Furthermore, as it is made of a soft material, tools inserted in it can have a high degree of freedom and handling of the tools becomes easy. Still further, as the soft sheet member 312 communicates with the internal cavity, and works as a guide for tools to be inserted into the cavity, it is easy for tools to be conveyed into and carried away from the cavity. To the sheath 304 for surgery is mounted the handling member 317 which protrudes its handle towards outside and acts as a positioning means. The handling member 317 can adjust the angle with which tools approach the cavity, and fix and change the position of the cavity.

Further, the handling member 317 is positioned at the center of the cavity, and has a channel 319 at its center. Even if an endoscope 321 is passed through the channel, it is possible to insert tools such as forceps through the ports opened on both sides of the scope 321, and thus the scope scarcely interferes with the movement of tools on its two sides. This improves handling of the tools.

Still further, as the ring member 311 is provided with the retractions 314a and 314b as a position-retaining means, it is possible for those protrusions to be hooked against nearby tissues, which will allow the cavity to stabilize, once it has been fixed to the body. Furthermore, the retractions 314a and 314b prevents unnecessary body tissues from entering into the cavity, thereby ensuring a necessary field of vision and a work space.

The dilator 302 which is to drive the system into the body prepares a channel in the body, and allows the sheath 304 for surgery with a soft sheet to be left in that channel. Namely, the dilator 302 prepares a channel not by cutting muscles but by separating them to make a hole in the midst of them. Into that hole is introduced the soft sheet member 312 which has no notable rejecting activity towards those muscles. This will minimize injuries to the muscles.

The soft sheet member 312 does not necessarily require, as its material, an elastic material which stretches in the presence of a tension, but such material may also be used.

Further, it is possible with this system, if it has no port for tools, to introduce a thin pipe such as a port 64 illustrated in FIG. 85C through a hole prepared outside the sheath towards the cavity, to insert it through the soft sheet into the cavity, and to then pass a tool through the thus obtained channel into the cavity, or to insert a tool directly into the body to penetrate through the soft sheath and to reach the cavity.

The seventeenth embodiment will be described with reference to FIGS. 71–73.

Figure 71:
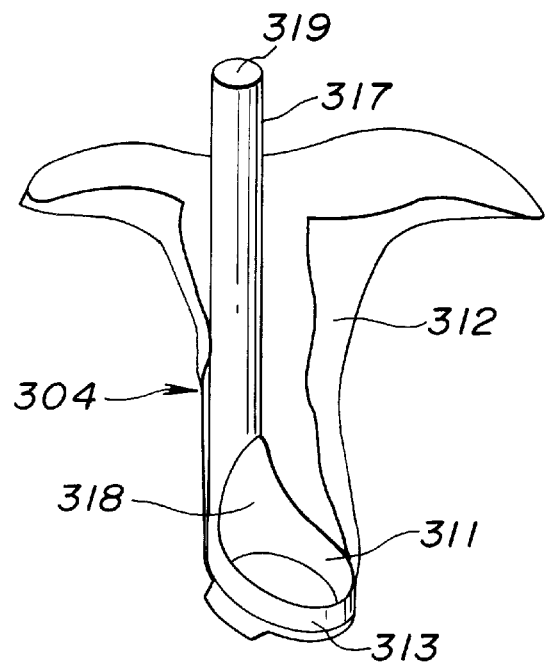
FIGS. 71–73 refer to the seventeenth embodiment of this invention.
Figure 72:
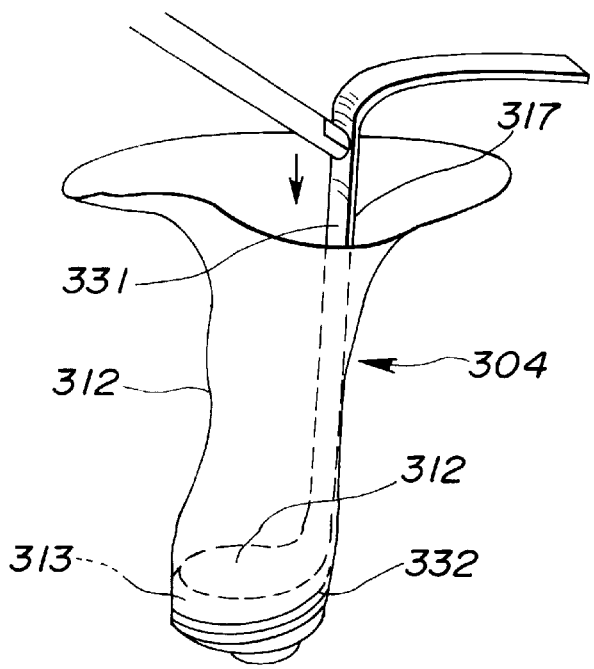
Figure 73:
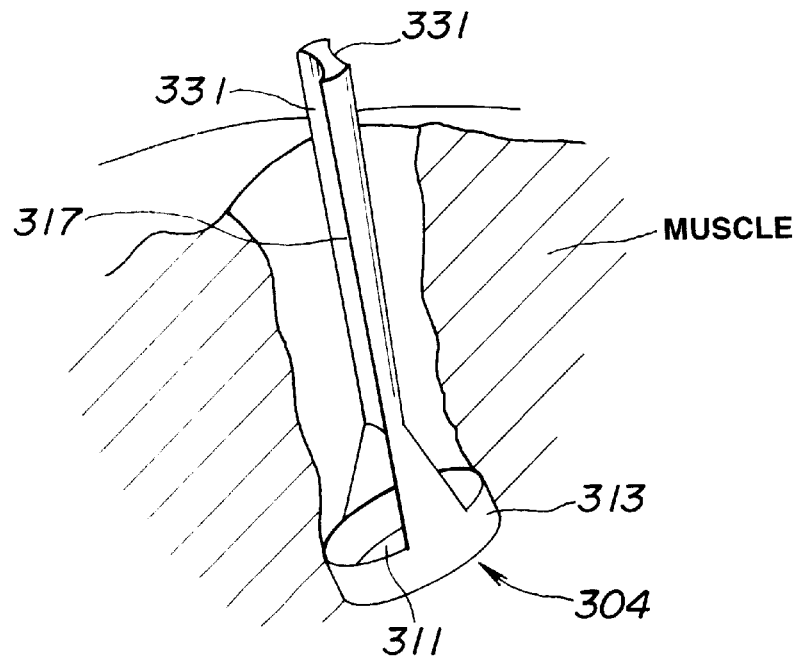

The seventeenth embodiment represents a version of the sixteenth embodiment where the sheath 304 for surgery is modified, and FIGS. 71–73 illustrate how the sheath is modified.

The sheath illustrated in FIG. 71 has the segment of the handling member 317 which is fitted to the ring member 313 of the cavity-retaining means 311 so adjusted in position that the end of the segment shifted towards one side along the long axis of the ellipsoidal cross-section of the ring member 313. The window 318 of the channel 319 for tool insertion forms one of the channels communicating with the cavity. With this system, it is possible, even if a scope 321 is passed through the channel 319, to insert a considerably big tool through the cavity of the soft sheet member 312 without being interfered by the scope, because the channel 319 for tool insertion is shifted to one side.

The handling member 317 illustrated in FIG. 71 has the segment which is fitted to the ring member 313 of the cavity-retaining means 311 made not of a tubular material but of a flat material, and has the same segment, as is seen in the above version, so positioned that the end of the segment is shifted towards one side in the cross-section of the ring member 313. The flat handling member 317 forms, on the side wall of the internal cavity of the cavity-retaining means 311, a concave guide surface 331 to facilitate the passage of tools. The tubular sheet member 312 covers the ring member 313 with its tip and is fastened to the latter by a ligature with a thread 332. The ligature with the thread 332 may be further fixed with a bonding agent. For a tool to be inserted into the sheath 304 for surgery, it is necessary to introduce the tool along the guide surface 331 prepared on the wall of the handling member 317. Through this procedure, introduction of tools into the cavity of the sheath 304 for surgery can be easily and securely made.

The handling member 317 illustrated in FIG. 73 has the segment which is fitted to the ring member 313 of the cavity-retaining means 311 made not of a tubular material but of a flat material, and has the same segment so positioned that the end of the segment falls at the center of the cross-section of the ring member 313. The flat handling member 317 has, on the front and back walls, concave surfaces which act as a guide surface 331 for tools. The sheath 304 for surgery of this version has no tubular sheet member 312 as in the foregoing version, because the handling member 317 acts as a guide means for tools. Needless to say, however, the sheath can have such a tubular sheet member 312.

As the handling member 317 is prepared smaller in this version than the cavity-retaining member, similarly to the foregoing version, it is possible to insert tools easily along the guide surface 331 into the cavity without imposing a strong rejecting pressure to nearby muscles.

Figure 74:
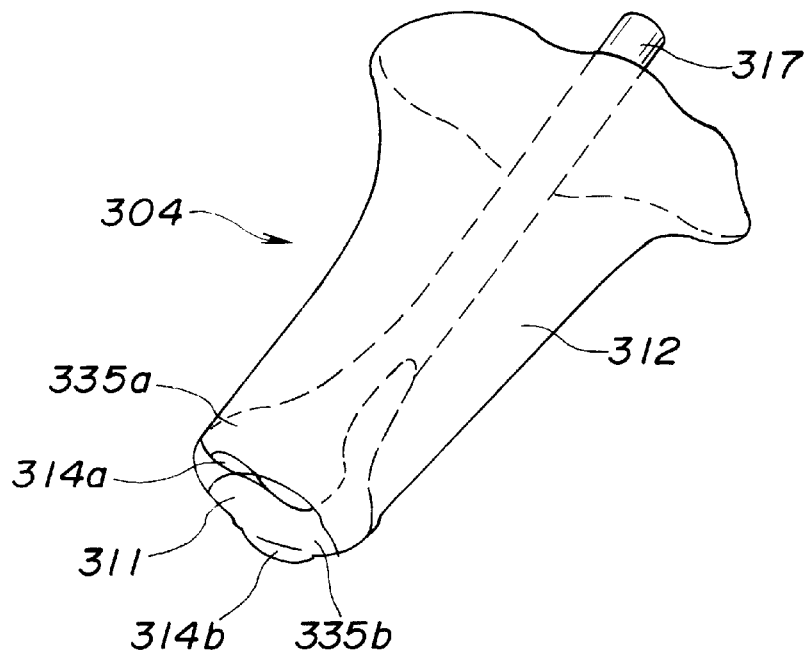
FIG. 74 gives a perspective view of a sheath for surgery.

The eighteenth embodiment will be described with reference to FIGS. 74–76.

The eighteenth embodiment represents a version of the sixteenth embodiment where the cavity-retaining means 311 of the sheath 304 for surgery is modified, and otherwise similar to the sixteenth embodiment.

The retaining means 311 of this embodiment is continuous with the tip of the handling member 317 and consists of a pair of lobes 335a and 335b which face to each other, to form a cavity-retaining means. The pair of lobes 335a and 335b are bonded closely together to the end of the internal surface of the cylinder sheet member 312. The pair of lobes 335a and 335b have, on their end, retractions 314a and 314b. The pair of lobes 335a and 335b are made of such an elastic material that they can expand at least as wide as does the ring member 313 described above.

This sheath 304 for surgery is used similarly to that described in relation to the sixteenth embodiment, and, when it is inserted into the interior of the soft pipe 303 which acts as a guide, the pair of lobes 335a and 335b is closed intimately as shown in FIGS. 75A and 75B. They are allowed to advance until they reach a position close to the site to be treated, and at this stage the soft pipe 303 acting as a guide is withdrawn. Then, as shown in FIG. 76, the pair of lobes 335a and 335b depart from each other owing to their intrinsic elasticity, to push aside through the elasticity adjacent body tissues to ensure a cavity within the tissues. In this version, the pair of lobes at the same time work as a cavity-retaining means and a cavity-expanding means.

As this sheath for surgery 304 allows the pair of lobes 335a and 335b which act as a cavity-retaining means to be inserted as an intimately closed mass, it is possible to further contract the internal diameter of the soft pipe 303 for guide, which will permit the system to be less invasive to adjacent body tissues. Further, when this system is applied for bone surgery, the pair of lobes widens themselves to form a cavity, and thus can neatly push aside muscles or the like adherent to the surface of the bone. Furthermore, as the pair of lobes expand the cavity by elasticity, and dispenses with an expanding means specially made for the purpose, they will make it possible to contract the size of the sheath. Accordingly, with this system, interference between tools can be reduced which will permit the system to cause less damages to the body.

The nineteenth embodiment will be described with reference to FIGS. 77–80.

This nineteenth embodiment is a version of the above-described sheath 304 for surgery in which the guide means is modified.

The guide means 340 which guides the insertion of the sheath 304 for surgery in this embodiment is constituted, as shown in FIG. 77, with a pair of flat guide members 341a and 341b facing to each other, and the flat guide members 341a and 341b have, on their internal surfaces facing to each other, guide surfaces 342a and 342b formed. The guide surfaces 342a and 342b are so prepared that they form an arch in cross-section, the envelop containing their periphery is circular in form, and thus the guide surfaces 342a and 342b together forms a cylinder circular in cross-section.

The guide members 341a and 341b are continuously jointed to a rectangular, hollow base 343, and are so constructed that they become narrowed towards the tip spontaneously through their intrinsic elasticity, or through the elasticity given by the base, as is shown in FIG. 77.

When this guide means 340 is used, as shown in FIG. 78, the guide members 341a and 341b are allowed to widen sufficiently to be slid over the last tube 307d of the dilator 302, and then they are pushed in until they reach a desired point in the body. Thereafter, the dilator 302 is withdrawn. Then, as shown in FIG. 79, the guide members 341a and 341b become intimately closed under the pressure from adjacent tissues. Later, as shown in FIG. 80, a sheath 304 for surgery like the one described above is inserted between the guide members 341a and 341b, and pushed in along the guide surfaces 342a and 342b. Then, the guide members 341a and 341b widen as much as the size of the sheath 304 for surgery, and, pushing aside body tissues, guide the sheath 304 for surgery as far as the site to be treated. Later, the guide members 341a and 341b are withdrawn leaving the sheath 304 for surgery behind, which is ready for the same operation as described above.

When the guide means 340 of this embodiment is used, the pair of guide members 341a and 341b kept closed widen to form a cavity, and thus can neatly push aside muscles or the like adherent to the surface of the bone. Then, they are withdrawn to leave the sheath 304 for surgery behind, and hence the sheath 304 for surgery can command a good field of view.

The twentieth embodiment of this invention will be described with reference to FIGS. 81 and 82.

This twentieth embodiment represents a version of the sixteenth embodiment where the sheath 304 for surgery is modified.

The sheath 304 for surgery of this embodiment has the handling member 317 which is, being made of a tubular member, so constructed as to have, as a cavity-retaining means 311, a pair of sticks 345a and 345b facing to each other at its tip. The pair of sticks 345a and 345b for retaining a cavity, as shown in FIG. 81B,. has a width larger than the diameter of the handling member 317. The sticks 345a and 345b have at their tips retractions 346a and 346b directing towards reverse directions. The sticks 345a and 345b are made of a material which can undergo plastic deformation. The sticks 345a and 345b have their tips hooked against the internal surface of the cylinder sheet member 312.

When the sheath 304 for surgery of this embodiment is used, similarly to that in the sixteenth embodiment described above, it is introduced through the soft pipe 303 left in the body to a desired place in the body. After the sticks 345a and 345b for cavity retention has been protruded from the tip of the sheath 304 for surgery, as shown in FIG. 82, a cavity-expanding tool is inserted through the channel 19 of the sheath 304 for surgery, to widen the sticks 345a and 345b for cavity retention. The widened sticks 345a and 345b expand body tissues, undergoes plastic deformation and forms a work space within its legs.

The cavity expanding tool 347 consists of a pair of handling sticks 349a and 349b which can widen bilaterally, and has the sticks attached to the tip of the insert 48. This tool is operated by hand to open the pair of handling sticks 349a and 349b, thereby pushing apart the cavity-retaining sticks 345a and 345b.

This embodiment allows the dimension of the cavity to be adjusted as appropriate, which is achieved after the cavity-retaining sticks 345a and 345b have been widened by a necessary width.

Furthermore, as the preservation of the expanded cavity takes place as a result of the plastic deformation of the cavity-retaining member 345a and 345b, reducing the size of the sheath will become possible. Accordingly, with this system, interference between tools can be reduced which will permit the system to cause less damages to the body.

The twenty-first embodiment of this invention will be described with reference to FIGS. 83 and 84.

This twenty-first embodiment is a version of the sixteenth embodiment where a penetrating tool is used instead of the dilator 302.

The penetrating tool 350 is constituted, as shown in FIG. 83A, with a cylindrical insertion body 351 which acts as a scope channel, and has, on its tip, a transparent window member 352 whose external surface is semicircular in form. A scope which is not illustrated here and is inserted into the scope channel can watch the field in front through this window member 352. On the external surface of the window member 352 is mounted a conductor 353 comprising an electroconductive wire which acts as an electric scalpel. Through conductor 353 a radio frequency current which is provided by a radio-frequency generator 355 is allowed to pass by way of a power cord 354 which leaves the basic end of the insert body 351. Close to the basic end of the insert body 351 is placed a hand-switch 356 which acts as a controller of the passage of electricity. The switch 357 can be reversibly attached to the insert body 351. A foot-switch may be used as a controller of the passage of electricity.

To the front end of the insert body 351 is prepared a fitting member for surgery sheath 358 which is slightly smaller in diameter than the rest. This fitting member 358 for surgery sheath is so constructed as to be fixed to the sheath 304 for surgery when the insert body 351 is inserted into the ring member 313 of the sheath 304 for surgery which has, as shown in FIG. 71, the handling member 318 eccentrically positioned.

Next, a case will be described where the sheath 304 for surgery is introduced to a site to be treated by the use of the penetrating tool 350.

Firstly, as shown in FIG. 83B, the ring member 313 is fitted to the fitting member 358 of the penetrating tool 350, to fix the sheath 304 for surgery with respect to the penetrating tool 350. Then, the penetrating tool 350 is pushed in to allow the window member 352 exposed at the tip of the penetrating tool to advance into muscles. At this stage, at first, an electric current is passed through the conductor 353, to allow the tip to advance into the muscles. Once the tip has been inserted into the muscles, the muscles are split in the direction of fibers through pressure by the passage of the transparent window member 352 whose external surface is semi-circular, and thus the penetrating tool 350 can smoothly pass through an interstice between separated muscles. However, if the tip of the penetrating tool 350 reaches a different tissue layer, and hits against something hard such as fascia or the like and can not advance further simply by pressure, the conductor 353 is adjusted in position to be in parallel with the direction of adjacent muscle fibers while the direction of muscle fibers is monitored with a scope, and an electric current is allowed to pass through the conductor 353, to cut the fascia to open a perforation. Then, the muscle fibers are split anew to allow the passage of the penetrating needle 350. Through repetition of the same procedure each time the penetrating tool 350 reaches a different layer, the penetrating tool is allowed to attain a desired depth. This procedure allows the penetrating tool to reach a desired depth without cutting muscle tissues, and thus inflict less damages to muscles. If bleeding takes place during the insertion of the penetrating tool, a radio-wave current is allowed to pass through the conductor 353 to coagulate the bleeding vessel. This diathermy treatment can also be applied for the resection of ligamentous tissues adherent to the surface of a bone. Once it has been confirmed that the sheath 304 for surgery reaches the site to be treated, the penetrating tool 350 is withdrawn.

FIG. 84A shows the sheath 304 for surgery is properly placed with respect to the site to be treated through the procedure described above, and at this state the sheath 304 for surgery maintains a cavity or a work space with the ring member 313 opposite to the site to be treated. The cylinder sheet member 312 contacts, from tip to base, with various muscle layers, and is flattened by the pressure from surrounding muscles layers in the directions corresponding with the fibers of those muscles. Thus, it undergoes deformation as shown in FIG. 84B at a level corresponding with the line 84B—84B, and deformation as shown in FIG. 84C at another level corresponding with the line 84C—84C. This suggests that muscle fibers are not cut around the passage of the sheath. In addition, as the part of the sheath that comes in direct contact with muscles is a soft sheet, damages to the muscles can be minimized. Further, this system dispenses with the operation involved in the repeated sliding of tubes required when the dilator 302 is used as in the sixteenth embodiment.

As an alternative, the following may be employed: this penetration tool alone, instead of in combination with the cylinder sheet member, is introduced into the body, the insert body 351 acts in place of the dilator 302, the pipe 303 is slid over the insert body, and the assembly is further introduced into the body.

The twenty-second embodiment will be described with reference to FIGS. 85–88.

FIG. 85 presents tools belonging to a cavity-retaining system for general surgery according to the twenty-second embodiment. FIG. 85A represents a sheath 361 for surgery, FIG. 85B a cavity expander 362, FIG. 85C a core needle 363 and a port 364, and FIG. 85D a port guide 365.

The sheath 361 for surgery comprises a pipe member 366 which has the same diameter throughout its length. The pipe member 366 has its tip split into two, and the resulting halves face each other to form a pair of sticks 367a and 367b for cavity retention. Thus, the sticks 367a and 367b together form a cavity-retaining means 368. The pair of sticks 367a and 367b, as shown in FIG. 85, can be kept opened after their base ends are allowed to undergo plastic deformation. The internal cavity of the pipe member 366 acts as a channel for the insertion of a scope 369 or the like. At the basic end of the pipe member 366 is placed a tenon 371 which forms a step and is to fit to a member of a port guide 365.

The cavity expander 362 can be inserted into the channel of the cavity-retaining means 368 and has a pair of handling sticks 372a and 372b which can open bilaterally. The pair of handling sticks 372a and 372b can widen bilaterally, and operated by hand to widen, thereby pushing apart the cavity-retaining sticks 367a and 367b. The number of the cavity-retaining sticks is not limited to that in this embodiment.

The core needle 363 is snugly inserted into the channel of the cavity-retaining means 368, and is allowed to protrude its tip from the closed end of the cavity-retaining means 368. This core needle can also be inserted into the port 364 which is formed as a pipe.

The port guide 365 comprises a pair of grasping members 375a and 375b and has those grasping members movably hinged at one end. On the internal surface of the grasping members 375a and 375b are prepared grooves corresponding with a central reference hole 376, and a first guide hole 376 and a second guide hole 376c being positioned on both sides of the central hole. The reference guide hole 376a, the first guide hole 376b and the second guide hole 376c which are formed when the pair of grasping members are closed, are used for the insertion of the sheath 361 for surgery or the introduction of the port 364. The reference guide hole 376a is placed normal to the port guide 365, and the first and second guide holes 376b and 376c are so inclined with respect to the reference guide hole 376 that the extensions of their long axes intersect at one point with that from the long axis of the reference guide hole 376a. The extensions connecting that point with the respective holes are so directed as to pass through the interior of the cavity-retaining means 368.

Next, the cavity retaining system for surgery according to this embodiment will be described.

Firstly, for the sheath 361 for surgery to be inserted into the body, the core needle 363 is passed through the sheath, and allowed to protrude its tip or the penetrating segment 373 from the front end of the cavity-retaining means 368, and to penetrate through body tissues like muscles. Once the cavity-retaining member 368 has reached the site to be treated, the core needle is. withdrawn and instead the cavity expander 362 is inserted. By manipulation, the pair of handling sticks 372a and 372b constituting the cavity expander 362 is opened bilaterally, and push apart, as shown in FIG. 86, the cavity-retaining sticks 367a and 367b, thereby to preserve a cavity to act as a work space.

Then, over the tenon 371 of the sheath 361 for surgery is slid the reference guide hole 376 of the port guide 365, and the port guide 365 is thereby properly positioned with respect to the sheath 361 for surgery. At this stage, the extension connecting the centers of the first and second guide holes 376b and 376c, when projected to the cavity formed by the pair of cavity-retaining sticks 367a and 367b, passes through its center.

Next, description will be given of how to place ports 364 through the first and second guide holes 376b and 376c of the port guide 365 while the above condition is maintained. As shown in the left side of FIG. 87, a port 364 having a core needle 363 within its interior is inserted through the first guide hole 376b into the body. Then, as shown in the right side of the same figure, the port passes through the cavity formed by the sheath 361 for surgery. As seen from this, all the extensions of the central axes from the reference, first and second guide holes of the port guide 365 pass through the cavity formed by the sheath 361 for surgery. Later, guide members including the core needle are withdrawn, and necessary tools are passed through the ports 364 to make surgery.

As seen from above, as shown in FIG. 88, different treatment tools including a scope 369, a curette 377 and other tools 378 can be separately introduced into the same cavity retained by the sheath 361 for surgery.

Further, as tools are independently inserted through different holes, individual holes can be made small. Therefore, damages involved in the preparation of those holes will become minor and necessary rejecting operation will be less. Furthermore, as tools are inserted from holes apart from each other, interference between tools will be reduced, and thereby handling of tools will be improved.

The sheath 361 for surgery of this embodiment allows a treatment cavity in the body to be relatively large in spite of the insertion hole being small. Thus, invasion necessary for the operation is minimal and the good visibility of the work space is ensured. In this embodiment, the sheath for surgery as shown in FIG. 74 which widens owing to its elasticity can be used.

When the sheath 361 for surgery or the port 364 is inserted into the body, the soft pipe 3 which has been introduced into the body by the use of a core needle or a dilator may be used as a guide. The number of port guides is not limited to three, but may be two or four or more.

The twenty-third embodiment of this invention will be described with reference to FIG. 89–100.

FIG. 89 shows a sheath 380 for surgery belonging to a cavity-retaining system for surgery. The sheath 380 for surgery comprises a cavity-retaining member 381, and a cylinder sheet member 382 which acts as a tool guide means and is connected to the former. As the cavity-retaining means 381 includes a ring member constituted with a strip member having a mesh structure, to undergo free plastic deformation as shown in FIGS. 89A and 89B. The mesh structure of the ring member 383 may take alternative forms such as shown in FIGS. 90–92.

The mesh in FIG. 90 has a lattice structure which is formed after a plurality of slit-like openings are made in an interdigit pattern, and has such a property to undergo plastic deformation that it can maintain a contracted form as shown in FIG. 90A or a stretched form as shown in FIG. 90B.

The mesh in FIG. 91 is knit from cord materials 385, and can undergo plastic deformation such that it can maintain a contracted form as shown in FIG. 91A and a stretched form as shown in FIG. 91B.

The mesh in FIG. 92 is formed after cord members 386 are combined into a knit, and, in it, knots 386 are formed at intersections of adjacent cords. When, as shown in FIG. 92A, knots are released, the mesh contracts and when, as shown in FIG. 92B, knots are allowed to form, the mesh stretches. The cord itself 386 may not have a property to undergo plastic deformation, but the mesh made from the cord comes to have a property to maintain either stretched or contracted form.

The cavity-retaining means 381 may include a member which results after part of circular or ellipsoidal member made of a strip material has been folded, or may include a ring member to part of which has a mesh structure, though these modifications are not illustrated here.

The cylinder sheet member 382 which acts as a guide for tools is similar to the cylinder sheet member 312 of the sixteenth embodiment, and is used in the same way. The constricted segment at the tip of the cylinder sheet member 382 is connected to the ring member 383 of the cavity-retaining means 381, and the internal cavity of the cylinder sheet member 382 directly communicates with the internal cavity of the ring member 383. The cylinder sheet member 382 has at its tip a plurality of ports 388 for tool insertion adjacent to the internal wall of the ring member 383. The ports 383 for tool insertion are so formed as to allow a scope 391, a port 392 or the like to be introduced into the internal cavity maintained by the cavity-retaining means 381.

FIG. 93 shows a version of the cavity expander 393 which constitutes a cavity-retaining system for surgery. The cavity expander 393 has an insertion tube 394 which constitutes a hollow tube, and a balloon at the front end of the insertion tube 394 which acts as an attachment for the sheath 380 for surgery. The balloon 395, when inflated, take a form as shown in FIG. 93A, and, when deflated, takes a form as shown in FIG. 93B. FIG. 93C shows the sheath 380 for surgery which is attached to the cavity expander 393.

For the sheath 380 for surgery to be used, for example, after the soft pipe 303 has been inserted into the body, the sheath is introduced into the body using the soft pipe 303 as a guide. As a preparation for the insertion of the sheath 380 for surgery, the cavity expander 393 with the balloon contracted is inserted into the sheath 380 for surgery to allow the deflated balloon 395 to fit to the ring member 383 similarly contracted as shown in FIG. 93C. The sheath 380 for surgery with the cavity expander 393 attached is introduced into the soft pipe 303, and the cavity-retaining means 381 of the sheath 380 for surgery is advanced to reach a desired spot. When it has reached the desired spot, the soft pipe 303 is withdrawn. Then, as shown in FIG. 94A, the sheath 380 for surgery is left behind in the body. At this stage, a fluid is allowed to flow through the channel within the cavity expander 393 into the balloon 395, to inflate the balloon 395. As shown in FIG. 94B, the cavity retaining member 381 becomes larger than other adjacent elements, and forms a cavity in the interior of the ring member 383 which acts as a work space. Later, the balloon 395 is allowed to deflate, and the cavity expander 393 is withdrawn from the sheath 380 for surgery. Then, the same operation as in the sixteenth embodiment can be performed through the sheath 380 for surgery. At this stage, around the mesh and interstices there form indentations which act as a means to position the cavity (positioning means). Through this operation, body tissues interdigitates with the mesh and interstices, and thereby to fix the sheath 380 for surgery to the body.

The multi-port system as described in the twenty-second embodiments can be used for surgery by the use of the sheath 380 for surgery of this embodiment. In this case, a port 392 as shown in FIG. 95 is used. This port 392 has retractions 397 at its end. The port 392, as in the twenty-second embodiment, is inserted into the body following the guide of a dilator or a core needle. The port introduces its tip into the tool inlet 388 of the sheath 380 for surgery, and is connected to the sheath 380 for surgery by hooking the retractions 397 against the tool inlet 388 of the sheath as shown in FIG. 96. Through this operation, the port 392 communicates with the cavity or the work space retained by the cavity-retaining member 381 of the sheath 380 for surgery. Therefore, tools can be introduced through the port 393 into the cavity or the work space retained by the sheath 380 for surgery.

FIG. 97 shows how the above operation proceeds. A scope 391 or a treatment tool 396 is introduced through the port 392, and a specially formed tool 399 which can not pass through the port 392 is introduced into the sheath 380 for surgery because the sheath forms a soft port. In addition, the sheath 380 for surgery does not limit the movement of a tool which requires an inclined position for use, which will improve the handling of tools.

After operation is completed, the sheath 380 for surgery is recovered. For this, the soft pipe may be slid over the sheath 380 for surgery, to allow the latter to be withdrawn through it. Or, forceps are inserted around the periphery of the sheath 380 for surgery, to collapse the distended ring member 383, and then the sheath may be withdrawn.

Further, it will be possible to make a low invasive operation by employing the multi-port system which only requires small perforations, and, in addition, by using the cavity-retaining tool having a property to enlarge in combination. Such operation will prevent interference between tools, and allow satisfactory handling of tools and a good field of view. Further, as it employs a soft sheet as a material of the sheath for surgery, it exerts minimal rejecting activity towards adjacent body tissues, and thus is less invasive to the body. Furthermore, the sheath 380 for surgery allows the entry of a tool which does not pass through the port 392, and hence does not limit the movement of tools, which will improve the handling of tools.

Further, with this system the port 392 allows its channel to completely communicate spatially with the cavity within the sheath 380 for surgery by hooking the retractions against the wall of the sheath. Namely, the port 392 is snugly connected to the internal cavity of the sheath, and hence prevents entry of body tissues into the cavity. This ensures a good visibility of the cavity. Further, the channel ensures stable introduction of a tool into the cavity.

Still further, as the cavity-retaining member means is made of a material having a mesh structure, the mesh presses against surrounding tissues in all its expanse, maintains a cavity within it, and thus ensures a good visibility of the cavity. The external surface of the mesh structure has indentations, into the concavities of which enter surrounding tissues, and as a result the cavity-retaining member is fixed with respect to the surrounding tissues. This ensures stable fixation of the cavity-retaining means during operation.

In the above system, the port 392 is connected to the sheath 380 for surgery by inserting its end through the tool inlet 388 of the sheath 380 for surgery, but, as shown in FIG. 98, the perforations of the mesh structure of the ring member 383 of the cavity-retaining means 381 may be used as a guide hole for the insertion of tools. Alternatively, as shown in FIG. 99, the port 393 is allowed to have a thread 398 on its front end, and may be screwed into a perforation of the mesh of the ring member 383. FIG. 100 gives an outline of how these elements are combined in this embodiment. In this figure the sheath 380 for surgery is represented only by the ring member 383 of the cavity-retaining means 381, and the cylinder sheet member 382 is omitted from the figure. In this case, the ring member 383 may be recovered, after being collapsed with forceps, but, when it is made of a biodegradable material, it may be left in the body after operation.

The soft pipe member for the sheath for surgery of this invention has a plurality of channels within its space, and allows those channels to be used as separate passages for insertion of tools, and for supply and removal of saline and blood.

The above description has mainly focused upon the resection of a herniated intervertebral disc, but, needless to say, the present system can be applied with the same profit to any operations and diagnoses, regardless of whether the target organ is embedded in body tissues, or in a cavity, or in any other places in the body. Other inventions related with the present invention will be given below in order. It is possible to combine them as appropriate according to a given object.

The twenty-fourth embodiment of this invention will be described with reference to FIGS. 101–103.

As shown in FIG. 101, the surgery stripper of the twenty-fourth embodiment comprises an insert 401, a body 402 close to the base, and a treatment segment 403 at the tip. The insert 401 is connected reversibly with a connector 404 to the body 402.

The insert 401 is constituted with a pipe made of a resin or a metal, and uses its interior as a pipe for water suction and water feed 405 (see FIG. 102).

The body 402 is further provided with a water-feed pipe and a water-suction pipe not illustrated here which can communicate with the water feed/suction channel 405 of the insert 401. The two pipes are separately connected to channel open/closure buttons 406 and 407 to control the flow of a liquid or a gas. The channel open/closure button 406 is connected to a water-feed tube 408 which passes a liquid from a water source not illustrated here, while the channel open/closure button 407 is connected to a suction tube 409 which passes a liquid or a gas to a sucking source not illustrated here.

The treatment segment 403 is constituted, as shown in FIG. 102, with a spherical, elastic member 410 made of silicone or the like, and a mesh 411 which is so mounted as to cover the external surface of this elastic member 410. The elastic member takes a spherical form adapted for stripping of organs, and its part extends into the internal space of the water feed/suction channel of the insert 401. Its interior communicates with the water feed/suction channel 405, and a plurality of holes penetrate the outer wall of the elastic member 410.

The mesh 411 is made of nylon, a metal or the like, does not attract blood, and takes a form like a thumb stall. The terminal which is formed after the elastic member 410 has been inserted into the insert 401, and the mesh has covered the elastic member 410, is then fixed with a tube 413 which has a property to contract in the presence of heat.

When the surgery stripper with the above-described constitution is pressed lightly against a site of a body cavity from which it is desired to remove tissues, it is possible to strip the site of tissues.

When the channel open/closure button 406 for the water-feed tube is depressed, the channel not illustrated here is opened, and saline driven from a water-source passes through the water-feed tube 408, water feed/suction channel 405, holes 412 of the elastic member 410, and mesh 411 in order, to reach the body cavity. When the channel open/closure button 407 for the suction tube is depressed, the channel not illustrated here is opened, saline and blood remaining in the cavity passe through the mesh 411, holes 412 of the elastic member 410, the water feed/suction channel 405, and the suction tube 409 in order, to reach a sucking source.

As seen from above, as the surgery stripper of this embodiment includes the water feed/suction channel through the insert 401 and the body 402, it allows the cavity to be washed through water feed/suction, and the site of bleeding to be checked while the operation necessary for stripping is in progress. This device dispenses with replacement of forces for water feed or water suction during operation and thus shortens time required for operation.

Further, as the insert 401 and the body 402 can be reversibly connected, the insert which requires a complicated work for cleaning can be made disposable, which makes the operation sanitary and dispenses with works involved in cleaning.

Although in this embodiment, the elastic member 410 takes a spherical form whose surface is penetrated by holes 412, it is not limited to this form but may take, for example, a conical form whose side and bottom are penetrated by holes 412. Or, as shown in FIG. 103B, it may take a spherical form upon which at least a groove 414 communicating with the water feed/suction channel 405 is prepared. Or it may take a combination of above forms. A stripping segment adapted for the site to be treated will be obtained after its form and hardness have been modified appropriately according to the nature of that site Although the above embodiment is provided with two channel open/closure buttons 406 and 407, the number of channel open/closure buttons is not limited to two. The stripper may be provided with one channel open/closure button 406 for water feed, which activates sucking while water feed is arrested, to absorb saline and blood accumulated in the cavity.

Fixation of the mesh 411 to the insert 401 may take place through bonding or any other publicly known bonding methods.

The twenty-fifth embodiment of this invention will be described with reference to FIGS. 104–105.

The twenty-fifth embodiment is the same with the twenty-fourth one except that it allows the insertion of forceps into the stripper.

As shown in FIG. 104, the surgery stripper of the twenty-fourth embodiment comprises an insert 401, a body 421 close to the base, and a treatment segment 422 at the tip, and the insert 401 is connected with the connector 404 to the body 421.

To the rear end of the body 421 is placed a forceps port 423 whose internal diameter communicates nearly linearly with the forceps channel 430 which runs parallel with the water feed/suction channel 405 through the space within the insert 401. To the forceps port 423 is reversibly attached a rubber cap 424 which can hermetically seal the forceps channel 430.

The treatment segment 422 comprises, as shown in FIG. 105, an elastic member 426 which includes a passage 425 to communicate linearly with the channel 430, and a mesh 427 which covers the inner wall of the passage 425 and the outer wall of the elastic member 426. The terminal which is formed after the elastic member 426 covered with the mesh 427 has been applied to the external wall of the insert 401, is then fixed with a tube 413 which has a property to contract in the presence of heat. The elastic member 426 has, on its side wall, a plurality of holes which communicate with the water feed/suction channel 405.

The use of the surgery stripper with the above-described constitution, in addition to the procedures of the corresponding one in the twenty-fourth embodiment, consists of removing the rubber cap 424, inserting a forceps 429 into the forceps port 423, passing the forceps through the channel 430 in the insert 401 and through the passage 425 of the elastic member 426, and protruding it from the tip of the treatment segment 422, to work as a forceps.

As seen from above, the surgery stripper of this embodiment allows not only blunt stripping as in the twenty-sixth embodiment, but also the use of a forceps even during blunt stripping. This device is especially useful, for example, when bleeding occurs by accident during stripping operation: immediately a forceps is inserted into the forceps port 423, to stop bleeding. Thus, with this device bleeding can be avoided as much as possible.

Further, as the inner wall of the forceps port 423 is nearly linearly connected to the channel 430, the forceps can be easily guided straight to a site where bleeding occurs.

Further, when the surgery stripper of this embodiment is applied for endoscopic surgery, it will minimize damages inflicted to the patient, because it can reduce the number of perforations made on the body wall surrounding a cavity.

Although in this embodiment the mesh 427 covers the inner wall of the passage 425 of the elastic member 426, the mesh 427 may cover instead only the outer wall of the elastic member 426.

Further, although in this embodiment, the water feed/suction channel 405 and the forceps channel 430 are separately prepared, they can share the same channel. When the stripper meets two functions with one channel, the structure within the insert will become simpler which will lead to the reduction of production cost.

A modified version of the twenty-fourth embodiment will be described with reference to FIGS. 106–108. The elements corresponding with those in the twenty-fourth embodiments are represented by the same symbols and their explanation will be omitted. This modified version is different from the twenty-fourth embodiment in that the elastic member 410 is replaced with a mesh 411 and tubes.

As shown in FIG. 106, the surgery stripper of this modified version comprises an insert 410, a body 402 close at the base and a treatment segment 431 at the tip, and the insert 401 is connected with a connector 404 to the body 402.

As shown in FIG. 107A, a tube 432 is a small bore tube, and its tip 433 takes a spherical form whose diameter is slightly larger than the outer diameter of the tube, and through its interior runs a passage along the longitudinal axis to make a pore 434 on the spherical surface.

As shown in FIG. 107B, the treatment segment 431 comprises a bundle of tubes 432 inserted into the water feed/suction channel 405 of the insert 401. The outer tip surface of each tube 432 takes a spherical form. The pores 432 on the tubes 432 communicate separately with the water feed/suction channel 405.

When the stripper with above constitution is lightly pressed against a site in a body cavity from which it is desired to remove tissues bluntly, indentations formed by the top surfaces of tubes and interstices among the top surfaces are inserted into small gaps between tissues, and hence any adhesions of tissues can be stripped.

When the channel open/closure button 406 for the water-feed tube is depressed, the channel not illustrated here is opened, and saline driven from a water-source passes through the water-feed tube 408, water feed/suction channel 405 and individual pores 434 of tubes 432 in order, to reach the body cavity. When the channel open/closure button 407 for the suction tube is depressed, the channel not illustrated here is opened, saline and blood remaining in the cavity passes through the pores 434, the water feed/suction channel 405, and the suction tube 409 in order, to reach a sucking source.

As seen from above, the effects brought about by this modified version are the same as those brought about by the twenty-fourth embodiment. Although in this version the tube 432 takes a spherical form at its tip 433, it can take any form as long as that form is not harmful to the site to be treated.

As a further modification, as shown in FIG. 108, the top surface of a tube may take a semicircular form whose outer diameter is the same with that of the tube, or may take a curved surface which will, when combined with other surfaces of bundled tubes, take a semicircular form. These versions will bring about the same effects.

The twenty-sixth embodiment will be described with reference to FIG. 109.

The elements corresponding with those in the twenty-fourth embodiments are represented by the same symbols and their explanation will be omitted. This embodiment is different from the twenty-fourth embodiment in that a balloon is implemented.

As shown in the figure, the surgery stripper of this embodiment has a balloon 437 implemented close to the tip of the insert 401 but behind the treatment segment.

A gas feed tube 438 to communicate with the balloon 437 runs through the insert 401 and extends beyond the connector 404 outward. To its base end is firmly attached a metal cap 439 for gas feed. To this metal cap 439 is connected a tube which passes a gas from a gas feed source not illustrated here.

Before the insert 401 is introduced into the body, the balloon 437 remains collapsed. Once it has been introduced, a gas fed by the gas feed source not illustrated here passes through the metal cap 439 and the gas feed tube 438 into the balloon 437 behind the treatment segment 403. Through this operation, the balloon 437 is inflated as shown in FIG. 109. The balloon 437 pushes aside, by inflation, organs such as liver.

When this device is applied for a case where a hernia is to be corrected through periperitoneal approach, the peritoneum is stripped off from the abdominal wall firstly with the treatment segment, and a tunnel is formed between the two structures. After the insert 401 has been inserted into the tunnel, the balloon 437 is allowed to inflate which allows a wide stripping of the peritoneum and ensures a wide space for operation.

As seen from above, the surgery stripper of this embodiment not only brings about the same effects as seen in the twenty-fourth embodiment, but also allows rejection of nearby organs without inflicting undue damages to them.

Further, this stripper allows a wide stripping which will lead to a significant reduction of time required for operation.

The twenty-seventh embodiment of this invention will be described with reference to FIGS. 110–112.

The elements corresponding with those in the twenty-fourth embodiments are represented by the same symbols and their explanation will be omitted. This embodiment is different from the twenty-fourth embodiment in that the treatment segment can be expanded through activation from the operation segment implemented at the base.

As shown in FIG. 110, the surgery stripper of this embodiment comprises an insert 441, a body close at hand, and a treatment segment 442 at the tip, and the insert 441 is connected with a connector 404 to the body 402.

As shown in FIG. 111A, the external surface of the treatment segment 442 is covered with a mesh 443, and in its interior is placed an elastic member 444 which takes a nearly cylindrical form and is made of silicone or a spring material. The mesh 443 is knitted by a thread made of a resin such as nylon and has a contractility.

The basic end of the elastic member 444, together with the basic end of the mesh 443, is fixed to the front end of the insert 441 with a tube 445 which contracts by heating.

The front end of the elastic member 444 is folded inward, and the inwardly folded part 446 is bonded by a publicly known means such as bonding to the tip of a handling rod 447.

As shown in FIG. 112, along the long axis of the elastic member 444 are implemented slits 448 with an equal distance between adjacent ones in circumference.

As shown in FIG. 110, a handling rod 447 passes through the interior of the insert 441 and body 402, and comes out from the rear end of the body 402 to be connected to the handling segment 449. To the basic end of the body 402 is attached a rubber cap 450 which permits the handling rod 447 to pass through, and still prevents leaks through the gap with the external surface of the rod.

The treatment segment with the above constitution is inserted through a trocar not illustrated here into the body: as shown in FIGS. 111A or 112A, before insertion, it is allowed to take a cylindrical form which has a similar outer diameter to that of the insert 441.

Then, the handling segment 449 is drawn in by hand. In association with this movement, the handling rod 447 and the inwardly folded part 446 are displaced towards the base. As the folded part 446 moves towards the base, the interstices between slits 448 increasingly widen until the elastic member 444 is expanded in a radial direction, to become spherical, which makes blunt stripping possible as shown in FIGS. 111B and 112B.

Water feed/suction takes place through slits 448 and the mesh 443 under the control of the channel open/closure buttons 406 and 407.

After stripping is completed, the handling segment 449 is pushed in to the original position, and then the original state is resumed. Then, the insert 441 can be easily withdrawn from the trocar not illustrated here.

As seen from above, the surgery stripper of this embodiment not only brings about the same effects as seen in the twenty-fourth embodiment, but also relieves the patient from undue pains involved in operation because, as the treatment segment 442 is expandable, the insert can be made smaller in size. Although in this embodiment the elastic member 444 in the form of a cylinder has slits on its perimeter, the elastic member 444 may be composed of a plurality of strips which are then arranged into a cylinder. As a further modification, the elastic member 444 may be continuously united with the handling rod 447. Furthermore, the handling rod 447 may be made of a pipe which contains in its interior a second water feed/suction channel which is put to use in combination with a forceps.

The twenty-eight embodiment of this invention will be described with reference to FIG. 113–115.

The elements corresponding with those in the twenty-fourth embodiments are represented by the same symbols and their explanation will be omitted. This embodiment is different from the twenty-fourth embodiment in that the treatment segment can be expanded through activation from the operation segment implemented at the base of the body 402.

As shown in FIG. 113, the surgery stripper of this embodiment comprises an insert 441, a body 402 close at hand, and a treatment segment 452 at the tip, and the insert 441 is connected with a connector 404 to the body 402.

As shown in FIG. 114 a mesh 453 is knit by a thread made of a resin such as nylon, has a contractility, and is shaped like a bag. The bag-like mesh 453 is fixed all through its circumference to the front end of the insert 441 with a tube 445 which contracts by heating. This mesh 453 can be drawn in into the interior of the insert 441 or can be drawn out towards outside.

Further, a handling pipe 454 is inserted into the interior of the insert 441. An inflatable member 455 made of an elastic material such as silicone rubber, latex rubber or the like is attached to the tip of the handling pipe 454 in such a manner as to allow its interior to communicate with the internal cavity of the handling pipe 454. The inflatable member 455 has a plurality of openings 456, and is so constructed as to distribute a gas sent from a gas feed tube described later through the internal cavity of the handling pipe 454 and openings 456 into an inflating member 455.

The handling pipe 454, as shown in FIG. 113, passes through the insert 441 and the body 402, and comes out from the rear end of the body 402 to be connected to the handling segment 457. The handling pipe 454 can be inserted from the basic end of the body 402, and a rubber cap 450 is installed which is to prevent leaks of gas from the gap with the external diameter of the handling pipe.

On the side wall of the handling segment 457 is connected one end of a gas feed pipe 458 which communicates with the internal cavity of the handling pipe 454. On the other end is attached a metal cap 459 for gas feed which is to be connected to a gas feed source not illustrated here.

The treatment segment 452 with above constitution of the surgery stripper is introduced into the body through a trocar not illustrated here, after the mesh 453 has been folded into the internal cavity of the insert 441 as shown in FIG. 114.

Then, the handling segment 457 is pushed in. In association with this movement, the handling pipe 454 and the inflatable member 455 are displaced towards the front, and the mesh 453 together with the inflatable member 455 is pushed outside the insert, so that the mesh 453 comes to lie over the external surface of the inflatable member 455.

At this state, a gas expelled from a gas feed source not illustrated here passes through the metal cap 459, the gas feed tube 458 and the handling pipe 454 into the internal cavity of the inflatable member 455, to inflate the inflatable member 455 gradually. Thus, the mesh 453 gets closer contact with the external surface of the inflatable member 455. As a gas is more and more blown in, as shown in FIG. 115, the treatment segment 452 expands into a ball, which makes blunt splitting possible.

Water feed/suction takes place under the control of the channel open/closure buttons 406 and 407 by way of the gap between the inner wall of the insert 441 and the outer wall of the handling pipe 454, openings 456a prepared on the surface of the inflatable member 455, and on the interior, tip and external surface of the inflatable member 455, and mesh 453.

After stripping is completed, the inflatable member is allowed to contract, the handling segment 449 is drawn in to the original position to take in the inflatable member 455 into the interior of the insert 441, and the mesh 453 has an outer diameter similar to that of the insert, or less. Then, the insert can be easily withdrawn from the trocar not illustrated here.

After the inflatable member 455 has contracted sufficiently, the insert 441 may be withdrawn while the inflatable member is still left outside the insert 441.

As seen from above, the surgery stripper of this embodiment not only brings about the same effects as seen in the twenty-fourth embodiment, but also relieves the patient from undue pains involved in operation because, as the treatment segment 442 is expandable, the insert can be made smaller in size. Further, as the device is inserted into the body while the mesh 453 is kept drawn in into the internal cavity of the insert 441, the mesh 453 is kept protected until the time when it is used, and thus the mesh 453 is protected against undue damages.

The twenty-ninth embodiment of this invention will be described with reference to FIGS. 116–119.

The elements corresponding with those in the twenty-fourth embodiments are represented by the same symbols and their explanation will be omitted. This embodiment is different from the twenty-fourth embodiment in the constitution of the body 462.

As shown in FIG. 116, the surgery stripper of this embodiment comprises an insert 461, a body 462 close at hand, and a treatment segment 463 at the tip, and the insert 461 is connected with a connector 464 to the body 462.

As shown in FIG. 119, the treatment segment 463 comprises an elastic member 456, a connecting member 466 and a mesh 467. The elastic member 465 and the connecting member 466 cover the external surface of a flange 466a of the connecting member 466 and of the elastic member 465, and the mesh 467 is fixed after its basic end has been inserted between the elastic member 465 and connecting member 466, and bonded there.

The elastic member 465 and connecting member 466 of the treatment segment 463 has a channel at the center which communicates with a channel 468 of the insert 461. The elastic member 465 has an opening 469 at its tip through which the insert of a treatment tool described later can pass, and a plurality of holes on its external surface leading to the central channel 468.

Around the basic end of the connecting member 466 is placed a thread 471 which allows the member to engage reversibly with the tip of the insert. The elastic member 465 and the connecting member 466 have at least their part made of a material supplemented with a contrast agent or painted with a certain contrast agent.

As shown in FIGS. 116 and 119, the insert 472 of a treatment tool which can freely pass through the central channel 468 is continuous with an electrode 473 shaped like a letter L. The basic end of the tool passes through the channel 468 within the body 462 to come out from the rear end of the body 462. The protruded basic end is connected through a flange 472 whose diameter is larger than the external diameter of the tool insert 472, to a plug 475 which acts as a connector to a power source for diathermy not illustrated here. To the basic end of the body 462 is attached a rubber cap 476 which allows the passage of the tool insert 472 and prevents leaks through the gap with the external wall of that insert.

In the gap, between the flange 474 and the rubber cap 476, is inserted a coil spring 477 which surrounds the tool insert 472. This coil spring 477 gives a tension through the flange 472 to the tool insert 472 so that the electrode 473 prepared at the tip of the tool insert stays. within the channel 468.

As shown in FIG. 116, on the lateral wall of the body 462 close to the basic end, is attached an elastic plate 478 which is constituted with a rectangular, elastic member extending in parallel with the long axis of the tool insert 472.

Close to the basic end of the elastic plate 478 are jointed a nail-like process 479 which extends towards the tool insert 472 and whose tip is slightly curved towards front, and a handling strip 480 which is placed opposite to the process 479, and takes an L form towards the base.

The elastic plate 478, process 479 and handling strip 480 can be prepared as a unit, or may be prepared after any one of them has been separately prepared and combined with the rest. The elastic member includes metal plate springs, thin resin plates or the like, but it may be made of any material as long as it has a sufficient elasticity. The insert 461, body 462 and treatment segment 463 are made of an insulating material.

With the surgery stripper with above constitution, a cable from a diathermy power source not illustrated here is connected to the plug 475.

The stripper, while the coil spring being extended as shown in FIGS. 117 and 119 and the electrode 472 at the tip being kept retreated in the cavity of the treatment segment 463, is inserted into a body cavity. After its tip having penetrated into the cavity, the site to be treated is stripped of tissues bluntly with the mesh 467 prepared on the tip of the treatment segment 463. The open/closure buttons 406 and 407 are operated as appropriate to irrigate and evacuate the cavity.

When thin vessels or ligaments are encountered which are unresponsive to blunt stripping, the flange 474 is pushed towards the front end. Firstly, the front surface of the flange 474 gets contact with the process 479. When the flange is pushed in further, the process 479 is pushed aside by the flange 474, and the elastic plate 478 is bent outward, to allow the flange 474 to pass in front of the process 479. Once the flange has passed, the process resumes the original position through the elastic action from the elastic plate 478. At this stage, the flange 474 engages with the process 479, and, as shown in FIG. 118, the electrode 473 at the tip of the tool insert 472 protrudes from the opening 469 of the treatment segment 463, and stops there.

After the vessels and ligaments have been treated appropriately with the electrode 473, the handling strip 480 is moved towards the direction indicated by the arrow in FIG. 118. Then, the engagement of the process 479 with the flange 474 is released, and, through the spring action from the coil spring 77, the electrode 473 at the tip of the tool insert 472 retreats to the position within the treatment segment 463.

As seen from above, the surgery stripper of this embodiment not only brings about the same effects as seen in the twenty-fourth embodiment, but also improves handling of tools and shortens the time required for surgery, because the tool introduced into the channel 486 is allowed to stay at a retreated position within the treatment segment and, when in use, to stay at a protruded position at will.

Further, as a contrast agent has been added to a material that constitutes the treatment segment 463, or applied onto the surface of the segment, the segment can be easily located in the body by X-ray photography or other appropriate means, and could be safely recovered, even if the segment falls and is lost during operation.

Further, as the system allows only the treatment segment to be disposable, the use of system becomes sanitary and requires only a low cost. Furthermore, as the insert 461, body 462 and treatment segment 463 are all made of an insulating material, the operator is safely guarded against electric shocks even if electricity is supplied from the power source 473.

It is needless to say that various embodiments with a wide range could be constructed from this invention without stepping out of the scope and concept of this invention. This invention is not limited by any specific embodiments except by the claims attached herein.

What is claimed is:

1. A cavity-retaining tool for bone surgery comprises:
   a sheath for retaining a cavity which is introduced into body tissues and maintains a work space for bone surgery by retaining a cavity;
   a treatment channel which is prepared within the cavity-retaining sheath, and guides tools for the treatment of bones into the work space for bone surgery;
   an observation means which is prepared within the cavity-retaining sheath, and by which an operation field in the work space for bone surgery is observed; and
   a fitting member which is placed at a tip of the cavity-retaining sheath, and fits the tip of the cavity-retaining sheath to a bone, the fitting member including an end portion having contour means for mating the end portion to a selected surface of a bone.

2. A cavity-retaining tool for bone surgery according to claim 1 in which the end portion of the fitting member includes a bone fitting segment which allows the tip of the cavity-retaining sheath to fit faithfully to a shape of a bone.

3. A cavity-retaining tool for bone surgery according to claim 1 which further comprises:
   a core needle which is placed in the internal cavity of the cavity-retaining sheath, and acts as a support to facilitate the insertion of the cavity-retaining sheath into body tissues;
   an air-tightness retaining means which is placed in the internal cavity of the cavity-retaining sheath, and hermetically seals the gap with the cavity-retaining sheath; and
   an air-tight adapter which allows treatment tools to be introduced into the channel for treatment in an air-tight manner.

4. A cavity-retaining tool for bone surgery according to claim 1 in which the channel for treatment is further comprising provided with a depth control means which controls the depth down to which a treatment tool is allowed to descend for treatment.

5. A cavity-retaining tool for bone surgery according to claim 1 in which the observation means comprises a transparent member which is allowed to form at least part of the tip of the cavity-retaining sheath.

6. A cavity-retaining tool for bone surgery according to claim 1 in which the observation means comprises:
   a scope channel instituted in the cavity-retaining sheath; and
   an endoscope which is inserted through the scope channel.

7. A cavity-retaining tool for bone surgery according to claim 6 in which the cavity-retaining sheath has a channel for treatment which allows the insertion of tools necessary for bone treatment, and the scope channel and the treatment channel communicate directly or indirectly through an opening, with the internal passage of the cavity-retaining sheath.

8. A cavity-retaining tool for bone surgery according to claim 7 in which the fitting member is represented by an anchoring means implemented at the tip of the cavity-retaining sheath.

9. A cavity-retaining tool for bone surgery according to claim 7 or 8 in which each of the channels has its own air-tight means.

10. A cavity-retaining tool for bone surgery according to claim 6 in which the scope channel has a fixing means by which to fix an endoscope at a desired position.

11. A cavity-retaining tool for bone surgery according to claim 10 in which the fixing means is an O-ring.

12. A cavity-retaining tool for bone surgery according to claim 1 in which the observation means is a hole for observation prepared on the wall of the sheath.

13. A cavity-retaining tool for bone surgery according to claim 12 in which the observation hole is provided with a scope fitting means which fits the tip of a scope to the tip of the cavity-retaining sheath.

14. A cavity-retaining tool for bone surgery according to claim 13 in which the scope fitting means is an elastic material.

15. A cavity-retaining tool for bone surgery according to claim 1 in which the cavity-retaining sheath has a duplicate structure comprising inner and outer sheaths.

16. A cavity-retaining tool for bone surgery according to claim 15 in which the observation means, when observation windows are prepared on the tips of the inner and outer sheaths of the cavity-retaining sheath, consists of allowing, when the inner and outer sheaths are combined, the two observation windows to overlap.

17. A cavity-retaining tool for bone surgery according to claim 16 in which at least either one of the windows prepared at the inner and outer sheaths is made of a transparent material.

18. A cavity-retaining tool for bone surgery according to claim 15 in which the cavity-retaining sheath has an air-tight means between the inner and outer sheaths.

19. A cavity-retaining tool for bone surgery according to claim 15 in which the fitting member is coupled to the inner sheath.

20. A cavity-retaining tool for bone surgery according to claim 1 which has, in part of its wall, at least either of water feed channel or suction channel extending from the front end to the base end of the sheath.

21. A cavity-retaining tool for bone surgery according to claim 1 comprises:
a cavity-retaining sheath which is inserted into body tissues and maintains a work space for the treatment of a vertebral body by retaining a cavity;
a treatment channel which is prepared in the sheath and guides tools for the treatment of a vertebral body and an implant into the work space for the treatment of a vertebral body; and an observation means which is placed in the sheath and by which to observe endoscopically the operation field within the work space for the treatment of a vertebral body.

22. A cavity-retaining tool for bone surgery according to claim 1 in which the observation means is an endoscope passing through an internal cavity of cavity-retaining tool.

23. A cavity-retaining tool for bone surgery according to claim 22 in which the fitting member s represented by an anchoring means implemented at the tip of the cavity-retaining sheath.

24. A cavity-retaining tool for bone surgery according to claim 23 in which the anchoring means comprises:
at least a spike channel prepared in the wall of the cavity-retaining sheath; and
at least a spike which is driven into a bone after passing through the spike channel.

25. A cavity-retaining tool for bone surgery according to claim 24 in which the tip of the spike channel communicates either with the scope channel or with the treatment channel, and is placed within the visual field of the endoscope.

26. A cavity-retaining tool for bone surgery according to claim 24 in which the spike channels are shifted in position to one side in the cross-section of the sheath.

27. A cavity-retaining tool for bone surgery according to claim 24 in which the spike channel, at least its part, lies in the wall of the cavity-retaining sheath.

28. A cavity-retaining tool for bone surgery according to claim 24 in which the spike channel, at least its part, is placed close to the internal wall of the cavity-retaining sheath.

29. A cavity-retaining tool for bone surgery according to claim 23 in which the anchoring means is an anchoring member which is inserted into the channel for treatment, and comprises a stem which has a similar external diameter to the internal diameter of the treatment channel, and a needle member at the tip.

30. A cavity-retaining tool for bone surgery according to claim 1 which further comprises, at the tip of sheath for retaining a cavity, a sharp part capable of stripping a bone tissue of body tissues.

31. A cavity-retaining tool for surgery which is inserted into body tissues to be ready for use comprises:
a cavity-retaining member which retains a cavity for operation works in the body; and
a cylinder member which communicates with the cavity retained by the cavity-retaining member and interconnects a space outside of the body with the cavity, and is used for surgery, by allowing an endoscope and operation tools to be inserted through the cylinder member into the cavity retained by the cavity-retaining member, the cavity-retaining member including an end portion having contour means for mating the end portion to a selected surface of a bone.

32. A cavity-retaining tool for surgery according to claim 31 in which the cavity-retaining member comprises an inner wall facing the cavity and an outer wall facing body tissues.

33. A cavity retaining tool for surgery according to claim 32 in which the cavity-retaining member is a ring member.

34. A cavity retaining tool for surgery according to claim 32 in which the cavity-retaining member is made of a material which can undergo deformation, and expands the cavity with a cavity expanding means and retains the resulting cavity.

35. A cavity-retaining tool for surgery according to claim 31 or 32 which has a positioning means to maintain the cavity-retaining member with respect to a desired position in the body.

36. A cavity-retaining tool for surgery according to claim 35 in which the positioning means is a handling member which is connected to the cavity-retaining member and extends towards outside the body, and whose cross-sectional area is smaller than that of the cavity formed by the cavity-retaining member.

37. A cavity-retaining tool for surgery according to claim 36 in which the handling member has a channel to communicate with the cavity formed by the cavity-retaining member.

38. A cavity-retaining tool for surgery according to claim 35 in which the positioning means is represented by indentations formed upon the external wall surface of the cavity-retaining member.

39. A cavity-retaining tool for surgery according to claim 35 in which the positioning means has a retraction which extends from the tip of the cavity-retaining member towards the external wall, and which acts as a hook against body tissues.

40. A cavity-retaining tool for surgery according to claim 32 in which the cavity-retaining member has a hole prepared on at least a part of its wall which acts as a guide to introduce an endoscope or a tool into the cavity.

41. A cavity-retaining tool for surgery according to claim 32 in which, with regard to the cavity-retaining member, its internal cavity has long and short axes.

42. A cavity-retaining tool for surgery according to claim 41 in which the internal cavity of the cavity-retaining member has an ellipsoidal or elongated circular shape.

43. A cavity-retaining tool for surgery according to claim 31 in which the cylinder member is produced after a sheet member made of a resin has been made into a tube-like structure.

44. A cavity-retaining tool for surgery according to claim 31 in which the cylinder member is so constructed that its internal diameter is narrow at a tip and enlarges towards a base end.

45. A cavity-retaining tool for surgery according to claim 31 in which the cylinder member has its interior partitioned into a plurality of channels.

46. A cavity-retaining tool for surgery according to claim 31 in which the cylinder member has a hole prepared at least at one spot on the wall which acts as a guide to introduce an endoscope or a tool into the cavity.

47. A cavity-retaining tool for surgery according to claim 31 which has a guide member for tool insertion being connected to the cavity-retaining member and extending through the cylinder member towards outside the body, and in which the guide member for tool insertion is provided with a guide surface leading to the cavity formed by the cavity-retaining member.

48. A cavity-retaining tool for surgery according to claim 47 in which the guide member for tool insertion acts also as a handling member which is connected to the cavity-retaining means and extends towards outside the body.

49. A cavity-retaining tool for surgery according to claim 31 which is further provided with a bone fitting means which fits the tip of the cavity-retaining member to a bone.

50. A cavity-retaining tool for surgery according to claim 31 in which the cavity-retaining member further introduces an endoscope as an observation means by which to observe the operation field in the cavity for operation works.

51. A cavity-retaining tool for surgery according to claim 50 in which the endoscope is provided with an irrigating means.

52. A cavity-retaining tool for surgery according to claim 31 further comprising at least one port for tool introduction separate from the cavity-retaining tool which is led to the cavity retained by the cavity-retaining tool.

53. A cavity-retaining tool for surgery according to claim 52 further comprising an interconnecting means which connects the cavity-retaining member with the port.

54. A cavity-retaining tool for surgery according to claim 53 further comprising:

one of at least a part of a wall of its cavity-retaining member and a cylindrical member made of soft material having an elastic property; and a port insertion member which has a diameter allowing itself to be inserted into the port, and a needle segment which allows itself to penetrate through the part made of elastic material at a tip, and wherein interconnecting the cavity-retaining member with the port is achieved by penetrating an elastic material having an elastic property with the needle segment to produce a hole, by inserting the port through the hole, and by allowing the port to be connected by elasticity to the elastic material.

55. A cavity-retaining tool for surgery according to claim 53 in which:

the hole which is prepared on a part of the wall and communicates with the cavity for treatment is expandable and contractible; and the port which has a larger diameter than the hole, and the port is allowed to penetrate the hole while enlarging it and is connected by elasticity to the hole.

56. A cavity-retaining tool for surgery according to claim 54 or 55 in which the port has indentations at its tip.

57. A cavity-retaining tool for surgery according to claim 31 in which the soft tubular member is an elastic member.

58. A method involving the use of an endoscopic surgery system which comprises a sheath for surgery having a cavity-retaining means at a tip and includes a plurality of ports, and which consists of:

a. preparing a route for advancing into the body from a specific position and with a specific angle;

b. advancing a sheath for surgery along the route and retaining a cavity with a cavity-retaining means;

c. inserting, after the sheath is removed from the body, sheaths for endoscopic insertion and for tool insertion into the cavity retained by the cavity-retaining means;

d. inserting an endoscope either through the sheath for surgery or through the sheath for tool insertion, and then inserting tools through an unused sheath; and e. making an operation under endoscopic observation.

59. A surgery system comprising:

a cavity-retaining tool for surgery having a cavity-retaining member to retain a cavity for surgery works in a body, and a soft cylinder member which communicates with the cavity retained by the cavity-retaining member and interconnects the cavity with a space out of the body; and a body penetrating tool which produces an access route for the cavity-retaining tool for surgery by expanding a space between muscle fibers in the body tissue, the cavity-retaining member including an end portion having contour means for mating the end portion to a selected surface of a bone.

60. A surgery system according to claim 59 in which the body penetrating tool comprises a combination of a plurality of tubular members with different diameters increasing stepwisely.

61. A surgery system according to claim 59 in which, with regard to the body penetrating tool, its tip has a conical shape.

62. A surgery system according to claim 59 in which the body penetrating tool is a tubular member which allows an endoscope to pass through its interior, is provided with an observation window and has, at its end, at least either one of means for coagulating incision and stripping.

63. A surgery system according to claim 59 in which is further provided with a guide member which can be placed around the body penetrating tool, has a cavity sized for inserting a sheath for surgery therethrough and allows the cavity-retaining tool to be guided into body tissues.

64. A surgery system according to claim 59 in which the cavity-retaining tool can be placed around the body penetrating tool.

65. A surgery system according to claim 59 in which the body penetrating tool also acts as a guiding means to guide the cavity-retaining tool into the body.

66. An endoscopic surgery system, comprising:

a cavity retaining tool having a cavity-retaining means which is introduced through a skin incision into body tissues, and retains a cavity for surgery works, and a communicating means which communicates with the cavity retained by the cavity-retaining means and interconnects the cavity with the space out of the body;

at least one port for inserting tool as endoscope and treatment tools which is introduced through a skin incision other than above to penetrate the wall of cavity-retaining tool to be led into the cavity retained by the cavity-retaining tool; and an interconnecting means which interconnects the port and the cavity-retaining tool in body tissues.

67. An endoscopic surgery system according to claim 66 in which the cavity-retaining tool has the wall to divide the cavity from body tissue, the wall has at least a hole, the port is allowed to have a thread on its tip, and the port is interconnected to the hole by screwing the thread into the hole.

68. An endoscopic surgery system according to claim 66 in which the cavity-retaining tool has the wall to divide the cavity from body tissue, the wall has at least a hole, the port is allowed to have a retraction member extending radially on the tip, and the port is connected to the hole by inserting the retraction member into the hole.

69. An endoscopic surgery system according to claim 66 in which the cavity-retaining tool has the wall to divide the cavity from body tissue, the wall has at least a hole, and the hole is at the same time expandable and contractible; and the port which has a larger diameter than said hole, and the port is allowed to penetrate the hole while enlarging it and is connected by elasticity to the hole.

70. An endoscopic surgery system according to claim 69 in which:

at least a part of the cavity-retaining tool has a knitted part composed of a net line; and the interconnecting means is holes formed on the knitted part composed of the net line which allows the insertion of the port.

71. An endoscopic surgery system according to claim 69 further comprising a hole expanding means to expand a hole prepared on the wall of cavity-retaining tool wherein the port can be attached from outside to the expanding means.

72. An endoscopic surgery system according to claim 71 in which the hole expanding means comprises a combination of a plurality of tubular members with different diameters increasing stepwisely.

73. An endoscopic surgery system according to claim 71 in which, with regard to the hole expanding means, its tip has a conical shape, and its external size is the same with the internal diameter of the port.

74. An endoscopic surgery system according to claim 66 which is further provided with a port guide member to guide the port into the cavity.

75. An endoscopic surgery system according to claim 74 in which the port guide member comprises a port introducing part allowing introduction of the port, and a port introduction position determining means.

76. An endoscopic surgery system according to claim 75 in which:

the port introduction position determining means comprises a fitting part to fit to the cavity-retaining tool and an interconnecting part to interconnect the fitting part and the port introduction part; and the port introduction part is positioned such that the extension of its axis crosses the cavity.

77. A surgery system according to claim 66 in which:

at least a part of wall of the cavity-retaining tool is made of a soft material having an elastic property, and a port insertion member which has a diameter to allow itself to be inserted into the port for tool insertion, and has a needle segment at the tip which can penetrate the soft member having an elastic property; and interconnecting the cavity-retaining tool with the part is achieved by penetrating the soft material having an elastic property with the needle segment to produce a hole, by inserting the port through the hole, and by allowing the port to be connected by elasticity to the soft material.

78. An endoscopic surgery system according to claim 77 which further comprises a hole expanding means to expand a perforation through the wall member.

79. An endoscopic surgery system according to claim 78 in which the hole expanding means comprises a guide needle with a tip having a conical shape, and a combination of a plurality of tubular members with different diameters increasing stepwisely.

80. A cavity-retaining tool for retaining a cavity for surgery which is inserted through body tissues into the body comprising:

a cavity-retaining member to retain a cavity for surgery works in the body; and a communicating member to be connected to the cavity-retaining member and to interconnect the cavity with the space outside the body, wherein a cross-sectional area of the communicating member is smaller than an inner cross-sectional area of the cavity retained by the cavity-retaining member, the cavity-retaining member including an end portion having contour means for mating the end portion to a selected surface of a bone.

81. An endoscopic surgery system, comprising:

a cavity-retaining tool which is inserted into body tissues through an incision to retain a cavity in the body tissues; and a cavity-retaining tool insertion location finding member which is inserted into the body through the incision to find the insertion location of the cavity-retaining tool by detecting uneven forms of a hard tissue around a site to be treated in a deeper part of the body, the cavity-retaining tool insertion location finding member including an end portion having contour means for mating the end portion to a selected surface of a bone.

82. An endoscopic surgery system according to claim 81 further comprising a body penetrating tool which expands a space between muscles fibers in body tissues to produce an access route for the cavity-retaining tool.

83. An endoscopic surgery system according to claim 82 in which the cavity-retaining tool insertion position location finding member comprises:

a reference member which forms a frontal surface of the tip of body cavity penetrating tool to hit against an elevated part around a site to be treated, an index member which protrudes from the tip of cavity-retaining tool to fit into a depressed part around a site to be treated, and in which finding the insertion location of cavity-retaining tool is achieved:

by placing the body cavity penetrating tool and the cavity-retaining tool in parallel to allow them to move along their respective long axes; and by, when the two tools are inserted into the body until they hit against hard tissues, observing a difference in readings from the index member and reference member.

84. An endoscopic surgery system according to claim 81 in which the cavity-retaining tool insertion locating finding means comprises:

a reference portion of the tip of body cavity penetrating tool which hits against an elevated part around a site to be treated; and an index portion of the tip of cavity-retaining tool which fits into a depressed part around a site to be treated, and in which finding the insertion location of the cavity-retaining tool is achieved by fitting the reference and index portions to elevated and depressed parts of a hard tissue.

85. A cavity-retaining tool for bone surgery, comprising:

a cavity-retaining sheath which is inserted into body tissues so that an internal cavity thereof forms a work space for bone surgery;

a treatment channel attached to the cavity-retaining sheath to guide tools necessary for bone treatment into the work space for bone surgery;

an observation means attached to the cavity-retaining sheath by which to observe an operation field in the work space for bone surgery; and a tissue-contour fitting means placed at a tip of the cavity-retaining sheath for mating the tip faithfully to. a contour or shape of a bone.

86. A cavity-retaining tool for bone surgery according to claim 85 in which the tissue-contour fitting means takes a shape to fit faithfully to a shape of a bone.

87. A cavity-retaining tool for bone surgery according to claim 86 in which the tissue-contour fitting means takes a shape to fit faithfully to the shape of the anterior aspect of a vertebral body.

88. A cavity-retaining tool for bone surgery according to claim 87 in which the tissue-contour fitting means has a tip which is shaped like a curved surface to fit faithfully to the contour of lateral side of a bone.

89. A cavity-retaining tool for bone surgery according to claim 88 in which the tissue-contour fitting means has a tip which is shaped like an inclined surface.

90. A cavity-retaining tool for bone surgery according to claim 87 in which the tissue-contour fitting means has a tip which is provided with a lobular rejecting member.

91. A cavity-retaining tool for bone surgery according to claim 86 in which the tissue-contour fitting means has a shape to fit faithfully to the shape of a bone around a vertebral arch posterior to a vertebral body.

92. A cavity-retaining tool for bone surgery according to claim 91 in which the tissue-contour fitting means is constituted with a substantially cylindrical material, and a part of the wall of the cylindrical material protrudes from the tip.

93. A cavity-retaining tool for bone surgery according to claim 91 in which the tissue-contour fitting means is constituted with a substantially cylindrical material which is provided with a rejecting member extending towards the tip from a part of its wall.

94. A cavity-retaining tool for bone surgery according to claim 91 in which the tissue-contour fitting means is substantially shaped like a cylinder, and has an opening towards a spinous process side.

95. A cavity-retaining tool for bone surgery according to claim 91 in which the tissue-contour fitting means is substantially shaped like a cylinder having a cross-section which is an ellipsoid having a long and short axis, with the long axis corresponding with a cephalo-caudal direction.

96. A cavity-retaining tool for bone surgery according to claim 85 in which the tissue-contour fitting means is provided with a cavity expanding means by which to expand the internal cavity retained by the cavity-retaining sheath.

97. A cavity-retaining tool for bone surgery according to claim 85 in which the tissue-contour fitting means is provided with a deforming means by which to deform itself to fit faithfully to the shape of a bone to be fitted.

98. A cavity-retaining tool for bone surgery according to claim 97 in which the deforming means is made of a rubber-like soft material.

99. A cavity-retaining tool for bone surgery according to claim 97 in which the deforming means is made of an elastic material.

100. A cavity-retaining tool for bone surgery according to claim 97 in which the deforming means is at least a movable member of a tip of the cavity-retaining tool.

101. A cavity-retaining tool for bone surgery according to claim 1 or 85 in which the cavity-retaining tool is made of a material transmissive to X-rays.

* * * * *